United States Patent
Naleway et al.

(10) Patent No.: US 8,716,558 B2
(45) Date of Patent: May 6, 2014

(54) METHOD OF ALTERING GLYCOSYLATION OF PROTEINS IN RESPONSE TO NOJIRIMYCIN GLUCURONIDE IN A PLANT CELL EXPRESSING GLUCURONIDASE

(75) Inventors: John J. Naleway, Eugene, OR (US); Rachel A. Howard, Eugene, OR (US)

(73) Assignee: Marker Gene Technologies, Inc., Eugene, OR (US)

( * ) Notice: Subject to any disclaimer, the term of this patent is extended or adjusted under 35 U.S.C. 154(b) by 1863 days.

(21) Appl. No.: 11/316,114

(22) Filed: Dec. 19, 2005

(65) Prior Publication Data

US 2006/0105915 A1    May 18, 2006

Related U.S. Application Data

(60) Continuation-in-part of application No. 10/703,937, filed on Nov. 7, 2003, now abandoned, which is a division of application No. 09/343,325, filed on Jun. 30, 1999, now Pat. No. 6,656,917.

(51) Int. Cl.
    *C12N 15/82*    (2006.01)
(52) U.S. Cl.
    USPC ............ 800/288; 800/278; 800/284; 435/468
(58) Field of Classification Search
    None
    See application file for complete search history.

(56) References Cited

U.S. PATENT DOCUMENTS

| | | | |
|---|---|---|---|
| 4,518,532 A | 5/1985 | Umezawa et al. |
| 4,940,705 A | 7/1990 | Boshagen et al. |
| 4,975,278 A | 12/1990 | Senter et al. |
| 5,338,678 A | 8/1994 | Senter et al. |
| 5,358,866 A | 10/1994 | Mullen et al. |
| 5,545,548 A | 8/1996 | Senter et al. |
| 5,624,830 A | 4/1997 | Mullen et al. |
| 5,773,435 A | 6/1998 | Kadow et al. |
| 6,239,329 B1 | 5/2001 | Weigel et al. |
| 6,641,996 B1 | 11/2003 | Jefferson et al. |
| 6,656,917 B1 | 12/2003 | Naleway et al. |
| 7,087,420 B1 | 8/2006 | Jefferson et al. |
| 7,345,216 B2 | 3/2008 | Keetman et al. |

FOREIGN PATENT DOCUMENTS

| | | |
|---|---|---|
| GB | 2197653 A | 5/1988 |
| JP | 63166803 A | 7/1988 |
| WO | WO9204454 | 3/1992 |
| WO | WO 96/15435 | 5/1996 |
| WO | WO 96/16183 | 5/1996 |
| WO | WO 98/30709 | 7/1998 |

OTHER PUBLICATIONS

Okkels et al. Synthesis of cytokinin glucuronides for the selection of transgenic plant cells. (1997) Phytochemistry; vol. 46; pp. 801-804.*

Kieber, J. J. Cytokinins. (2002) In: The Arabidopsis Book; published by the American Society of Plant Biologists; pp. 1-25.*
Yoshida, K. Effects of nojirimycin and p-nitrop henyl-B-thioglucoside on cell wall break down during callus formation in rice root tissues in the presence of 2,4-D. (1997) Taisei Kensetsu Gijutsu Kenkyushoho; vol. 30; pp. 261-266.*
Joersbo et al. A novel principle for selection of transgenic plant cells: positive selection. (1996) Plant Cell Reports; vol. 16; pp. 219-221.*
Motyka et al. Cytokinin-induced upregulation of cytokinin oxidase activity in tobacco includes changes in enzyme glycosylation and secretion. (2003) Phyiologia Plantarum; vol. 117; pp. 11-21.*
Edberg et al. Comparison of B-glucuronidase-based substrate systems for identification of *Escherichia coli*. (1986) J. of Clinical Microbiology; vol. 24; pp. 368-371.*
Jin et al. Interaction of DNA-binding proteins with the 5'-flanking region of a cytokinin-responsive cucumber hydroxypyruvate reductase gene. (1998) Plant Molecular Biology; vol. 38; pp. 713-724.*
Naleway, J.J., Zhang, Y.Z., Bonnett, H., Galbraith, D.W., Haugland, R.P., "Detection of GUS Gene Expression in Transformed Plant Cells With New Lipophilic Fluorogenic β-Glucuronidase Substrates." J. Cell Biol. 115(3):151a. (1991).
R. A. Jefferson, S. M. Burgess, D. Hirsh "beta-Glucuronidase from *Escherichia coli* as a gene-fusion marker." Proc. Natl. Acad. Sci. USA 83: 8447-8451 (1986).
R.A. Jefferson, T.A. Kavanagh, M.W. Bevan "GUS fusions: beta-glucuronidase as a sensitive and versatile gene fusion marker in higher plants." EMBO J 6: 3901-3907 (1987).
P.N. Benfey, L. Ren, N.H. Chua "The CaMV 35S enhancer contains at least two domains which can confer different developmental and tissue-specific expression patterns." EMBO J 8: 2195-2202 (1989).
K.E. Broglie, P. Biddle, R. Cressman, R. Broglie "Functional analysis of DNA sequences responsible for ethylene regulation of a bean chitinase gene in transgenic tobacco." The Plant Cell 1: 599-607 (1989).
M. Keil, J.J. Sánchez-Serrano, L. Willmitzer "Both wound-inducible and tuber-specific expression are mediated by the promoter of a single member of the potato proteinase inhibitor II gene family." EMBO J. 8: 1323-1330 (1989).
B. Keller, J. Schmid, C.J. Lamb, "Vascular expression of a bean cell wall glycine-rich protein-b-glucuronidase gene fusion in transgenic tobacco." EMBO J 8: 1309-1314 (1989).

(Continued)

*Primary Examiner* — Cathy Kingdon Worley
(74) *Attorney, Agent, or Firm* — Timothy L. McCutcheon

(57) ABSTRACT

Novel pro-drugs and methods for their use to alter the growth and biological characteristics of living cells, tissues, or whole organisms are described. Such cells may include animal cells, plant cells and bacterial cells. The methods allow for selective activation of the pro-drugs at or near transformant host cells expressing a gene for an enzyme that activates the pro-drugs. Pro-drugs according to a preferred embodiment of the invention are conjugates of a bioactive compound and a chemical group that is capable of being cleaved from the bioactive compound by action of an enzyme. Methods according to this invention include, (a) introducing into targeted cells a gene encoding an enzyme and (b) administering a pro-drug, wherein the enzyme releases the pro-drug from conjugation. In a preferred embodiment of the invention, the gene encoding the enzyme is a marker gene. Methods according to a preferred embodiment of the invention include altering protein production in a plant cell such as altering glycosylation of a protein produced by the plant cell.

3 Claims, 1 Drawing Sheet

(56) References Cited

OTHER PUBLICATIONS

R.A. Jefferson, T.A. Kavanagh, M.W. Bevan, "The use of the *Escherichia coli* β-glucuronidase gene as a gene fusion marker for studies of gene expression in higher plants" Biochem. Soc. Trans. 15:17-18 (1987).

R.A. Jefferson, "The GUS Reporter Gene System." Nature 342:838 (1989).

J.J. Naleway, "Histochemical, spectrophotometric, and Fluorometric GUS substrates." in "GUS Protocols: Using the GUS Gene as a Reporter of Gene Expression" Gallagher, S.R., ed., Academic Press, San Diego, CA 4 (1992) 61-76.

Alexander, R.P., Beeley, N.R.A., O'Driscoll, M., O'Neill, F.P., Millican, T.A., Pratt, A.J., Willenbrock,F.W., "Cephalosporin Nitrogen Mustard Carbamate Prodrugs for ADEPT", Tet. Lett. 32:3269-3272 (1991).

Barnes, D., Sate, G., "Media for Growth of Cultured Cells in Serum-Free Medium", Anal. Biochemistry 102:255-270(1980).

Blakey, D.C., Valcaccia, B.E., East, S., Wright, A.F,, Boyle F.T., Springer C.J., Burke, P.J., Melton,R.G., Bagshawe, K.D., "Antitumor effects of an antibody-carboxypeptidase G2 conjugate in combination with a benzoic acid mustard prodrug", Cell Biophys., 22(1-3): 1-8 (1993).

Blazquez, M.A., Soowal, L.N., Lee, I., Weigel, D., "LEAFY expression and flower initiation in *Arabidopsis*" Development 124: 3835-3844 (1997).

Brown, F.J., Andisik, D.W., Bernstein, P.R., Bryant, C.B., Ceccarelli, C., Damewood J.R. Jr, Edwards,P.D., Earley, R.A., Feeney, S., Green, R.C., Gomes, B., Kosmider, B.J., Krell, R.D., Shaw, A., Steelman, G.B., Thomas, R.M., Vacek, E.P., Veale, C.A., Tuthill, P.A., Warner, P., Williams, J.C., Wolanin, D.J., Woolson, S.A., "Design of orally active, non-peptidic inhibitors of human leukocyte elastase", J. Med. Chem., 37(9):1259-61 (1994).

Chen, S.H., Kosai, K.I., Xu, B., Pham-Nguyen, K., Contant, C., Finegold, M.J., Woo, S.L.C., "Combination Suicide and Cytokine Gene Therapy for Hepatic Metastases of Colon Carcinoma: Sustained Antitumor Immunity Prolongs Animal Survival", Cancer Research 56:3758-3762 (1996).

Chiang, L.C., Silnutzer, J., Pipas, J.M., Barnes, D.W., "Serum-Free Cell Culture for Growth of NIH3T3 and 10T1/2 Mouse Embryo Fibroblast Cell Lines, SV40 Virus Propagation, and Isolation of SV40 Transformed Cells", in *Methods for Serum-Free Culture of Epithelial and Fibroblastic Cells*,pp. 265-276, Alan R. Liss, Inc. publ. New York, NY (1984).

Colledge, W.H., Evans, M.J., "Cystic fibrosis gene therapy", British Medical Bulletin 51(1): 82-90, (1995).

Culver, K.W., Vickers, T.M., Lamsam, J.L., Walling, H.W., Seregina, T., "Gene Therapy for solid tumors", British Medical Bulletin 51(1):192-204 (1995).

Delia, D., Aiello, A., Lombardi, L., Pelicci, P.G., Grignani, F., Grignani, F., Formelli, F., Menard, S., Costa, A., Veronesi, U., Pierotti, M.A., "N-(4-Hydroxyphenyl)retinamide Induces Apoptosis of Malignant Hemopoietic Cell Lines Including Those Unresponsive to Retinoic Acid", Cancer Res., 53(24):6036-41 (1993).

Eicher, S.A., Lotan, R., "Differential Effects of Retinoic Acid and N-(4-hydroxyphenyl)retinamide on Head and Neck Squamous Cell Carcinoma Cells", Laryngoscope 106: 1471-1475 (1996).

Fanjul, A.N., Delia, D., Pierotti, M.A., Rideout, D., Qiu, J., Pfahl, M., "4-Hydroxyphenyl Retinamide Is a Highly Selective Activator of Retinoid Receptors", J. Biol. Chem. 271(37):22441-22446 (1996).

Fichera, A., Michelassi, F., Arenas, R.B., "Selective Expression of carcinoembryonic antigen promoter in cancer cell lines: targeting strategy for gene therapy in colorectal cancer", Dis. Colon Rectum, 41(6): 747-754(1998).

Freeman, S.M., Abboud, C.N., Wartenby, K.A., Packman, C.H., Koeplin, D.S, Moolten, F.L., Abraham, G.N., "The "Bystander Effect": Tumor Regression When a Fraction of Tumor Mass Is Genetically Modified", Cancer Research 53:5274-5283 (1993).

Hall, Simon J., "Adenovirus-Mediated Herpes Simplex Virus Thymidine Kinase Gene and Ganciclovir Therapy Leads to Systemic Activity Against Spontaneous and Induced Metastasis in an Orthotopic Mouse Model of Prostate Cancer," Int. J. Cancer, 70:183-187 (1997).

Hanessian, S., Wang, J., "Design and synthesis ofa cephalosporin-carboplatinum prodrug activatable by b-lactamase", Can. J. Chem. 71:896-905 (1992).

Hempel, F.D., Weigel, D., Mandel, M.A., Ditta, G., Zambryski, P.C., Feldman, L.J., Yanofsky, M.F.,"Floral determination and expression of floral regulatory genes in *Arabidopsis*", Development 124:3845-3853 (1997).

Hu, H.M., Urba, W.J., Fox, B.A., "Gene-Modified Tumor Vaccine with Therapeutic Potential Shifts Tumor-Specific T Cell Response from a Type 2 to a Type 1 Cytokine Profile", J. Immunol., 161(6):3033-41 (1998).

Huennekens, F.M., "Development of Methotrexate a-Peptides as Prodrugs for Activation by Enzyme-Monoclonal Antibody Conjugates", Advan. Enzyme Regul. 37:77-92 (1997).

Illek, B., Fischer, H., Machen, T.E., "Genetic Disorders of Membrane Transport II. Regulation of CFTR by small molecules including $HC0_3$-", Amer. J. Physiol. 275 (Gastrointest. Liver Physiol. 38): G1221-G1226 (1998).

Isaccs, S.T., Shen, C.K.J., Hearst, J.E., Rapoport, H., "Synthesis and Characterization of New Psoralen Derivatives with Superior Photoreactivitv with DNA and RNA", Biochemistry 16(6): 1058-1064 (1977).

Jiang, C., Fang, S.L., Xiao, Y.F., O'Conner, S.P., Nadler, S.G., Lee, D.W., Jefferson, D.M., Kaplan, J.M., Smith, A.E., Cheng, S.H., "Partial restoration fo cAMP-stimulated CFTR chloride channel activity in deltaF508 cells by deoxyspergualin", Amer. J. Physiol. 275 (Cell. Physiol. 44): C171-C178 (1998).

Kerr, M.W., "Bioactivated Herbicides" in *The Society for Experimental Biology Seminar Series*, No. 38:199-210(1989).

Krapcho, A.P., Getahun, Z., Avery, K.L., Vargas, K.J., Hacker, M.P., "Synthesis and Antitumor Evaluations of Symmetrically and Unsymmetrically Substituted 1 ,4-Bis[(aminoallcyl)amino]anthracene-9,10-diones and 1 ,4-Bis[(aminoalkyl)amino]-5 ,8-dihydroxyanthracene-9, 10-diones", J. Med. Chem. 34:2373-2380 (1991).

Krasnow, M.A., Cumberledge, S., Manning, G., Herzenberg, L.A., Nolan, G.P., "Whole Animal Cell Sorting of *Drosophila* Embryos", Science 25 1:81-85 (1991).

Lapetina, E.G., Reep, B., Ganong, B.R., Bell, R.M., "Exogenous sn-I ,2-Diacylglycerols Containing Saturated Fatty Acids Function as Bioregulators of Protein Kinase C in Human Platelets", J. Biol. Chem., 260(3):1358-61(1985).

Lichtenhaler, F.W., Sanemitsu, Y., Nohara, T., "Synthesis of 5'-O-Glycosyl-ribo-nucleosides", Angew.Chem. Int. Ed. Engl. 17(10): 772-774 (1978).

Lira, S.A., Kinloch, R.A., Mortillo, S., Wassarman, P.M., "An upstream region of the mouse ZP3 gene directs expression of firefly luciferase specifically to growing oocytes in transgenic mice", Proc. Natl. Acad. Sci. USA 87: 7215-7219 (1990).

Marth, C., Beck, G., Daxenbichler, G., "Effect of 4-Hydroxyphenylretinamide and Retinoic Acid on Proliferation and Cell Cycle of Cultured Human Breast Cancer Cells", J. Natl. Cancer Inst. 75(5): 871-875 (1985).

Meyer, D.L., Jungheim, L.N., Mikolajczyk, S.D., Shepherd, T.A., Starling, J.J., Ahlem, C.N., "Preparation and Characterization of a b-lactamase-Fab' Conjugate for the Site-Specific Activation of Oncolytic Agent", Bioconjugate. J. 3(1):42-48 (1992).

Moon, R.C., Thompson, H.J., Beddi, P.J., Grubbs, C.J., Gander, R.J., Newton, D.L., Smith, J.M., Phillips, S.L., Henderson, W.R., Mullen, L.T., Brown, C.C., Sporn, M.B., "N-(4-Hydroxyphenyl)retinamide, A New Retinoid for Prevention of Breast Cancer in the Rat", Cancer Res. 39: 1339-1346 (1979).

Mullen, C.A., Kilstrup, M., Blaese, R.M., "Transfer of the bacterial gene for cytosine deaminase to mammalian cells confers lethal sensitivity to 5-fluorocytosine: A negative selection system" Proc. Natl. Acad. Sci. USA 89:33-37 (1992).

Nabel, E.G., Plautz, G., Nabel, G.J., "Site Specific Gene Expression in Vivo by Direct Gene Transfer into the Arterial Wall", Science 249:1285-1288 (1990).

(56) References Cited

OTHER PUBLICATIONS

Nabel, G.J., Nabel, E.G., Yang, Z.Y., Fox, B.A., Plautz, G.E., Gao, X., Huang, L., Shu, S., Gordon, D., Chang, A.E., "Direct gene transfer with DNA-liposome complexes in melanoma: Expression, biologic activity, and lack of toxicity in humans", Proc. Natl. Acad. Sci. USA 90:11307-11311 (1993).

Peters, M.T., Brigham, K.L., King, G.A., Meyrick, B.O., Gao, X., Stecenko, A.A., "Optimization of cationic liposome-mediated gene transfer to human bronchial epithelial cells expressing wild-type or abnormal cystic fibrosis transmembrane conductance regulator (CFTR)" Exp. Luna Res., 25(3):183-97 (1999).

Raz, E., Zloramik, G., Tsien, R.Y., Driever, W., "beta-Lactamase as a marker for gene expression in live zebrafish embryos", Devel. Biol. 203(2): 290-294 (1998).

Ring, C.J.A., et al., Suicide gene expression induced in tumor cells transduced with recombinant adenoviral, retroviral and plasmid vectors containing the ERBB2 promoter, Gene Therapy, 3:1094-1103 (1996).

Rosenfeld, M.E., Wang, M., Siegal, G.P., Alvarez, R.D., Mikheeva, G., Krasnykh, V., Curiel, D.T., "Adenoviral-mediated delivery of herpes simplex virus thymidine kinase results in tumor reduction and prolonged survival in a SCID mouse model of human ovarian carcinoma", J. Mol. Med. 74:455-462 (1996).

Sanes, J.R., Rubenstein, J.L.R., Nicolas, F., "Use of a recombinant retrovirus to study post-implantation cell lineage in mouse embryos", EMBO J. 5(12): 3133-3142 (1986).

Schneider, M., Ow, D.W., Howell, S.H., "The in vivo pattern of firefly luciferase expression in transgenic plants", Plant Mol. Biol. 14: 935-947 (1990).

Senter, P.D., Schreiber, G.J., Hirshberg, D.L., Ashe, S.A., Hellstrom, K.E., Hellstrom, I., "Enhancement of the in Vitro and in Vivo Antitumor Activities of Phosphorylated Mitomycin C and Etoposide Derivatives by Monoclonal Antibody-Alkaline Phosphatase Conjugates", Cancer Res. 49:5789-5792 (1989).

Smith, O., "Pain-Killer Genes", Science 284:1634 (1999).

Stalker, D.M., McBride, K.E., Malyj, L.D., "Herbicide Resistance in Transgenic Plants Expressing a Bacterial Detoxification Gene", Science 242: 419-423 (1988).

Tiraby, Michele, et al. Concomitant expression of E. coli cytosine deaminase and uracil phosphoribosyltransferase improves the cytotoxicity of 5-fluorocytosine, FEMS Microbiology Letters 167:41-49 (1998).

Touchette, N., "Cancer Researchers Seek Therapies to Zero in on Tumors", J. NIH Res. 4:64-65 (1992).

Umeda, Y., Moriguchi, M., Kuroda, H., Nakamura, T., Iinuma, H., Takeuchi, T., Umezawa, H., "Synthesis and Antitumor Activity of Apergualin Analogues", J. Antibiotics 38(7) :886-898 (1985).

Watanabe, K.A., Matsuda, A., Halat, M.J., Hollenberg, D.H., Nisselbaum, J.S., Fox, J.J., "Nucleosides. 114. 5'-O-Glucuronides of 5-Fluorouridine and 5-Fluorocytidine. Masked Precursors or Anticancer Nucleosides", J. Med. Chem. 24: 893-897 (1981).

Westerfield, M., Wegner, J., Jegalian, B.G., DeRobertis, E.M., Puschel, A.W., "Specific activation of mammalian HOX promoters in mosaic transgenic zebrafish", Genes & Devel. 6:591-598 (1992).

Wilson, S.P., Yeomans, D.C., Bender, M.A., Lu, Y., Goins, W.F., Glorioso, J.C., "Antihyperalgesic effects of infection with a preproenkephalin encoding herpes virus", Proc. Natl. Acad. Sci. USA 6:3211-3216 (1999).

Worley, C.K., Ling, R., Callis, J., "Engineering in vivo instability of firefly luciferase and Escherichia coli b-glucuronidase in higher plants using recognition elements from the ubiquitin pathway". Plant. Mol. Biol. 37: 337-347 (1998).

Yee, Douglas, et al. "Adenovirus-Mediated Gene Transfer of Herpes Simplex virus Thymidine Kinase in an Ascites Model of Human Breast Cancer," Human Gene Therapy, 7:1251-1257 (Jun. 20, 1996).

Zee-Cheng, R.K.Y., Cheng, C.C., "Antineoplastic Agents. Structure-Activity Relationship Study of Bis(substituted aminoalkylamino)anthraquinones". J. Med. Chem. 21(3): 291-294 (1978).

Zloranik, G., Negulescu, P.A., Knapp, T.E., Mere, L., Burres, N., Feng, L., Whitney, M., Roemer, K., Tsien, R.Y., "Quantitation of Transcription and Clonal Selection of Single Living Cells with b-Lactamase as Reporter", Science 279: 84-87 (1998).

Bakina, E., et al., "Intensely cytotoxic anthracycline prodrugs: galactosides," Anti-Cancer Drug Design, Dec. 1999, vol., 14(6), pp. 507-515, abstract.

Denny, W.A., et al., "The design of selectively-activated anti-cancer prodrugs for use in antibody-directed and gene-directed enzyme-prodrug therapies," J. Pharm. Pharmacol. 1998, vol. 50(4), pp. 387-394,abstract.

Farquhar, D., et al., "Antitumor galactoside prodrugs," Proc. Annu. Meet. Am. Assoc. Cancer Research, (1997), vol. 38, p. A4121, Abstract.

Farquhar, D., et al. "Antitumor galactoside prodrugs," Proc. Annu. Meet. Am. Assoc. Cancer Research Annual Meeting 1997, vol. 38, pp. 613-614, Abstract.

Marini F., et al., "E. coli LacZ as a suicide gene for anticancer prodrug activation," Proc. Annu. Meet. Am. Assoc. Cancer Research 1997, vol. 38, p. A2294, abstract.

International Search Report, for PCT US00/15156, Notification Date Sep. 2, 2001.

Abraham, Ralph, et al., "Conjugates of COL-1 Monoclonal Antibody and b-D-Galactosidase Can Specifically Kill Tumor Cells by Generation of 5-Fluorouridine from the Prodrug b-D-Galactosyl-5-Fluorouridine," Cell Biophysics, vol. 24/25 pp. 127-133 (1994).

* cited by examiner

US 8,716,558 B2

METHOD OF ALTERING GLYCOSYLATION OF PROTEINS IN RESPONSE TO NOJIRIMYCIN GLUCURONIDE IN A PLANT CELL EXPRESSING GLUCURONIDASE

The present application is a Continuation-in-Part of U.S. Ser. No. 10/703,937, filed Nov. 3, 2003, now abandoned; which is a divisional of U.S. Ser. No. 09/343,325 filed Jun. 30, 1999 and which issued as U.S. Pat. No. 6,656,917.

GOVERNMENT LICENSE RIGHTS

The U.S. Government has a paid-up license in this invention and the right in limited circumstances to require the patent owner to license others on reasonable terms as provided for by the terms of National Science Foundation SBIR Phase II Grant #DMI-9710722 Marker Gene Directed Substrates For Cell Regulation, National Institute of General Medical Sciences-NIH SBIR Phase II Grant #2R44GM54456-02 Genetic Strategies for Drug Targeting, National Science Foundation SBIR Phase I Grant #DMI-9561199 Marker Gene Directed Substrates for Cell Regulation, and National Institute of General Medical Sciences-NIH SBIR Phase I Grant #2R44GM54456-01A1 Marker Gene Directed Substrates for Cell Regulation.

BACKGROUND OF THE INVENTION

I. Field of the Invention

This invention relates to novel pro-drugs and methods for targeting and regulating the delivery of the pro-drugs to desired cells and tissues. More particularly, the invention relates to the use of transferred genes, preferably reporter or marker genes, with matched pro-drugs that are activated only in the transformed cells and the use of such systems for selecting transformed cells, affecting the cell growth or characteristics of the transformed cells, or as a means of drug targeting to specific cells or tissues in a mixed cell population.

II. Description of the Prior Art

Targeted and Regulated Drug Delivery.

Targeted and regulated delivery of biochemical agents has been investigated for a variety of uses. For example, targeted drug delivery systems have the potential to provide a mechanism for delivering cytotoxic agents directly to cancerous cells, tissue specific drugs to the lung epithelium for cystic fibrosis treatment, or analgesic drugs for chronic (neuropathic) pain treatment. In cancer treatment, the selective delivery of cytotoxic agents to tumor cells is desirable because systemic administration of these agents often kills normal cells within the body as well as the tumor cells sought to be eliminated. Antitumor drug delivery systems currently in use typically utilize a cytotoxic agent conjugated to a tumor-specific antibody to form an immunoconjugate. This immunoconjugate binds to tumor cells and thereby "delivers" the cytotoxic agent to the site of the tumor. Despite the amount of research directed toward the use of immunoconjugates for therapeutic purposes, several limitations involved in these delivery approaches have become apparent (see, e.g., Embleton, Biochem. Society Transactions, 14: 393, 615th Meeting, Belfast, 1986). For example, the large amount of drug required to be delivered to the target tumor cell to effect killing of the cell is often unattainable because of limitations imposed by the number of tumor-associated antigens on the surface of the cells and the number of drug molecules that can be attached to any given antibody molecule.

Methods of cloning genes for bioactive compounds directly into the cells to be affected also have been attempted. The use of cloned gene expression for cell regulatory purposes typically involves effecting cell ablation using a gene expression event. Attempts to express a toxic gene product in cells have not been generally successful. Toxic gene products are difficult to regulate. In addition, cells expressing a toxic product often down-regulate the expression of this toxic product in order to survive. Selection for cells that can survive despite the cloned gene activity also occurs. For example, the diphtheria toxin A-subunit has been transcribed under regulation of a developmentally regulated promoter system in tobacco plants for specific tissue ablation (Koltunow et al., 1990). Mariani et al. (1990) described expression of a chimeric ribonuclease gene to destroy reproductive cells in plants. Recent reports have described selective release strategies for naturally occurring, inactive phytohormone glycoside conjugates (β-glucosides) in cloned plant tissues using a Zea mays cDNA in tobacco roots (Brzobohaty, B., et al, 1993). Gene therapy techniques that include use of a chimeric gene encoding a fusion protein capable of increasing activity of pyrimidine analogs (Tiraby, R., et a., 1996) or combined suicide-gene techniques (Chen, S. H., et al., 1996) have also been reported.

Marker Genes.

Studies in the genetic and molecular basis of eukaryotic growth and differentiation have led to advances in many important areas, including the control of the cell cycle during development, the mechanism of the maternal effect on embryogenesis, and the molecular genetic basis of pattern formation. A byproduct of these studies has been the development of "reporter" or "marker" genes that are used as tools in such work. Studies with a variety of organisms and experimental systems have revealed that many important aspects of eukaryotic development are controlled by the differential expression of genetic information. Tissue specific promoters involved in the expression of developmentally important genes have been identified in various species. Marker genes are commonly used to monitor the effectiveness of these promoters.

Marker genes have been used outside of the study of tissue specific promoters. Expression of foreign genes in mammalian and plant cells has become the quintessential biotechnology protocol, and co-expressed marker genes have been used for several decades to track the expression levels of the simultaneous cloned genes (Roederer, M., et al., 1991). The activity encoded by a chimeric gene construct introduced by techniques of genetic engineering is sensitive, even to the point of measuring activity in single cells (Naleway, 1992; Naleway, et al., 1991). It has become conventional to construct and study gene fusions in which marker gene activity is restricted to particular cell types, tissues, organs, or stages of development.

Marker genes also have been used in combination with a suitable substrate to provide for detection of the protein expression. The substrate is applied to transgenic cells containing an active reporter or marker gene coding for an enzyme, the substrate is enzymatically turned over to a product that can be easily detected by visual or spectrophotometric techniques. Examples of such systems include the use of chromogenic substrates (like 5-bromo-4-chloroindolyl galactoside (X-Gal) for detection of lacZ ƀ-galactosidase activity in cells and tissues (Lim, K., et al., 1989; Marsh, J., 1994)), fluorogenic substrates (like 4-methylumbelliferyl glucuronide (MUG) for detection of ƀ-glucuronidase activity in plant cells or tissues (Jefferson, R. A., 1988)), or bioluminescent substrates (like luciferin for detection of cloned firefly luciferase activity in various cell or tissue types (Wood, K. V., et al., 1989)). In a related technique, a selection marker (gene) may also be used to confer antibiotic resistance to cells, tissues or organisms when a matched antibiotic is applied to the transgenic cells.

Certain qualities are necessary in a useful marker gene: typically, the lack of detectable intrinsic enzyme activity in the recombinant cells, the robust nature of the marker (usually a bacterial enzyme) and the availability of substrates to estimate the enzyme cloned activity allow sensitive detection of the marker gene (and therefore of any co-expressed gene of interest). The marker genes that are available for use during the genetic engineering of plants or animal cells have found widespread use in molecular biology and biotechnology for the selection, detection and analysis of transgenic cells or tissues.

E. coli lacZ Marker Gene.

The most frequently used reporter gene is probably the *Escherichia coli* lacZ gene, which encodes an active subunit of β-galactosidase (Lis, et al., 1984 and Beckwith, et al., 1970). The bacterial lacZ 3-Galactosidase enzymatic activity can be easily and sensitively measured, it can be expressed and assayed in virtually any type of cell, and its activity is unaltered by making N-terminal fusion polypeptides.

Firefly luciferase (luc) Marker Gene.

The luc gene from the American firefly *Photinus pyralis* (de Wet, et al., 1985, de Wet, et al., 1987, Brasier and Ron, 1992) has been widely used as a reporter of cloned gene activities in both plant and animal cells and tissues, both in vivo and in vitro using an assay with added ATP and appropriate buffer (containing $Mg^{+2}$). This assay is extremely sensitive, allowing detection of subattomole concentrations of enzyme.

Amp Selection Marker.

The selection markers for antibiotic resistance (i.e. amp for ampicillin resistance and tet for tetracycline resistance) are also some of the most widely used marker genes, now routinely incorporated into bacterial plasmid vectors (Bolivar, et al., 1977a; Bolivar, et al., 1977b). Since the (second) tetracycline resistance gene of many plasmids (e.g. pBR322) often contains the cloning site, this leaves ampicillin resistance as a major method of screening recombinant cells in many industrial biotechnology systems. Recombinant cells become capable of detoxifying the antibiotic ampicillin (applied to the media at a concentration of about 50 μg/mL), and are "selected", while non-transformed cells are ablated.

Other Marker Genes.

A list of common marker genes with their detection methods is given below:

| Reporter gene | Detection method (reagent) |
| --- | --- |
| Acid phosphatase | Colorimetric |
| Aequorin (phot) | Bioluminescent (coelenterazine) |
| | Colorimetric |
| Alcohol dehydrogenase | Colorimetric |
| Alkaline phosphatase | BL (luciferin phosphate) |
| | Chemiluminescent (CSPD) |
| | Colorimetric (PNPP) |
| | Colorimetric (BCIP) |
| | Colorimetric (AS-MXP) |
| Aminoglycoside phosphotransferase (aph (3') II) | Autoradiography ([$^{14}$C]chloramphenicol) |
| Catechol 2,3-dioxygenase (xylE) | Fluorescence (Bodipy chloramphenicol) |
| Chloramphenicolacetyltransferase (CAT) | Scintillation Counting ([$^3$H]acetyl-CoA) |
| | Immunoassay |
| *Firefly* luciferase (luc) | Bioluminescence (*Firefly* luciferin-ATP) |
| Galactokinase | |
| β-Galactosidase (lac Z) | Bioluminescence |
| | Colorimetric (ONPG) |
| | Colorimetric (X-GAL) |
| | Fluorescence (FDG) |
| | Fluorescence (MUGal) |
| β-Glucuronidase (gusA, uidA) | Chemiluminescence |
| | Colorimetric (X-GlcU) |
| | Fluorescence (MUGlcU) |
| Growth hormone | Immunoassay |
| Interleukin-2 (IL-2) | |
| Marine bacterial luciferase (lux A/B) | Bioluminescence ($FMNH_2$-decanal) |
| Neomycin phosphotransferase (neo) | |
| Ornithine transcarbamylase | |
| Phosphinothricin acetyltransferase (bar) | |
| Puromycin acetyltransferase (pac) | |
| *Renilla* luciferase (luc) | Bioluminescence |
| Thaumatin II | |
| Thymidine kinase | |
| Xanthine-guanine phosphoribosyltransferase | |
| *Vargula* luciferase | |

Note:
CSPD, disodium 3-(4-methoxy spiro[1,2-dioxetane-3,2'(5'-chloro)-tricyclo[3.3.1.1]decan]-4-yl phenyl phosphate;
FDG, fluorescein digalactoside; X-GlcU, 5-bromo-4-chloro-3-indolyl β-D-glucuronic acid;
MUGal, 4-methylumbelliferyl β-D-galactopyranoside;
MUGlcU, 4-methylumbelliferyl β-D-glucuronide;
NET, nitro blue tetrazolium;
ONPG, O-nitrophenyl β-D-galactopyranoside;
PNPP, 4-nitrophenyl phosphate;
X-GAL, 5-bromo-4-chloro-3-indolyl β-D-galactopyranoside.

SUMMARY OF THE INVENTION

The present invention provides methods and compounds to permit selection, detection or analysis of plant and animal cells during genetic engineering or to influence the growth or biological characteristics of cells or the organisms that contain these cells. It is an object of the present invention to extend the use of active marker genes beyond their use for detection of gene activity in living cells. A primary object of the invention is to allow targeting of novel pro-drugs to transgenic cells that contain a gene for an enzyme, preferably an active marker gene. The pro-drugs also may be targeted to surrounding cells or tissues. The present invention makes it possible to introduce an inactive biological agent into selected cells in culture, and thereby into selected tissues or whole organisms where it becomes activated by use of a cloned gene activity. Since the cloned gene for the enzyme is to be complementary to the pro-drug, release of the activated bioactive compound from the pro-drug form can be restricted to only those cells having the cloned gene in a mixed cell population or in tissues or whole organisms. Molecular biology techniques, such as the use of activatable promoter elements, cell or tissue specific promoters, or other cis- and trans-acting factors, capable of controlling gene expression may further restrict activation of the pro-drugs dependent upon expression of the cloned gene. The present invention provides compositions and methods for drug targeting and treatment for a variety of diseases including certain forms of cancer, cystic fibrosis, autoimmune diseases, proliferative and degenerative diseases, as well compositions and methods for use in agricultural biotechnology, the production of new proteins and drugs in cell-culture systems, bacterial screening strategies, and non-destructive selection mechanisms.

Other objects, advantages and features of the invention will be apparent from the following descriptions.

DETAILED DESCRIPTION

I. Definitions

Figure 1:
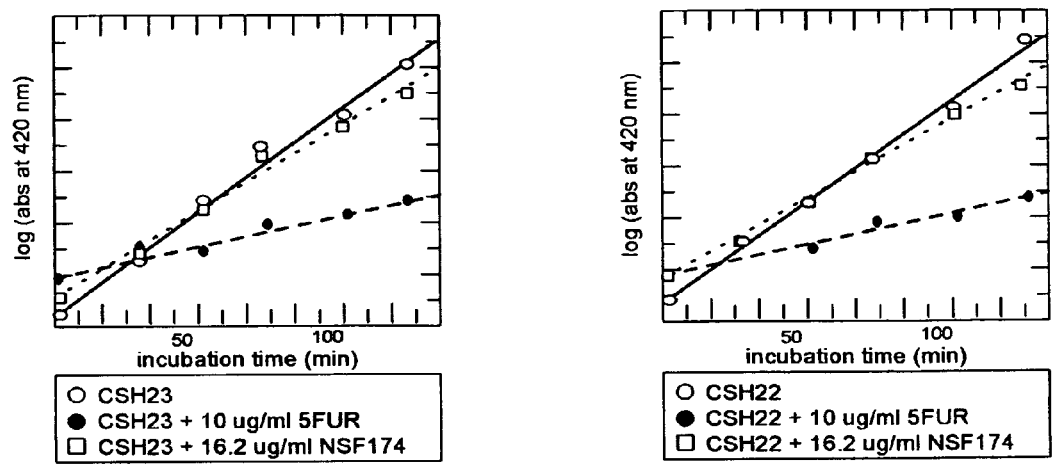
FIG. 1 shows growth plots of two *E. coli* strains, CSH23/S90C and CSH22/S90C, grown with 5-fluorouridine (5FUR) and 5-fluorouridine-5'-O-β-D-galactopyranoside (M0174).

The term "drug" as used in this application refers to any bioactive substance that has a positive or negative effect on cell growth, morphology, gene expression, immunochemistry, or biology.

The term "pro-drug" as used in this application refers to a precursor or derivative form of a bioactive compound that is less active compared to the parent bioactive compound and is capable of being enzymatically activated or converted into the more active parent form. See, e.g., Wilman, 1986 and Stella et al., 1985.

The term "biological activity" or "bioactive compound" is used to refer to any activity or a compound having an activity that can be assayed or measured including, but not limited to, any binding, blocking, chelating, enzymatic, agonistic, antagonistic, inhibitory, stimulatory, metabolic or structural activity.

II. Preferred Embodiments

According to one preferred embodiment of the present invention, the growth or biological characteristics of a genetically transformed mammalian, plant or bacterial cell sample are influenced by introducing a foreign gene or gene portion expressing the lacZ β-galactosidase enzyme; exposing the transgenic cells to a specific β-galactoside conjugate, and culturing the cells either in vitro or in vivo. Selection of the transgenic mammalian, plant or bacterial cell can be effected by utilizing a β-galactoside conjugate that improves the growth or viability of this cell at the expense of non-transformed cells, by application of a β-galactoside conjugate that releases an essential vitamin, growth factor, nutrient, hormone, phytohormone, or the like, or that satisfies an artificial or externally imposed block in metabolism.

According to another preferred embodiment of the present invention, the growth or biological characteristics of a genetically transformed mammalian, plant or bacterial cell sample are influenced by introducing a foreign gene or gene portion expressing the *E. coli* β-glucuronidase gene in the cells; exposing the transgenic cells to a specific β-glucuronide conjugate, and culturing the cells either in vitro or in vivo. Selective release of the conjugate is affected in a tissue or organ specific manner is achieved by use of tissue specific promoter control, or by inducing expression of the foreign gene in response to an externally applied signal by the use of an environmentally sensitive promoter system (circadian rhythm, heat-shock, inducible or other like promoter system).

According to yet another preferred embodiment of the present invention, the growth or biological characteristics of a genetically transformed mammalian, plant or bacterial cell sample are influenced by introducing a foreign gene or gene portion expressing the firefly luciferase gene (*Photinus*-luciferin:oxygen 4-oxireductase [decarboxylating, ATP-hydrolysing] (EC 1.13.12.7)), into either plant, bacterial or animal cells; exposing the transgenic cells to a specific D-luciferin conjugate of a bioactive compound, and culturing the cells either in vitro or in vivo, thereby influencing the growth or biological characteristics of the genetically transformed mammalian, plant or bacterial cell sample.

According to another preferred embodiment of the present invention, the growth or biological characteristics of a genetically transformed mammalian, plant or bacterial cell sample are influenced by introducing a foreign gene or gene portion expressing the ampicillin resistance gene (ampicilinase, amp, β-lactamase) wherein a plant, animal or bacterial cell sample is contacted with a specific cephalosporin-type conjugate of a bioactive compound, and cultured or in vivo growth maintained, thereby influencing the growth or biological characteristics of the genetically transformed mammalian, plant or bacterial cell sample containing a foreign gene or gene portion expressing the β-lactamase enzyme.

In another preferred embodiment of the invention, the activated drug product is translocated to neighboring cells or tissues, by enzymatic release within the transgenic cells, when the pro-drug is applied to a mixed cell population containing both transgenic and non-transgenic cells. The effect of the active product on neighboring non-transgenic cells (so-called "by-stander effect") elicits drug targeting in these tissues and within whole organisms.

Other embodiments of the present invention will readily occur to those of ordinary skill in the art in view of the disclosure herein.

A. Pro-Drugs and Matched Enzymes.

Many marker genes may be used in the present invention. The marker gene will code for an enzyme activity that is atypical of the cells or tissues being employed. Any pro-drug that is activated by the enzyme expressed in the transformed cells may be used in the present invention. The variety of pro-drugs that may be produced and used in the present invention include, but are not limited to, members of the following classes of bioactive compounds: immuno-stimulatory compounds including Phorbol Esters (Phorbol Myristate Acetate), Lipid A analogs and diacylglycerols, Retinoic Acid, insulin, cyclic nucleotides (cAMP), and protein kinase C activators as well as nutrients (serum components such as essential amino acids), D-glucose (lactose), hormones (including dexamethasone, dihydrotestosterone, aldosterone, progesterone, other glucocorticoid hormones, L-thyroxine and triiodo-L-thyronine), vitamins (including choline, folic acid, myo-inositol, niacinamide, pyridoxal, riboflavin, pantothenic acid, thiamine) toxins (for example, cycloheximide and psoralen), enzyme inhibitors (preferably specific kinase or glycosidase inhibitors), plant herbicides such as bromoxynil (4-hydroxy-3,5-dibromobenzonitrile), atrazine (2-chloro-4-ethylamino-6-isopropylamino-sym-trazine), dinoseb (2-sec-butyl-4,6-dinitrophenol), phosphinothricin, 2'-deoxyadenosine, 3'-deoxyadenosine (cordycepin) and ara-A, angiogenesis inhibitors (for example, endostatin and angiostatin), antitumor chemotherapeutic compounds (for example, doxorubicin, mitoxantrone, 5-fluorouridine and 5-fluorouracil, resveratrol, methotrexate, or 4-hydroxyphenylretinamide), as well as all classes of analgesic and therapeutic drugs that are known to exhibit positive or negative effects on the growth and development of cells. The factors that contribute to making a drug reliable and easy to conjugate are the availability of an aliphatic or aromatic hydroxyl, amino, thio, carboxyl or aldehyde group that is located at a position in the drug or bioactive compound whereby conjugation at this position reduces or eliminates biological activity.

The preferred substrates of this invention are drug conjugates represented by the general formula:

BLOCK-L-X-DRUG$_{(-XH)}$ wherein the group DRUG$_{(-XH)}$ represents a portion of a bioactive compound as further described below, known to have a strong positive or negative effect on the biological function, growth or characteristics of a cell, tissue or organism. The native bioactive compound generally has the formula H—X-DRUG$_{(-XH)}$ in its active form. The bioactive compound maybe for example, an antimetabolite, enzyme inhibitor, essential vitamin, essential nutrient, growth regulatory compound, a compound capable of inducing gene expression, hormone, or cytokinin.

BLOCK represents a group that changes the biological activity of the bioactive compound, and is capable of being cleaved from the substrate molecule by action of an enzyme. Preferably BLOCK causes a significant reduction or elimination of activity for the bioactive compound in the substrate. BLOCK is selected to be specific for the enzyme of interest. Preferably BLOCK is a monovalent moiety derived by removal of a hydroxyl group from an alcohol or from a carboxy group of an aliphatic, aromatic or amino acid, or of a peptide; or a monovalent moiety derived by removal of the anomeric hydroxyl group from a mono- or polysaccharide. Some preferred monovalent blocking groups and the enzymes that will cleave such groups from the substrate are listed below. Additional BLOCK groups, or derivatives or analogs of the described BLOCK groups listed below also may be used in the present invention.

| E.C. Number | ENZYME | BLOCK Group |
|---|---|---|
| 3.2.1.1 | α-amylase | (1-4) αD-Glucose |
| 3.2.1.2 | β-amylase. | (1-4) βD-Glucose |
| 3.2.1.3 | Glucan 1,4-α-glucosidase. | (1-4) αD-Glucose |
| 3.2.1.4 | Cellulase. | (1-4) βD-Glucose |
| 3.2.1.7 | Inulinase. | (2-1) βD-Fructose |
| 3.2.1.11 | Dextranase | (1-4) βD,(1-3) αD-Glucose |
| 3.2.1.14 | Chitinase. | (1-4) βD-GlcN |
| 3.2.1.15 | Polygalacturonase | (1-4) αD-GlcU |
| 3.2.1.18 | Exo-α-sialidase. | N-Ac-Neuraminic Acid |
| 3.2.1.20 | α-Glucosidase | α-D-Glucose |
| 3.2.1.21 | β-Glucosidase | β-D-Glucose |
| 3.2.1.22 | α-Galactosidase | α-D-Galactose |
| 3.2.1.23 | β-Galactosidase | β-D-Galactose |
| 3.2.1.24 | α-Mannosidase | α-D-Mannose |
| 3.2.1.25 | α-Mannosidase | β-D-Mannose |
| 3.2.1.30 | N-Acetyl-β-Glucosaminidase | β-D-N-Acetylglucosamine |
| 3.2.1.31 | β-Glucuronidase | β-D-Glucuronic acid |
| 3.2.1.37 | Xylan 1,4-β-xylosidase | 1,4-β-xylose |
| 3.2.1.38 | β-D-fucosidase | β-D-Fucose |
| 3.2.1.40 | α-L-rhamnosidase | α-L-Rhamnose |
| 3.2.1.43 | β-L-rhamnosidase | β-L-Rhamnose |
| 3.2.1.49 | α-N-acetylgalactosaminidase | α-N-Ac D-Galactose |
| 3.2.1.50 | α-N-acetylglucosaminidase | α-N-Ac D-Glucose |
| 3.2.1.51 | α-L-fucosidase | α-L-Fucose |
| 3.2.1.52 | β-N-acetylhexosaminidase | β-N-Ac D-Glucose |
| 3.2.1.53 | β-N-acetylgalactosaminidase | β-N-Ac D-Galactose |
| 3.2.1.55 | α-L-arabinofuranosidase | α-L-Arabinofuranose |
| 3.2.1.76 | L-iduronidase | L-Iduronic acid |
| 3.2.1.80 | Fructan β-fructosidase | β-Fructose |
| 3.2.1.88 | β-L-arabinosidase | β-L-Arabinose |
| 3.2.1.108 | Lactase | Lactose |
| 3.2.1.112 | 2-deoxyglucosidase | 2-Deoxyglucose |
| 3.2.3.1 | Thioglucosidase | 1-Deoxy-1-thio-Glucose |
| 3.5.2.6 | β-lactamase | Penicillin, Cephalosporin |
| 1.13.12.5 | *Renilla*-luciferin | 2-monooxygenase Aequorin |
| 1.13.12.6 | Cypridina-luciferin | 2-monooxygenase |
| 1.13.12.7 | Photinus-luciferin (4-4-monooxygenase); *Firefly* luciferase; Luciferase | D-Luciferin (5-Hydroxymethyl-D-Luciferin) |
| 1.13.12.8 | Watasemia-luciferin | 2-monooxygenase |

The group H—X represents an atom or atoms in the structure of the native bioactive compound where attachment of a BLOCK group is facilitated. The group H—X can include, but is not limited to, hydroxyl (—OH), amino (—NH$_2$), thiol (—SH), carboxyl (—COOH), aldehyde (—CHO), carbamyl (—CONH$_2$), or any other group that allows stable, specific, enzyme cleavable attachment of a BLOCK group to the bioactive compound. The group X represents the remaining atoms of H—X after removal of a hydrogen (H) atom by chemical attachment.

The position of the group H—X in the native drug compound is chosen so that the resulting substrate molecule can, by action of an enzyme, release the native drug in its active form, and so that attachment of the BLOCK group reduces or eliminates such activity.

The group L represents a linking group that may or may not be present in the substrate. This linking group may be present to facilitate chemical synthesis of the final substrate. Preferably L is a divalent moiety linking BLOCK with X. The group L must itself be either enzyme cleavable by a ubiquitous enzyme activity, or become unstable and be removed under physiological conditions after enzyme activity releases the BLOCK group. The group L can include, but is not limited to the carbonyl (C=O) group, as part of a carbonate, carbamate thiocarbonate, or other linkage in the final substrate.

The pro-drugs are formed in general as follows: For glycosides, the (suitably protected) bioactive compound is reacted under anhydrous conditions with acetobromogalactose, acetochloroglucuronic acid, methyl ester, or other activated sugar, using a silver or mercury type catalyst (silver carbonate, silver triflate, silver oxide and iodine, etc.) and non-nucleophilic base (sym-collidine) in an anhydrous solvent (like dichloromethane) for several days at room temperature in the dark. After purfication of the fully protected conjugate by standard silicagel chromatorgraphy conditions, the protected conjugate is deprotected using catalytic anhydrous base (such as sodium methoxide, lithium hydroxide, etc.). For cepahalosporin derivatives, a suitably protected cephalothin derivative such as 7-N-benzyl-cephalosporanic acid, diphenylmethylester is esterified with a bioactive compound (or protected bioactive compound), using standard techniques (dicyclohexylcarbodiimide, catalytic dimethylaminopyridine in dichloromethane). After purification using silicagel chromatography techniques, the completely protected conjugate is deprotected using trifluoroacetic acid, and/or other agents for the drug deprotection. For D-luciferin derivatives, 5-Hydroxymethyl-D-Luciferin is reacted with one equivalent of dicarbonylimidazole and the bioactive compound or suitably protected bioactive compound analog added (1 equivalent). This product, after purification as above, is deprotected and purified to homogeneity as above.

Some examples of pro-drugs and specific methods of forming the them are described below and in the Examples. The number, classes and types of drugs or bioactive compounds is, however, not limited to these examples:

Cycloheximide 2-O-β-D-Galactopyranoside (3-[2-(3,5-dimethyl-2-oxocyclohexyl)-2-O-β-D-galactopyranosyl)ethyl] glutarimide), Dexamethasone 21-O-β-D-galactopyranoside (21-O-β-D-galactopyranosyl-9-fluoro-11,17-dihydroxy-16-methylpregna-1,4-diene-3,20-dione, Dexamethasone 11-O-β-D-galactopyranoside (21-O-β-D-galactopyranosyl-9-fluoro-21,17-dihydroxy-16-methylpregna-1,4-diene-3,20-dione, Dexamethasone 17-O-β-D-galactopyranoside (21-O-β-D-galactopyranosyl-9-fluoro-21,11-dihydroxy-16-methylpregna-1,4-diene-3,20-dione, Dexamethasone 21,11-di-O-β-D-galactopyranoside (21-O-β-D-galactopyranosyl-11-O-β-D-galactopyranosyl-9-fluoro-17-hydroxy-16-methylpregna-1,4-diene-3,20-dione, Dexamethasone 21,17-di-O-β-D-galactopyranoside (21-O-β-D-galactopyranosyl-17-O-β-D-galactopyranosyl-9-fluoro-11-hydroxy-16-ethylpregna-1,4-diene-3,20-dione, Dexamethasone 11,17-di-β-O-D-galactopyranoside (11-O-β-D-galactopyranosyl-17-O-β-D-galactopyranosyl-9-fluoro-21-hydroxy-16-methylpregna-1,4-diene-3,20-dione, Dexamethasone 11,17,21-tri-β-O-D-galactopyranoside (11-O-β-D-galactopyranosyl-17-O-β-D-galactopyranosyl-11-O-β-D-galactopyranosyl-9-fluoro-16-methylpregna-1,4-diene-3,20-dione, 4'-O-β-D-galactopyranosylmethyl-2,5,9-trimethylpsoralen, Chloramphenicol 3-O-β-D-galactopyranoside (D(−)-threo-2,2-dichloro-N-[β-hydroxy-α-(O-β-D-galactopyranosylmethyl)-β-(4-nitrophenyl)ethyl] acetamide, 5-Fluorouridine-5'-O-β-D-D-Galactopyranoside, Tetracycline 10-O-β-D-Galactopyranoside [(4S-(4a,4aa,5aa,6b,12aa)]-4-(dimethylamino)-1,4,4a,5,5a,6-11,12a-octahydro-3,6,12,12a-tetrahydroxy-10-O-β-D-galactopyranosyl-6-methyl-1,11-dioxo-2-naphthalenecarboxamide), Tetracycline 3-O-β-D-Galactopyranoside [(4S-(4a,4aa,5aa,6b,12aa)]-4-(dimethylamino)-1,4,4a,5,5a,6-11,12a-octahydro-6,10,12,12a-tetrahydroxy-10-O-β-D-galactopyranosyl-6-methyl-1,11-dioxo-2-naphthalenecarboxamide), Tetracycline 6-O-β-D-Galactopyranoside [(4S-(4a,4aa,5aa,6b,12aa)]-4-(dimethylamino)-1,4,4a,5,5a,6-11,12a-octahydro-3,10,12,12a-tetrahydroxy-10-O-β-D-galactopyranosyl-6-methyl-1,11-dioxo-2-naphthalenecarboxamide), Tetracycline 12-O-β-D-Galactopyranoside [(4S-(4a,4aa,5aa,6b,12aa)]-4-(dimethylamino)-1,4,4a,5,5a,6-11,12a-octahydro-3,6,10,12a-tetrahydroxy-10-O-β-D-galactopyranosyl-6-methyl-1,11-dioxo-2-naphthalenecarboxamide), Tetracycline 12a-O-β-D-Galactopyranoside [(4S-(4a,4aa,5aa,6b,12aa)]-4-(dimethylamino)-1,4,4a,5,5a,6-11,12a-octahydro-3,6,10,12-tetrahydroxy-10-O-β-D-galactopyranosyl-6-methyl-1,11-dioxo-2-naphthalenecarboxamide), Dexamethasone 21-O-β-D-galactopyranoside (21-O-β-D-galactopyranosyl-9-fluoro-11,17-dihydroxy-16-methylpregna-1,4-diene-3,20-dione), Dexamethasone 11-O-β-D-galactopyranoside (11-O-β-D-galactopyranosyl-9-fluoro-17,21-dihydroxy-16-methylpregna-1,4-diene-3,20-dione), Dexamethasone 17-O-β-D-galactopyranoside (17-O-β-D-galactopyranosyl-9-fluoro-11,21-dihydroxy-16-methylpregna-1,4-diene-3,20-dione), Dexamethasone 11,21-di-O-β-D-galactopyranoside (11,21-di-O-β-D-galactopyranosyl-9-fluoro-17-hydroxy-16-methylpregna-1,4-diene-3,20-dione), Dexamethasone 11,17,21-tri-O-β-D-galactopyranoside (11,17,21-tri-O-β-D-galactopyranosyl-9-fluoro-16-methylpregna-1,4-diene-3,20-dione), Dexamethasone 17,21-di-O-β-D-galactopyranoside (11,21-di-O-β-D-galactopyranosyl-9-fluoro-11-hydroxy-16-methylpregna-1,4-diene-3,20-dione), Dexamethasone 11,17-di-O-β-D-galactopyranoside (11,21-di-O-β-D-galactopyranosyl-9-fluoro-21-hydroxy-16-methylpregna-1,4-diene-3,20-dione), N-Benzyl Cephalothin L-glutamate (6R[6a,7b(R*)]-3-a-(aminoglutaryloxy)methyl)-7-(phenylacetyl)amino-8-oxo-5-thia-1-azabicyclo[4.2.0]oct-2-ene-2-carboxylic acid), Doxorubicin 4'-O-β-D-galactopyranoside (8S-cis)-10-[3'-amino-4'-O-β-D-galactopyranosyl-2',3',6'-trideoxy-a-L-lyxo-hexopyranosyl)oxy]-7,8,9,10-tetrahydro-6,8,11-trihydroxy-8-hydroxyacetyl)-1-methoxy-5,12-naphthacenedione), Doxorubicin 6-O-β-D-galactopyranoside (8S-cis)-10-[3'-amino-2',3',6'-trideoxy-a-L-lyxo-hexopyranosyl)oxy]-7,8,9,10-tetrahydro-8,11-dihydroxy-8-hydroxyacetyl)-1-methoxy-5,12-naphthacenedione), Doxorubicin 8-O-β-D-galactopyranoside (8S-cis)-10-[3'-amino-2',3',6'-trideoxy-a-L-lyxo-hexopyranosyl)oxy]-7,8,9,10-tetrahydro-6,11-dihydroxy-8-hydroxyacetyl)-1-methoxy-5,12-naphthacenedione), Doxorubicin 11-O-β-D-galactopyranoside (8S-cis)-10-[3'-amino-4'-O-β-D-galactopyranosyl-2',3',6'-trideoxy-a-L-lyxohexopyranosyl)oxy]-7,8,9,10-tetrahydro-6,8-dihydroxy-8-hydroxyacetyl)-1-methoxy-5,12-naphthacenedione), Doxorubicin 4',6,8-tri-O-β-D-galactopyranoside (8S-cis)-10-[3'-amino-4'-O-β-D-galactopyranosyl-2',3',6'-trideoxy-a-L-lyxo-hexopyranosyl)oxy]-7,8,9,10-tetrahydro-6,8-di-O-β-D-galactopyranosyl 11-hydroxy-8-hydroxyacetyl)-1-methoxy-5,12-naphthacenedione), Doxorubicin 4',6,8,11-tetra-O-β-D-galactopyranoside (8S-cis)-10-[3'-amino-4'-O-β-D-galactopyranosyl-2',3',6'-trideoxy-a-L-lyxo-hexopyranosyl)oxy]-7,8,9,10-tetrahydro-6,8,11-tri-O-β-D-galactopyranosyl-8-hydroxyacetyl)-1-methoxy-5,12-naphthacenedione), Doxorubicin 4',6-di-O-β-D-galactopyranoside (8S-cis)-10-[3'-amino-4'-O-β-D-galactopyranosyl-2',3',6'-trideoxy-a-L-lyxo-hexopyranosyl)oxy]-7,8,9,10-tetrahydro-6-O-β-D-galactopyranosyl-8,11-dihydroxy-8-hydroxyacetyl)-1-methoxy-5,12-naphthacenedione), Doxorubicin 4',8-di-O-βD-galactopyranoside (8S-cis)-10-[3'-amino-4'-O-β-D-galactopyranosyl-2',3',6'-trideoxy-a-L-lyxo-hexopyranosyl)oxy]-7,8,9,10-tetrahydro-8-O-β-D-galactopyranosyl-6,11-dihydroxy-8-hydroxyacetyl)-1-methoxy-5,12-naphthacenedione), Resveratrol 4'-O-β-D-galactopyranoside, Resveratrol 3-O-β-D-galactopyranoside, Resveratrol 5-O-β-D-galactopyranoside, Resveratrol 4',3-di-O-β-D-galactopyranoside, Resveratrol 5,3-di-O-β-D-galactopyranoside, Resveratrol 5,4',3-tri-O-β-D-galactopyranoside, Phorbol 12-O-octanoyl-13-O-acetyl-6b-O-β-D-galactopyranoside, Phorbol 12-O-octanoyl-13-O-acetyl-4-O-β-D-galactopyranoside, Phorbol 12-O-octanoyl-13-O-acetyl-10-O-β-D-galactopyranoside, Phorbol 12-O-octanoyl-13-O-acetyl-4,6b-O-di-β-D-galactopyranoside, Phorbol 12-O-octanoyl-13-O-acetyl-4,10-di-O-β-D-galactopyranoside, Phorbol 12-O-octanoyl-13-O-acetyl-6b,10-di-O-β-D-galactopyranoside, Phorbol 12-O-octanoyl-13-O-acetyl-4,6b,10-tri-O-β-D-galactopyranoside, 1,2-di-O-octanoyl-3-O-β-D-galactopyranosyl-rac-glycerol, 4-O-(β-D-galactopyranosyl)phenyl retinamide, Mitoxantrone 2',2'-bis-di-O-β-D-galactopyranoside (1,4-dihydroxy-5,8-bis[2(2-O-β-D-galactopyranosylethyl)aminoethylamino]-9,10-anthracenedione), Thymidine 5'-O-β-D-galactopyranoside (1-(2'-deoxy-5'-O-β-D-galactopyranosyl-(β-D-ribofuranosyl)-5-methyluracil), 2'-O-(2,6-dibromo-4-cyano-phenyl)oxymethyl) D-Luciferin, myo-inositol β-D-galactoside, pantothenic acid di-β-D-galactoside, pyridoxal 5-O-β-D-galactoside, and pyridoxine β-D-galactoside.

2',3'-dideoxy-2',3'-didehydroadenosine 5'-O-galactopyranoside (d4A-Gal)

tryptophan-cephalosporanate

4-O-Methotrexate b-D-galactopyranoside

RGDS-Galactoside (Arginine-Glycine-Aspartic Acid-Serine-O-b-D-Galactopyranoside)

Swainsonine b-D-Galactopyranoside beta-oestradiol 2,17-di-O-b-D-galactopyranoside 12-Crown-42-O-b-D-galactopyranoside

B. Transfection of Cells

In the present invention, cells are transformed or transfected either in vivo or ex vivo with a recombinant expression vector capable of transforming the cells to express an enzyme such as those described in paragraph II.A., above. The term "transformant host cell" is intended to include prokaryotic and eukaryotic cells which have been transformed or transfected with a recombinant expression vector of the invention. The terms "transformed with", "transfected with", "transformation" and "transfection" are intended to encompass introduction of nucleic acid (e.g. a vector) into a cell by one of many possible techniques known in the art. Prokaryotic cells can be transformed with nucleic acid by, for example, electroporation or calcium-chloride mediated transformation. Nucleic acid can be introduced into mammalian cells via conventional techniques such as calcium phosphate or calcium chloride co-precipitation, DEAE-dextran-mediated transfection, lipofection, electroporation or microinjection. Suitable methods for transforming and transfecting host cells can be found in Sambrook et al. 1989, and other laboratory textbooks.

The nucleic acids of the present invention which encode enzymes having the appropriate activity as described in paragraph II.A., above, can be incorporated in a known manner into a recombinant expression vector to obtain the desired expression of the encoded enzyme. The recombinant expression vectors contain a nucleic acid or an oligonucleotide fragment thereof of the invention and a regulatory sequence, selected on the basis of the host cells to be used for expression, which is operatively linked to the nucleic acid or oligonucleotide fragment. Operatively linked is intended to mean that the nucleic acid is linked to a regulatory sequence in a manner which allows expression of the nucleic acid. Regulatory sequences are art-recognized and are selected to direct expression of the desired protein in an appropriate host cell. Accordingly, the regulatory sequence may be a promoter, enhancer or other expression control elements. Such regulatory sequences are known to those skilled in the art or one described in Goeddel, 1990, can be used. The expression vector may contain activatable promoter elements, inducible promoter systems, tissue or environment sensitive promoter systems, and-or other cis- or trans-acting factors effecting gene expression in vivo. It should be understood that the design of the expression vector may depend on such factors as the choice of the host cell to be transfected and/or the type of enzyme desired to be expressed.

The recombinant expression vectors of the invention can be designed for expression of encoded proteins in prokaryotic or eukaryotic cells. For example, proteins can be expressed in bacterial cells such as *E. coli*, insect cells (using baculovirus), yeast cells or mammalian cells. Other suitable host cells can be found in Goeddel, 1990. Expression in prokaryotes is most often carried out in *E. coli* with vectors containing constitutive or inducible promoters directing the expression of either fusion or non-fusion proteins. Examples of vectors for expression in yeast *S. cerivisae* include pYepSec1 (Baldari. et al., 1987), pMFa (Kurjan and Herskowitz, 1982), pjRY88 (Schultz et al., 1987), and pYES2 (Invitrogen Corporation, San Diego, Calif.). Baculovirus vectors available for expression of proteins in cultured insect cells (SF 9 cells) include the pAc series (Smith et al., 1983) and the pVL series (Lucklow, V. A., and Summers, M. D., 1989).

C. Animal Applications.

The pro-drugs of the present invention may be used to treat a variety of diseases, such as cancer, cystic fibrosis, chronic bacterial infection, viral infection, Duchenne's Muscular Dystrophy, arthritis, coronary artery disease, chronic pain or other genetic, autoimmune, proliferative or degenerative diseases. The pro-drugs also may be used in positive selection mechanisms.

Various cancers, such as human melanoma, human ovarian cancer, human neuroblastoma, human squamous cell carcinoma, human fibrosarcoma, human prostate cancer, and human pancreatic cancer, may be treated. For treating cancer, the pro-drug is a cytotoxic compound, such as doxorubicin, mitoxantrone, 5-fluorouridine, 5-fluorouracil, methotrexate, 4-hydroxyphenylretinamide, cyclohexamide, or cyclophosphamide, conjugated with a BLOCK. Preferably, a vector or retroviral vector that contains an enzyme selected to match the pro-drug used to transform either in vitro or in vivo tumor cells. The tumor cells may be central nervous system cells, lung cells, breast cells, ovary cells, liver cells, squamous cells, prostate cells, pancrease cells, or skin cells. Alternatively, cancer cells from an in vitro cultured tumor cell line may be transformed. If the cells are transformed in vitro, they may be irradiated so that they are viable but unable to replicate.

For treating cystic fibrosis, the pro-drug is preferably an immuno-modulating drug, such as 15-deoxyspergualin or an antibiotic, such as tobramycin, amiloride or colistine, conjugated with a BLOCK.

For treating chronic nerve pain (neuropathic pain), the pro-drug is preferably an analgesic drug such as an opiod (for example, dihydromorphine, oxycodone, 4'-hydroxyfentanil or buprenorphine), anticonvulsants (for example, carbamazepine, gabapentin or phenobarbital), tricyclic antidepressant (for example, desipramine or opipramol), or peptide (for example, Met-enkephalin) conjugated with a BLOCK.

The pro-drug could be used in conjunction with an unconjugated bioactive compound wherein the activation of the pro-drug in the transgenic cells reduces or eliminates the effect of the unconjugated bioactive compound.

The pro-drugs of the invention can be administered using conventional modes of administration including, but not limited to, intravenous, intraperitoneal, oral, intralymphatic, intramuscular, or administration directly into the tumor. Intravenous administration is preferred.

The pro-drugs of the invention may be in a variety of dosage forms which include, but are not limited to, liquid solutions or suspensions, tablets, pills, powders, suppositories, polymeric microcapsules or microvesicles, liposomes, and injectable or infusible solutions. The preferred form depends upon the mode of administration and the therapeutic application. For example, oral administration of the B-lactamase conjugates may be disfavored because the conjugates tend to be degraded in the stomach if taken orally, e.g., in tablet form.

The pro-drugs also preferably include conventional pharmaceutically acceptable carriers and adjuvants known in the art such as human serum albumin, ion exchangers, alumina, lecithin, buffer substances such as phosphates, glycine, sorbic acid, potassium sorbate, and salts or electrolytes such as protamine sulfate.

The most effective mode of administration and dosage regimen for the compositions of this invention depends upon the severity and course of the disease, the patient's health and response to treatment and the judgment of the treating physician. Accordingly, the dosages of the immunoconjugates and pro-drugs should be titrated to the individual patient. Methods of determining dosages are well known in the art.

Nevertheless, an effective dose of the pro-drugs of this invention may be in the range of from about 1.0 to about 1000 mg/Kg/day, the dose of the pro-drug depending upon the particular pro-drug used and the parent bioactive compound from which it is derived. Since the pro-drug is less cytotoxic than the parent bioactive compound, dosages in excess of those recognized in the art for the parent bioactive compound may be used.

C. Plant Applications.

The pro-drugs of the present invention may be used to affect plant growth and development. For example, conjugates of herbicides, growth regulators or protein glycosylation inhibitors may provided to recombinant plant or bacterial species to affect selective death of recombinant plants without affecting growth of wild-type plants. These conjugates can be derivatives of common herbicides, including but not limited to maleic hydrazide, bromoxynil, atrazine or the like.

In a particular embodiment, the bioactive compound is selected from the group consisting of plant phytohormones such as gibberellic acid (gibb-3-ene-1,10-dicarboxylic acid, 2,4a,7-trihydroxy-1-methyl-8-methylene-1,4a-lactone), genistein or coumestrol, cytokinins such as zeatin, kinetin, 6-isopentenylaminopurine or abscisic acid (ABA), auxins such as indolacetic acid (IAA), oligosaccharins such as xyloglucan or oligogalacturonide and brassinosteroids such as brassinolide, 20-hydroxyecdysone, jasmonic acid, typhasterol or castasterone, and herbicides such as maleic hydrazide, bromoxynil, cycloheximide, chloramphenicol, 2,4-dichlorophenoxy)acetic acid (2,4-D), atrazine, and glyphosate.

In a particular embodiment, the bioactive compound is an herbicide, including but not limited to 4-(2,4-dichlorophenoxy)butyric acid, 4-chloro-o-tolyloxyacetic acid, acifluorfen, alachlor, amitrole, atrazine, bentazon, bentazone, carfentrazone-ethyl, chlorimuron, clethodim, clomazone, clopyralid, cloransulam methyl, dicamba, dimethenamid, ethalfluralin, fenoxaprop-P-ethyl, fluazifop, flufenacet, flumetsulam, flumiclorac, fomesafen, fosamine, imazamox, imazaquin, imazethapyr, lactofen, linuron, metolochlor, metribuzin, norflurazon, paraquat, pendimethalin, picloram, potassium (RS)-2-(2-methyl-4-chlorophenoxy)propionate, primisulfuron, prometon, quizalofop-P-ethyl, sethoxydim, s-metolachlor, sullfentrazone, thifensulfuron, thiophanate-methyl, triclopyr, trifluralin.

Similarly, plant growth and development of recombinant plants may be affected by providing conjugates of growth regulators including 20-hydroxyecdysone, gibberellins, absicic acids, or the like, or by providing conjugates of glycosylation inhibitors including deoxynojirimycin, deoxymannonojirimycin, swainsonine, or like compounds.

In a particular embodiment, the bioactive compound is a plant growth regulator, including but not limited to 20-hydroxyecdysone, gibberellin (Gibb-3-ene-1,10-dicarboxylic acid, 2,4a,7-trihydroxy-1-methyl-8-methylene-, 1,4a-lactone), Cytokinins (such as zeatin, kinetin, 6-isopentenylaminopurine), Abscisic acid, Auxins, oligosaccharins and brassinosteroids.

In a particular embodiment, any of such conjugates can be delivered to the plant or bacterial species as their beta-glucopyranosiduronic acid derivatives, or as the methyl ester or triacetyl, methylester glucuronides. In a preferred embodiment of the invention, the glucuronide conjugates will contain either one or more acetate or ester groups, that lend the conjugates more permeant to cell membranes and aide in cell, tissue or plant uptake and utilization. Intracellular esterase or lipase enzyme activity of plants or bacteria so treated will lend these conjugates effective through enzymatic removal of the aforementioned acetate or ester permeabilizing groups, and thereby release the parent glucuronides more efficiently intracellularly.

In another embodiment of the present invention, the use of tissue-specific or environmentally sensitive promoter elements are used in controlling the expression of the cloned enzyme gene, and thereby control the release of the bioconjugates for activity in specific tissues of the plant or organism, or allow for environmental control of bioactive compound release. An example of such an embodiment includes the use of elements that express the cloned enzyme only in floral tissues, thus causing selective cell death only in the flowers of the recombinant plant, effectively sterilizing the plant.

Without being bound by theory, one of skill in the art would readily understand that different combinations of marker genes and bioactive compounds may be employed in practicing the present invention. For example, marker genes that have been employed in plant systems include, but are not limited to NAN (N-Acetyl Neuraminidase, Sialidase), sXynA (Xylanase), GUS (β-Glucuronidase), luc (luciferase), GFP (Green Fluorescent Protein), EGFP (Enhanced Green Fluorescent Protein), NPTII (neomycin phosphotransferase), and CAT (chloramphenicol acetyltransferase). Accordingly, one of skill in the art would recognize that any of such genes may be used in practicing the present invention.

For example, one of skill in the art may require a means to selectively terminate transformed potato plants. Transgenic potatoes could be produced that contain the GUS gene, as well as other genes of interest to the researcher using methods known to those of skill in the art. Confirmation of the successful transformation of the GUS gene into the plant could be performed by extracting total DNA from plant tissues and using the DNA as a template for PCR amplification with primers which amplify the region from a GUS gene fragment. Separation of the PCR product and observing that a band of the predicted size is present confirms that the gene has been introduced into plant. Similarly, expression of the GUS gene in plant tissues and whole plants can be confirmed using the MarkerGene™ β-Glucuronidase (GUS) Reporter Gene Activity Detection Kit and protocol therein.

When the researcher determines that selective destruction of the transformed plants is required, an appropriate conjugate of a bioactive compound such as an herbicide may be applied to the plants, such as by spray application or application to the soil, causing selective ablation of GUS-positive plants without affecting the growth or morphology of wild-type plants. One of skill in the art would further recognize that such a method could be used to affect the selective enhancement of transformed plants, such as the application of conjugates of growth regulating compounds, thus causing selective growth of GUS-positive plants without affecting the growth or morphology of wild-type plants.

In order that the invention described herein may be more fully understood, the following examples are set forth. It should be understood that these examples are for illustrative purposes only and are not to be construed as limiting the scope of the invention in any manner.

III. Examples

Example 1

Preparation of a Cycloheximide Galactoside Conjugate

The following compound was prepared:

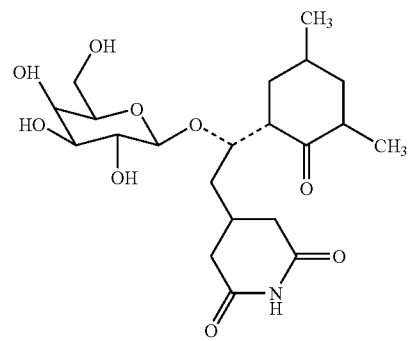 [SMILES: CC1CC(C)C(=O)[C@H]([C@H](CC2CC(=O)NC(=O)C2)OC2OC(CO)C(O)C(O)C2O)C1]

Cycloheximide-galactoside (M0147). An enzymatic method of synthesis was used to produce the β-D-galactoside of cycloheximide (3-[2-(3,5-dimethyl-2-oxocyclohexyl)-2-O-(β-D-galactopyranosyl)ethyl]glutarimide). Enzymatic galactosylation was carried out using a modification of the procedure of Wong, et al. (1991). Actidione (cycloheximide, 72 mg, 0.256 mmole) and ortho-nitrophenyl β-D-galactopyranoside (132 mg, 0.438 mmole) were dissolved in 0.10 M $Na_2HPO_4$/10 mM $MgCl_2$ buffer (pH 7.0, 4 mL) and Tris buffer (pH 7.3, 1 mL) with warming. To this solution was added E. coli B-Galactosidase (172 U, 344 µL of a 500 U/mL solution in D.I. water). This mixture was allowed to react at 23° C., for 49 hours until t.l.c. analysis showed production of a lower Rf product (Rf 0.18, 7:3 ethylacetate:methanol irrigant). The reaction mixture was heated to 92° C. to destroy the enzyme, lyopholized to a white powder, and chromatographed (silica gel 60 Å, 25 g) using 0-30% ethylacetate in methanol as eluent. The first major product eluting from the column was combined and evaporated to a white powder (60 mg, 50%). 1-H-n.m.r. ($D_2O$) was consistent with the proposed structure.

Example 2

Preparation of a Dexamethasone Galactoside Conjugate

The following compound was prepared:

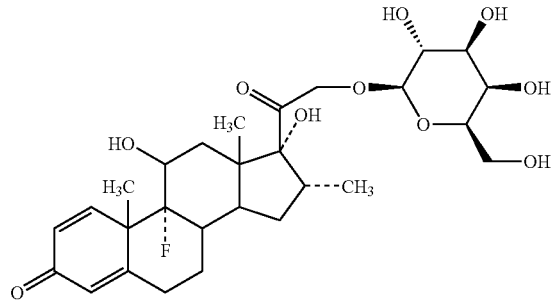

Dexamethasone β-D-galactopyranoside (M0149) (21-O-β-D-galactopyranosyl-9-fluoro-11,17-dihydroxy-16-methylpregna-1,4-diene-3,20-dione) was prepared from the parent steroid by treatment with silver triflate/sym-collidine, 3 Å molecular sieves and acetobromogalactose in dichloromethane:acetonitrile (2:1) under anhydrous conditions in the dark for 20 hours. The fully protected glycoside (M0146) was isolated in 39% yield as the major isomer, which upon deblocking using catalytic sodium methoxide/methanol gave the title compound, in quantitative yield.

Example 3

Preparation of a Hydroxymethylpsoralen Galactoside Conjugate

The following compound was prepared:

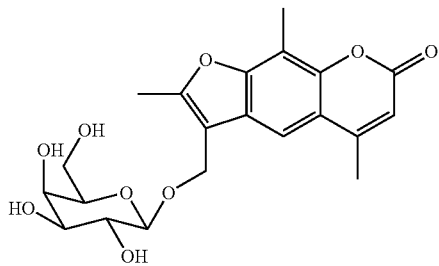 [SMILES: Cc1oc2c(C)c3oc(=O)cc(C)c3cc2c1COC1OC(CO)C(O)C(O)C1O]

4'-Hydroxymethyl-trimethylpsoralen was prepared using a modification of the procedure of Isaacs, et al. (Isaacs, S. T., et al., 1977). Under dry conditions, trimethylpsoralen (100 mg, 0.438 mmole) was dissolved in acetic acid (glacial, 10 mL) with heating, cooled to room temperature and chloromethylethylether (0.935 mL, 10 mmole) added with stirring. This mixture was allowed to stir at room-temperature, protected from light, in a sealed flask for 15 hours, after which time additional chloromethylethylether (1.0 mL, 10.8 mmole) was added and the reaction continued until t.l.c. analysis (9:1 chloroform:methanol) showed conversion of the starting material to a lower Rf, blue fluorescent product (Rf 0.92 to 0.68). The reaction mixture was cooled to 0° C. (ice-bath), filtered, and the filtrate evaporated to a white powder, which was suspended in distilled water (50 mL) and heated to reflux (3 hours), cooled, and the white precipitate filtered, washed with a minimum ice-cold water, and dried in air. Yield 91 mg (75% of theoretical yield) $^1$H-n.m.r. (CDCl$_3$): d 2.5-2.6 (9H, m, 3×—CH$_3$), 4.8 (2H, s, —CH$_2$OH), 6.2 (1H, s, H-3), 7.8 (1H, s, H-5).

4'-hydroxymethyl-trimethylpsoralen (44 mg, 0.17 mmole) was dried in vacuo, dissolved in anhydrous dichloromethane (20 mL) and placed under a dry nitrogen atmosphere. To this solution was added 3 Å molecular sieve (0.5 g), acetobromogalactose (140 mg, 0.34 mmole), silver trifluoromethanesulfonate (90 mg, 0.34 mmole)) and sym-collidine (45 µL, 0.34 mmole). This mixture was allowed to stir in the dark at room temperature for 18 hours, filtered through a Celite™ pad, the percipitate washed with excess chloroform, and the combined filtrates extracted with water, 1N aqueous HCl solution, 2% ammonium hydroxide solution, saturated aqueous sodium bicarbonate solution and water (1×50 mL each). The final organic layer was dried over anhydrous sodium sulfate, evaporated and dried to a white powder, which was subjected to column chromatography (silica gel 60 Å, 25 grams) using a gradient elution with 0-50% ethylacetate in chloroform as eluent. The first product eluting from the column was combined, evaporated and dried in vacuo to give 68 mg (68% of theoretical yield) white powder. $^1$H-n.m.r. (CDCl$_3$) d: 1.4 (12H, 4s, OCOCH$_3$×4), 2.4-2.5 (9H, 3s, —CH$_3$×3), 4.0-4.3 (6H, m, ring protons), 5.0 (2H, m, CH$_2$O—), 5.2 (1H, d, anomeric H), 6.1 (1H, d, H-3), 7.3 (1H, s, H-5).

This dried per-acetate derivative was suspended in anhydrous methanol (30 mL) and toluene (2 mL) and 25% (w/v) NaOMe/MeOH (200 µL) was added, and this mixture allowed to stir in the dark, under anhydrous conditions for 15 hours. The reaction mixture was neutralized with washed, dry IRC50(H+) resin, filtered, and the resin washed with dry methanol. The combined filtrates were evaporated and dried in vacuo to give 41 mg of an off white solid (84% of theoretical yield).

Example 4

Loss of Biological Activity of 5-Fluorouridine (5FUR) Upon Galactoside Conjugation. Bacterial Growth Assay E. coli strains CSH23/S90C and CSH22/S90C were tested with 5-fluorouridine (5FUR) and the 5FUR-galactoside conjugate described in Example 16, 5-fluorouridine-5'-O-β-D-galactopyranoside, (M0174) to confirm loss of biological activity upon conjugation. CSH23 is a strain inducible for lacZ expression; CSH22 is a deletion mutant for lacZ and is therefore uninducible. Other strains with these properties are commercially available. When grown under non-inducing conditions, neither strain will produce β-galactosidase. Each strain was innoculated into 10 mL M9 minimal media and grown in non-inducing conditions, shaking at 37° C. overnight. Overnight cultures (500 µL) were transferred into 10 µL fresh M9 media and grown to logarithmic phase for 4 hours prior to beginning the experiments. 1 mL of this culture was transferred to 10 ml fresh M9 media containing 10 µg/ml 5FUR, 16.2 µg/ml M0174, or no additions, and returned to the incubator. Growth curves were generated by removing aliquots of each culture at 30 minute intervals and reading absorbance at 420 nm. All final data was run in duplicate trials. As shown in FIG. 1, unmodified 5FUR caused a significant decrease in growth, while the galactoside pro-drug had very little effect, demonstrating loss of biological activity of the compound upon conjugation.

Example 5

Figure 2:
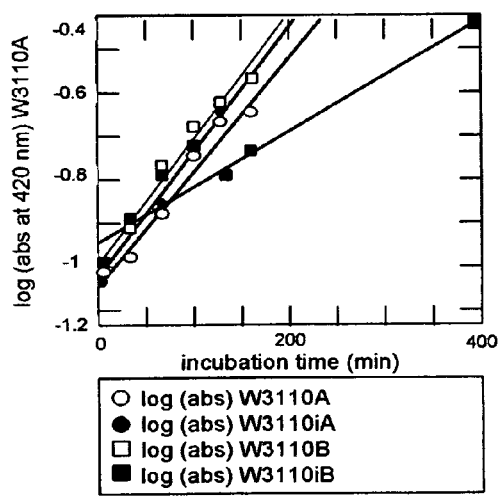
FIG. 2 shows growth plots of two *E. coli* strains, W3110 and CSH36 grown in the presence of ONPG. Duplicate trials (A and B) were run. W3110 was grown with (W3110i) and without (W3110) the addition of INTG.

Induction of Gene Expression for Control of Pro-Drug Release. Response of CSH36 and W3110 E. Coli Bacteria to ONPG Application with or without Induction by IPTG E. coli strains CSH36 and W3110 available from the ATCC, Manassas, Va. were tested with orthonitrophenyl β-D-galactopyranoside (ONPG), according to the procedure of Marsh, 1994, to confirm release of compound upon induction of β-galactosidase production. W3110 is a wild-type E. coli strain inducible for lacZ expression; CSH36 is a constitutive mutant for lacZ and therefore produces β-galactosidase regardless of induction conditions. Each strain was innoculated into 10 mL M9 minimal media and grown in non-inducing conditions, shaking at 37° C. overnight. W3110 was also innoculated into 10 mL M9 media containing 0.3 mM iso-propyl thiogalactoside (IPTG) (W3110i) to induce β-galactosidase production. Overnight cultures (500 µL) were transferred into 10 mL fresh M9 media (+/−IPTG) and grown to logarithmic phase for 4 hours prior to beginning the experiments. 1 mL of this culture was transferred to 10 ml fresh M9 media (+/−IPTG) containing 0.3 mg/ml ONPG or no additions, and returned to the incubator. Growth curves were generated by removing aliquots of each culture at 30 minute intervals and reading absorbance at 420 nm. All final data was run in duplicate trials (A and B). CSH36 and induced W3110 showed turnover of ONPG to ONP by the development of a yellow color in the media, as ONPG is a colorless compound and ONP is yellow. ONP is also toxic to the bacteria, and therefore growth was retarded in those cultures producing β-galactosidase and turning over ONPG to ONP (see below and FIG. 2).

| Strain | IPTG | ONPG | Doubling Time (min) |
|---|---|---|---|
| W3110 | no | no | 98 |
| W3110 | yes | no | 88 |
| W3110 | no | yes | 92 |
| W3110 | yes | yes | 215 |
| CSH36 | no | no | 89 |
| CSH36 | no | yes | *not measurable |

*growth halted approximately 2 hours after start of experiments

Example 6

Regulating Sugar Content of Media to Effect Differential Growth of CREBAG2 Cells Vs. NIH/3T3 Cells Mouse fibroblast cell line NIH/3T3 and its β-galactosidase expressing derivative CREBAG 2 available from ATCC, Manassas, Va., were grown in media containing either only glucose or only lactose to show the ability to select for β-galactosidase expressing cells by providing only lactose as a carbon source, which must be cleaved into glucose and galactose by β-galactosidase before it can be utilized by the cell.

1:1 Dulbecco's Modified Eagles medium (DME): Ham F12 medium was prepared according to standard formula (Freshney) and with the omission of D-glucose, which was replaced by an equimolar quantity of D-lactose. Cell lines were plated in 2, 12 well plates for each cell type, at a density of $5 \times 10^3$ cells per well, in DME containing 10% Calf Serum (CS), and incubated for 4 hours at 37° C. to allow settling and attachment to the plate. Media was then removed and cells were washed once with phosphate buffered saline solution (PBS). The wells were then filled with the different test medias, including DME:F12 containing glucose and 10% CS (positive control), DME:F12 containing glucose and 10% dialyzed CS (dCS), DME:F12 containing lactose and 10% dCS, and DME:F12 containing no sugar and 10% dCS (negative control). Dialyzed calf serum was used in place of regular calf serum in the test medias because of the unknown sugar content of the serum. Cells were grown in test medias at 37° C. in 5% $CO_2$ atmosphere for four days. The MTT assay was performed on one set of plates after two and four days growth to estimate the number of cells and assay growth rates as described in Example 7, below. Doubling times of cells grown in DME:F12 with 10% dCS and either glucose, lactose, or no sugar are listed below. NIH/3T3 cells grown in lactose showed a doubling time closer to that of cells grown in no sugar than that of cells grown in glucose. CRE BAG 2 cells grown in lactose, however, showed a doubling time very close to cells grown in glucose, showing the ability to select for lacZ cells.

Doubling Times (Days) of Cells Grown in DME:F12 with 10% dCS

| Cell type | no sugar | +glucose | +lactose |
|---|---|---|---|
| NIH/3T3 | 1.09 | 0.57 | 0.87 |
| CRE BAG 2 | 1.35 | 1.10 | 1.13 |

Example 7

In Vitro Response of CREBAG2 and NIH/3T3 Cells to 5FUR-Gal (M0174) Cell Proliferation Assay Mouse fibroblast cell line NIH/3T3 and its β-galactosidase expressing derivative CREBAG 2 are plated in 12 well plates at a concentration of $12 \times 10^4$ cells per well and allowed to grow overnight at 37° C., 10% $CO_2$. Cells are then exposed to various concentrations of M0174 for two hours per day for three days, after which cell proliferation is measured by the MTT assay. Control wells receive only appropriate amounts of solvent used to administer M0174.

For the MTT assay, cells are incubated with the MTT reagent, which is turned over by live cells to a purple MTT formazan product. Turnover is directly proportional to the number of live cells, enabling a proportional measurement of the number of cells to be achieved by measuring the production of MTT formazan. Media is removed from cells in the twelve well plate and replaced with DME containing 10 mM Hepes. 0.25 mL of a 2 mg/ml solution of MTT is then added to each well, and plates are covered and wrapped with aluminum foil and incubated at 37° C. for three hours. Plates are then emptied of the media MTT solution, and 1 mL of DMSO and 125 μL of Sorensens glycine buffer are added to each well to solubilize the MTT formazan product. Absorbence of each sample is measured against a DMSO blank at 570 nm.

Growth of cells tested with M0174 are expressed as a percentage of the growth in control wells (absorbence of test well absorbence of control well).

Example 8

In Vitro Response to 5-FUR-Galactoside Conjugate of PC5 Tumor Cells with and without Retroviral Transfection with lacZ The PC5 cell line is a model cell line for prostrate tumor cells, and can be transformed with a retroviral vector to produce new cell lines stably expressing β-galactosidase. Viral vector containing the lacZ gene and the Neomycin resistance gene (conferring resistance to the selection agent Gentamycin (G418)) is collected in the media from confluent packaging cells producing the virus and filtered through a 0.45 μm membrane to remove cellular debris. The viral solution is then added to the media of PC5 cells and incubated overnight. The cells are then split into media containing the selection agent G418 to select for transformants. After 1-2 weeks of G418 selection, the remaining cells are plated in 96 well plates to isolate single cells, and allowed to grow until colonies were several hundred cells. A duplicate plate was created and colonies were tested for β-Gal expression by X-gal staining. Colonies with consistent high levels of expression throughout all cells were chosen for further experiments (PC5βGal cells).

PC5 and PC5βGal cells are plated in 12 well plates at a concentration of 12×10⁴ cells per well and allowed to grow overnight at 37° C., 10% $CO_2$. Cells are then exposed to various concentrations of the 5FUR-galactoside conjugate described in Example 16, 5-fluorouridine-5'-O-β-D-galactopyranoside (M0174) for two hours per day for three days, after which cell proliferation is measured by the MTT assay. Control wells receive only appropriate amounts of solvent used to administer M0174.

Growth of cells tested with M0174 are expressed as a percentage of the growth in control wells (absorbence of test well absorbence of control well).

Example 9

In Vitro Response to 5-Fluorouridine-5'-O-β-D-Galactopyranoside of D5 Tumor Cells with or without Lipofection with lacZ Vector Lipofection of D5 murine melanoma cells with the pCMVβ plasmid containing the lacZ gene provided a lacZ positive set of cells with transient but high levels of β-galactosidase expression. A 60 mm plate of D5 cells, 80% confluent, was lipofected for 5 hours with 3.6 µg/ml pCMVB (a plasmid containing the lacZ gene)(CLONTECH) using 36 µL lipofectAmine reagent (Life Technologies, Gibco BRL). After lipofection, fresh media was added to the cells to dilute the lipofection reagent, and cells were grown for 2 days. A cover slip of the lipofected D5 cells was stained with X-gal and transfection efficiency was estimated at 70%. D5 and lipofected D5 cells were plated in 12 well plates at a density of 12×10³ cells per well and incubated 6 hours. The 5FUR-galactoside conjugate described in Example 16, 5-fluorouridine-5'-O-β-D-galactopyranoside (M0174) was added to cells at various concentrations and cells were incubated 6 hours, after which the media was changed. Cells were allowed to grow another 36 hours, then the MTT assay was performed to estimate the number of living cells per well. Cell numbers were expressed as a percent of the number of cells in the control well. All assay points were performed in duplicate and averaged. Administration of M0174 to both lipofected and control D5 cells in culture exhibited excellent differential growth curves with classic dose-response behavior. Lipofected D5 cells, because of lacZ expression, activated the M0174 pro-drug and were growth inhibited. Non-lipofected cells were unaffected by M0174 treatment, even at high dosage values.

| 5FURG (NIH174, ug/ml) | D5 lipofected, % of control growth | D5 % of control growth |
|---|---|---|
| 0.00000 | 100.00000 | 100.00000 |
| 0.30000 | 47.97373 | 109.89583 |
| 5.00000 | 22.02627 | 87.94271 |

Example 10

The In Vivo Response to 5-Fluorouridine-5'-O-β-D-Galactopyranoside Treatment of D5 Tumor Cells (Lipofected with a lacZ Containing Vector) in Mice The 5FUR-galactoside conjugate described in Example 16, 5-fluorouridine-5'-O-β-D-galactopyranoside (M0174) was tested to determine the reduction of tumor growth of subcutaneously implanted D5 mouse melanoma tumors that had been lipofected with a vector containing the lacZ marker gene in mice. This data is shown below. C57/J(B6) mice (22-36 g each) were injected in the right flank with 50 µL HBBS containing 1×10⁶D5 tumor cell that were either untreated or lipofected with a vector containing the lacZ gene. M0174 was administered intraperitoneally starting at Day 3, for 4 days, to mice that had received lipofected tumor cells in doses of either 25 or 50 mg/kg/day, and to mice that had received untreated tumor cells in doses of 100 mg/kg/day. Measurement of tumor area in $mm^2$ began on Day 8 and ended on Day 26. The results clearly show a slight delay in tumor growth at both 25 and 50 mg/Kg/Day groups of mice receiving lipofected tumor cells (5-7 animals/group), indicating drug-targeting in vivo by β-galactosidase expressing cells. NO EFFECT (i.e. no significant drug release) for pro-drug on non-lipofected cells was found (even at 100 mg/Kg/Day), indicating once again a lack of biological activity for the pro-drug, M0174. These results show efficacy of pro-drug delivery and efficacy in vivo, confirming our in vitro results.

Example 11

Selection of β-Gal Expressing *E. Coli* Cells from Co-Culture by Treatment with a Galactoside Pro-Drug

*E. coli* strains CSH36/S90C and CSH22/S90C were grown in co-culture and tested with the chloramphenicol galactoside pro-drug (M0165) described in Example 15, to show lack of translocation of drug released in β-galactosidase expressing cells to other cells in the culture, and therefore selection for the lacZ-cells. CSH36 is a constitutive mutant for lacZ and therefore produces β-galactosidase regardless of induction conditions. CSH22 is a deletion mutant for lacZ and is therefore uninducible. Each strain individually and both strains together were innoculated into 10 mL aliquots of M9 minimal media and grown shaking at 37° C. overnight. Overnight cultures (500 µL) were transferred into 10 mL fresh M9 media and grown to logarithmic phase for 4 hours prior to beginning the experiments. 1 mL of this culture was transferred to 10 ml fresh M9 media containing 30 µg/ml chloramphenicol, 42 µg/ml M0165, or no additions, and returned to the incubator. Growth curves were generated by removing aliquots of each culture at 30 minute intervals and reading absorbance at 420 nm. Remaining portions of the cultures were allowed to grow overnight, and final absorbance readings were taken. Serial dilutions of cultures were made in M9 media and plated on M9 plates containing X-gal. Plates were incubated at 37° C. for 48 hours, then evaluated for growth of white (indicating lacZ –, CSH22 cells) and blue (indicating lacZ +, CSH 36 cells) colonies. Co-cultures grown overnight in the presence of either chloramphenicol showed no growth of either cell type, whereas co-cultures grown in the presence of MO165 showed growth of only CSH22 cells, demonstrating selection of the lacZ– cell type. This indicates that chloramphenicol was released from M0165 and localized to only the cells expressing β-galactosidase.

Example 12

Translocation of a Galactoside Pro-Drug in E. Coli. Creating a "Bystander" Effect by Using β-Galactosidase Expressing Cells E. coli strains CSH36/S90C and CSH22/S90C were grown in co-culture and tested with the 5FUR-galactoside conjugate described in Example 16, 5-fluorouridine-5'-O-β-D-galactopyranoside, (M0174) to show translocation of drug released in β-Gal expressing cells to other cells in the culture. CSH36 is a constitutive mutant for lacZ and therefore produces β-galactosidase regardless of induction conditions. CSH22 is a deletion mutant for lacZ and is therefore uninducible. Each strain individually and both strains together were innoculated into 10 mL aliquots of M9 minimal media and grown shaking at 37° C. overnight. Overnight cultures (500 μL) were transferred into 10 mL fresh M9 media and grown to logarithmic phase for 4 hours prior to beginning the experiments. 1 mL of this culture was transferred to 10 ml fresh M9 media containing 10 μg/ml 5-fluorouridine (5FUR), 16.2 μg/ml M0174, or no additions, and returned to the incubator. Growth curves were generated by removing aliquots of each culture at 30 minute intervals and reading absorbance at 420 nm. Remaining portions of these cultures were allowed to grow overnight, and final absorbance readings were taken. Serial dilutions of cultures were made in M9 media and plated on M9 plates containing X-gal. Plates were incubated at 37° C. for 48 hours, then evaluated for growth of white (indicating lacZ −, CSH22 cells) and blue (indicating lacZ+, CSH36 cells) colonies. As indicated in the table below, co-cultures grown overnight in the presence of either 5FUR or M0174 showed no growth of either cell type, indicating translocation of the released drug from the lacZ+CSH36 cells through the media to the lacZ− CHS22 cells.

| Strain | | Drug Added | | Colony Growth | |
|---|---|---|---|---|---|
| CSH36 | CSH22 | 5FUR | M0174 | blue | white |
| X | | | | X | |
| X | | X | | | |
| X | | | X | | |
| | X | | | | X |
| | X | X | | | |
| | X | | X | | X |
| X | X | | | X | X |
| X | X | X | | | |
| X | X | | X | | |

Example 13

Use of Phorbol Octanoyl Acetate Galactoside or Di-Octanoyl RAC-Glycerol Galactoside for Selective Growth Enhancement of Recombinant Mammalian Cells To test whether the application of growth stimulatory conjugates to recombinant cells can selectively enhance growth with respect to non-transformed cells, Swiss 3T3 cells available from ATCC, Manassas, Va., are transformed by lipofection with the pCMVβ plasmid containing the lacZ gene provided a lacZ positive set of cells with transient but high levels of β-galactosidase expression. A 60 mm plate of Swiss 3T3 cells, 80% confluent, is lipofected for 5 hours with 3.6 μg/ml pCMVB (a plasmid containing the lacZ gene) (CLONTECH) using 36 μL lipofectAmine reagent (Life Technologies, Gibco BRL). After lipofection, fresh media is added to the cells to dilute the lipofection reagent, and cells are grown in a $CO_2$-incubator environment (37° C.) for 2 days. A cover slip of the lipofected Swiss 3T3 cells is stained with X-gal and transfection efficiency is estimated. Swiss 3T3 and lipofected Swiss 3T3 cells are plated in 12 well plates at a density of $12 \times 10^3$ cells per well in DME/Waymouth media containing 2.5% FCS and incubated 6 hours. Phorbol Octanoyl Acetate Galactoside (150 ng/mL) or Di-Octanoyl rac-Glycerol Galactoside (40 μg/mL) are added to one-half of the wells, POA (100 ng/mL) or DOG (30 μg/mL) to one-eighth of the wells each, and to the remaining wells, no addition (controls). The cells are returned to the incubator and allowed to grow for 6 days as above. Differential growth of the recombinant Swiss 3T3 cells versus non-transformed cells is recorded by measuring the number of cells using the MTT assay (Plumb, et al., 1989).

Example 14

Use of Cycloheximide Galactoside (M0147) to Selectively Ablate β-Galactosidase Expressing CREBAG2 Cells in Co-Culture With NIH/3T3 Cells NIH/3T3, CRE BAG 2, or a 50/50 mixture of both cell lines (in co-culture) (Total cell density=$6 \times 10^4$ cells each) were plated in 60 mM plates. 12 tissue culture treated glass cover slips were added to each plate, and the cells were allowed to grow in an humidified $CO_2$-incubator (37° C.) for 24 hours. Half the cover slips from each plate were then transferred to separate plates. Cells were treated with 15 μg/ml cycloheximide ♭-D-galactopyranoside described in Example 1 (M0147) in media for 14 hours then given fresh media (DME with 10% FCS) for 10 hours. This treatment was repeated twice more, the cover slips were removed from both the M0147 treated and untreated 60 mm plates and placed in 12 well plates. To give an indication of the number of β-galactosidase expressing CREBAG2 cells remaining on the cover slips, the cover slips were incubated with the β-galactosidase substrate ONPG, whose turnover can be measured by the change in absorbance at 420 nm. The cells were rinsed with PBS, then 1 ml of 3.5 mM ONPG in HBSS was added to each well. After 4 hours incubation at 37° C., the solution was removed from each well and the absorbance was measured at 420 nm. Treatment of co-cultured CREBAG2 and NIH/3T3 cells with M0147 resulted in a decrease of β-galactosidase activity (and therefore the number of CREBAG2 cells) to nearly that of NIH/3T3 cells alone, indicating turnover of the pro-drug in CREBAG2 cells resulting in their selective ablation.

| | Growth (abs @ 420 nm) | |
|---|---|---|
| | NIH 147 treatment | Control |
| CRE BAG 2 | .450 | .561 |
| NIH/3T3 | .100 | .102 |
| Coculture | .133 | .543 |

Example 15

Preparation of a Chloramphenicol Galactoside Conjugate

The following compound was prepared:

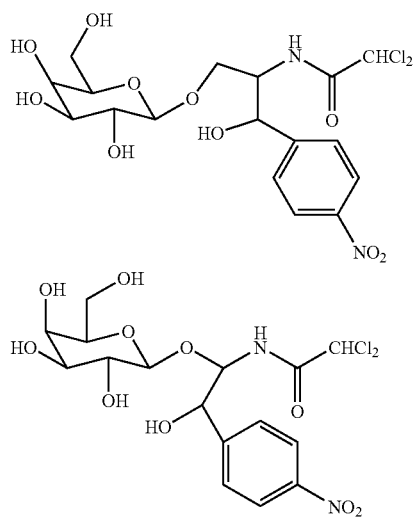

Chloroamphenicol (5.00 g, 15.475 mmole) was dissolved in anhydrous dichloromethane (35 mL) containing 3 Å molecular sieves, and placed under an atmosphere of dry nitrogen gas. To this solution was added acetobromogalactose (7.00 g, 17.02 mmole), anhydrous silver trifluoromethanesulfonate (4.38 g, 17.02 mmole) and sym-collidine (2.25 mL, 17.02 mmole). This mixture was allowed to stir under anhydrous conditions, in the dark, for 72 hours. Anhydrous acetonitrile (20 mL) was added to the flask, and stirring continued as above for 5 hours. The reaction was filtered through a pad of diatomaceous earth (Celite™-545) and the precipitate washed with chloroform (5×30 mL). The combined filtrates were extracted with water, 1 N hydrochloric acid, saturated aqueous sodium bicarbonate solution, 2% ammonium hydroxide solution, and 5% saturated brine solution (1×50 mL each). The resulting organic layer was dried over anhydrous sodium sulfate, filtered, evaporated and applied to a column of silicagel 60 Å (70-230 mesh, 250 g) using chloroform as solvent. The column was eluted by gradient elution from 0% to 4% methanol in chloroform. Fractions of the second major product to elute from the column were combined and evaporated to give the pure protected glycoside (M0160). A 500 mg sample of this material was dissolved in methanol:water (5:1, 60 mL) containing potassium cyanide (88 mg, 1.35 mmole), and this mixture allowed to stir at room temperature for 18 hours at room temperature. The reaction mixture was evaporated to approximately 10 mL, co-evaporated with methanol (4×10 mL), never allowing the sample to dry completely. The final sample was dissolved in 10 mL methanol, and dried onto diatomaceous earth (Celite™-545) (2 grams). This sample was applied to a column of silicagel 60 Å (70-230 mesh, 50 g) and eluted with 9:1 chloroform:methanol as eluent. Fractions of the first major product to elute from the column were combined and evaporated to approximately 5 mL, and crystallized by addition of petroleum ether (b.p.=35-60° C.) (100 mL). The white crystalline material obtained was dried in vacuo (111 mg, 30%). T.l.c. (SiO$_2$, irrigant=8:2 chloroform:methanol) Rf=0.38, $^1$H-n.m.r. (D$_2$O) d: 8.2 (d, 2H, Ph-H), 7.6 (d, 2H, Ph-H), 6.2 (s, 1H, CHCl$_2$), 5.2 (d, 1H, Ph-CH(OH)), 4.4 (t, 2H, —CH$_2$—), 4.2 (dd, 1H), 3.9 (d, 1H, H-1), 3.8-3.5 (m, 6H, ring protons).

Example 16

Preparation of a 5-Fluorouridine-5'-O-β-D-Galactoside Conjugate

The following compound was prepared:

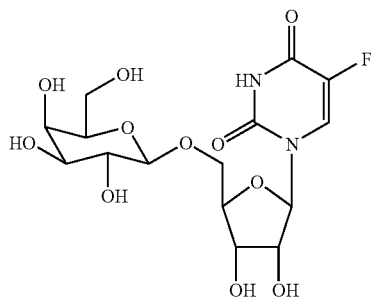 [SMILES: O=c1[nH]c(=O)n(C2OC(COC3OC(CO)C(O)C(O)C3O)C(O)C2O)cc1F]

5-Fluorouridine-5'-O-β-D-Galactopyranoside (M0174) was prepared using a modification of the procedures of Watanabe (Watanabe, K. A., et al., 1981). Under anhydrous conditions, fluorouridine (508 mg, 1.94 mmole) was dissolved in a mixture of anhydrous acetone (15 mL) and 2,2-dimethoxypropane (1.00 mL, 8.13 mmole). To this solution was added para-toluenesulfonic acid, monohydrate (71 mg, 0.37 mmole) and this mixture allowed to stir at room temperature, under an atmosphere of dry nitrogen gas for 18 hours. T.l.c. analysis after this time (SiO$_2$: irrigant=ethylacetate) showed conversion to a higher Rf product (Rf=0.69). Solid sodium bicarbonate (114 mg, 1.35 mmoles) was added to the solution and stirring continued as above for 2 hours. The reaction mixture was filtered, and the white precipitate washed with acetone (5×10 mL). The filtrate was evaporated to a white solid, and dried in vacuo (768 mg, crude). This crude product was recrystallized from hot 95% ethanol. After cooling to 4° C. overnight, colorless needle crystals of the 2,3-isopropylidine derivative were collected by filtration (366 mg, 63%). A second crop of crystals (113 mg) (total yield 479 mg (82%)) were also obtained by concentration of the mother liquors and cooling to 4° C.

Under anhydrous conditions, the isopropylidene derivative from above (302 mg, 1.0 mmole, 1$^{st}$ crop) was dissolved in anhydrous dichloromethane (30 mL). To this solution was added dry silver oxide (452 mg, 1.95 mmole), resublimed crystalline iodine (30 mg, 0.12 mmole) and acetobromogalactose (452 mg, 1.11 mmole) with stirring. This reaction mixture was heated to reflux, under anhydrous conditions for 18 hours, cooled, and the reaction mixture filtered through a pad of diatomaceous earth (Celite™), and the precipitate washed with chloroform (5×15 mL). The combined filtrates were extracted with water (1×50 mL), 0.1 M sodium thiosulfate solution (1×50 mL) and water (1×50 mL). The organic layer was dried over anhydrous sodium sulfate, filtered, and evaporated to dryness (597 mg, 94%). This fully protected nucleoside derivative (M0172) was deblocked in two steps using, first, the procedure of Lichtenhaler, et al. (Lichtenhaler, et al., 1978). The nucleoside derivative (M0172) was added to a solution of trifluoroacetic acid:water (5:1, 24 mL), and allowed to stir at room temperature for 25 minutes. The solution was then evaporated and co-evaporated with dry toluene (4×30 mL) and 1:1 methanol:toluene (1×40 mL), and dried in vacuo to give the crude peracetate derivative (M0173) (471 mg, grey solid). A sample of this compound (364 mg, 0.54 mmole) was then dissolved in anhydrous methanol (40 mL) under anhydrous conditions (dry nitrogen gas environment) and cooled to 0° C. using an ice-bath. Sodium methoxide solution (25% w/v, 500 μL) was added and this mixture allowed to stir at 0° C. and at room temperature overnight (18 hours). The reaction mixture was neutralized with washed, dry IRC-50(H+) resin (1 gram). The reaction mixture was filtered, and the resin washed with methanol allowing the washes to equilibrate with the resin during each wash (6×30 mL). The combined filtrates were evaporated to a clear oil that was crystallized from methanol:diethylether (1:10, 165 mL) twice. The final crop (201 mg, 87%) was filtered and dried in vacuo to an off-white powder. T.l.c (SiO$_2$, irrigant=1:1 ethylacetate:methanol, Rf=0.50). $^1$H-n.m.r. (D$^2$O) d: 8.0 (d, 1H, NH), 5.8 (d, 1H, H-1), 4.75 (d, 1H, H-1'), 4.4 (d, 1H, H-4'), 4.3-4.1 (m, 3H, Gal ring H's), 3.9-3.4 (m, 10H, ring H's).

Example 17

Preparation of a Tetracycline Galactoside Conjugate

The following compound was prepared:

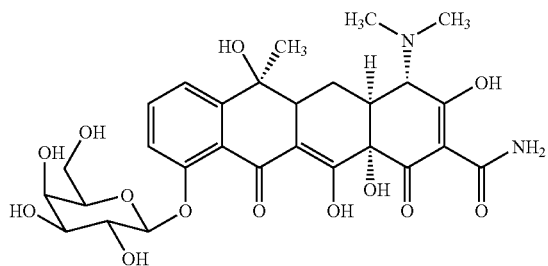 [SMILES: CN(C)[C@@H]1C(O)=C(C(N)=O)C(=O)[C@@]2(O)C(O)=C3C(=O)c4c(OC5OC(CO)C(O)C(O)C5O)cccc4[C@@](C)(O)C3C[C@@H]12]

Under anhydrous conditions, tetracycline (508 mg, 1.14 mmole) was suspended in anhydrous dichloromethane (25 mL) containing dry 3 Å molecular sieves (1 gram) with stirring for 1 hour. Dry silver oxide (348 mg, 1.5 mmole), resublimed iodine crystals (96 mg, 0.38 mmole) and acetobromogalactose (630 mg, 1.53 mmole) were added, and the reaction mixture allowed to stir, in the dark, under dry nitrogen gas for 78 hours. T.l.c. analysis (SiO$_2$: irrigant=9:1 chloroform:methanol) showed the conversion to three major new products, with Rf values of 0.64, 0.51 and 0.36 respectively, as well as remaining starting tetracycline (Rf=0). The reaction mixture was filtered through a bed of diatomaceous earth (Celite™ 545), and the precipitate washed with fresh dichloromethane (5×20 mL). The combined filtrates were extracted with 50% saturated brine solution (1×50 mL), 2% aqueous ammonium hydroxide solution (1×50 mL), 1 N aqueous hydrochloric acid solution (1×50 mL), and water (1×50 mL). The organic layer was dried over anhydrous sodium sulfate, filtered, evaporated, redissolved in chloroform (5 mL) and chromatographed on a column of silicagel 60 Å (70-230 mesh) (50 g), with elution using a gradient from 5% to 20% methanol in chloroform. Fractions from the first major component to elute from the column were combined and evaporated to dryness to give the fully protected glycoside (M0166, 245 mg, 28%).

This sample was dissolved in anhydrous methanol (20 mL) containing sodium methoxide (200 μL of a 25% w/v solution in methanol) under anhydrous conditions and allowed to stir at room temperature for 18 hours. The reaction was neutralized with washed, dry IRC50(H+) resin, filtered and the resin washed with excess methanol (4×15 mL) allowing the methanol to equilibrate with the resin for 3 minutes during each wash step. The combined filtrates were evaporated to dryness to give an off white powder (190 mg, 99% theoretical yield).

Example 18

Preparation of a Benzyl Cephalothin L-Glutamate Conjugate

The following compound was prepared:

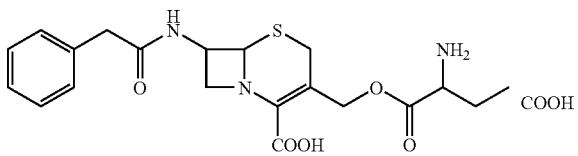

The title compound was prepared in a four step synthesis using a modification of the methods of Takaya, et al. (Takaya, et al., 1981) and Albrecht, et al. (Albrecht, et al., 1990). 7-Aminocephalosporanic acid (817 mg, 3.0 mmole) was suspended in water (3.3 mL) cooled to 0° C. (ice-salt bath), and a solution of 20% (w/v) sodium hydroxide in water (1.4 mL, 7.0 mmole) was added dropwise with stirring over a period of 10 minutes. The starting material was manually stirred until completely dissolved (15 minutes) and the pH adjusted to 8.5 with glacial acetic acid. The reaction mixture was diluted with acetone (2.5 mL) and phenylacetyl chloride (476 μL, 3.6 mmole) added, slowly with stirring. The pH was adjusted to 8.3 with triethylamine (1.5 mL) and this mixture allowed to stir at 0° C. for 1 hour. The reaction mixture was evaporated to remove the acetone, the aqueous layer overlayered with ethylacetate (15 mL) and the aqueous layer acidified with concentrated hydrochloric acid solution (pH 3.0), the ethylacetate layer removed, and the aqueous layer extracted with fresh ethylacetate (4×20 mL). The combined ethylacetate layers were back-extracted with saturated brine solution (1×30 mL) and then dried over anhydrous sodium sulfate. Evaporation gave 870 mg (83% theoretical yield).

Under anhydrous conditions, under dry N$_{2(g)}$, a sample of this benzyl cephalothin (685 mg, 1.97 mmole) in ethylacetate was treated with freshly prepared diphenyldiazomethane (Org. Synth. Coll. Vol. 3, 351) over a period of 2 hours at ambient temperature until a reddish color persisted in the reaction (total 5.0 mL). After concentrating to 15 mL, and storage at 4° C. for 18 hours, the white crystalline percipitate was collected and dried in vacuo (310 mg, 31% theoretical yield). $^1$H-n.m.r. (CDCl$_3$) d: 7.5-7.2 (m, 15H, Ph-H), 6.9 (s, 1H), 6.1 (m, 1H), 5.9 (m, 1H), 5.0 (dd, 1H), 4.9 (m, 1H), 4.4 (dd, 1H), 3.9 (dd, 1H), 3.7-3.6 (m, 2H), 3.5 (s, 1H), 2.5 (m, 10H).

The diphenyl methyl ester, benzyl amide from above (150 mg, 0.29 mmole) was dissolved in anhydrous tetrahydrofuran (10 mL) containing 3 Å molecular sieves (0.5 g) and cooled to 0° C. (ice-bath). N-tert-butyloxycarbonyl-L-glutamic acid g-tert-butyl ester (199 mg, 0.387 mmole), dicyclohexylcarbodiimide (137 mg, 0.664 mmole) and N,N-dimethylaminopyridine (53 mg, 0.44 mmole) were added, and the reaction mixture allowed to stir under anhydrous conditions, under dry nitrogen gas, at ambient temperature for 18 hours after which time t.l.c. analysis showed the appearance of a new product (SiO$_2$; Rf=0.40, irrigant=9:1 chloroform:ethylacetate). The reaction mixture was filtered, and the precipitate washed with chloroform (50 mL); the combined filtrate was extracted with brine solution (50 mL), saturated aqueous sodium bicarbonate solution (50 mL), 1 N aqueous hydrochloric acid solution (50 mL) and brine solution (50 mL). The organic layer was dried over anhydrous sodium sulfate for 18 hours, filtered, evaporated and dried in vacuo to a white solid (342 mg) which was applied to a column of silicagel G (70-230 mesh, 25 grams) and eluted with a gradient of chloroform (300 mL), 9:1 chloroform:ethylacetate (500 mL) and 9:1 chloroform:methanol (250 mL). Fractions containing the first major product to elute from the column were combined, evaporated and dried in vacuo to a white solid (220 mg, 94% theoretical yield).

Under anhydrous conditions, this sample was partially dissolved in anhydrous anisole (0.66 mL), cooled to 0° C. (ice-bath), and treated with anhydrous trifluoroacetic acid (3.3 mL). This homogeneous solution was allowed to stir under these conditions for 4 hours, evaporated and co-evaporated with anhydrous dichloromethane (4×20 mL) and anhydrous toluene (20 mL), triturated with ethylacetate (30 mL) for 18 hours at ambient temperature. The white crystalline solid was collected to give 63 mg (50% theoretical yield) of the title compound.

Example 19

Preparation of a Doxorubicin Galactoside Conjugate

The following compound was prepared:

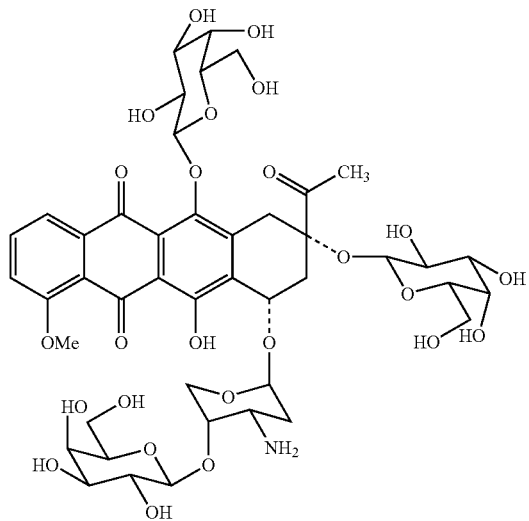 [SMILES: COc1cccc2c1C(=O)c1c(O)c3c(c(OC4OC(CO)C(O)C(O)C4O)c1C2=O)C[C@@](OC1OC(CO)C(O)C(O)C1O)(C(C)=O)C[C@@H]3OC1CC(N)C(OC2OC(CO)C(O)C(O)C2O)CO1]

Under anhydrous conditions, doxorubicin (8 mg, 13 μmole) was dissolved in anhydrous methanol containing triethylamine (2 μL, 14 μmole) and trifluoroaceticanhydride (2 μL, 14 μmole). This solution was allowed to stir at room temperature, under anhydrous nitrogen gas for 18 hours. The reaction mixture was neutralized with triethylamine (10 μL) and evaporated and co-evaporated with 1:1 toluene:methanol (3×10 mL), and dried in vacuo. This solid was suspended in anhydrous dichloromethane (10 mL) containing 3 A molecular sieves (0.5 g), acetobromogalactose (29 mg, 71 μmole), sym-collidine (9.0 μL, 67 μmole) and silver trifluoromethanesulfonate (18 mg, 67 μmole). This mixture was allowed to stir in the dark, at room temperature under anhydrous nitrogen gas for 120 hours, after which time t.l.c. analysis indicated production of a single product (Rf=0.53, SiO$_2$ plate, irrigant=1:1 acetone:methanol). The reaction mixture was applied directly to a column of silicagel G (70-230 mesh, 10 gram) and eluted with chloroform (50 mL), 9:1 chloroform:methanol (250 mL) and 1:1 acetone; methanol (200 mL). Fractions containing the first major product to elute from the column were combined and evaporated to give the a solid (22 mg, 100% theoretical yield). This sample was dried in vacuo, dissolved in anhydrous methanol (10 mL) containing sodium methoxide (71 mg, 1.3 mmole) at 0° C. (ice-bath), and allowed to stir at 0° C. for 2 hours and at room temperature for 15 hours. The reaction mixture was neutralized with washed, dry IRC-50(H+) resin, filtered and the resin washed with methanol (20 mL), water and chloroform to give 21 mg of an orange solid. T.l.c. analysis (SiO$_2$, irrigant=1:1 acetone:methanol, Rf=0.70), $^1$H-n.m.r. analysis conformed to the expected structure for a tri-galactoside conjugate.

Example 20

Preparation of a Resveratrol Galactoside Conjugate

The following compound was prepared:

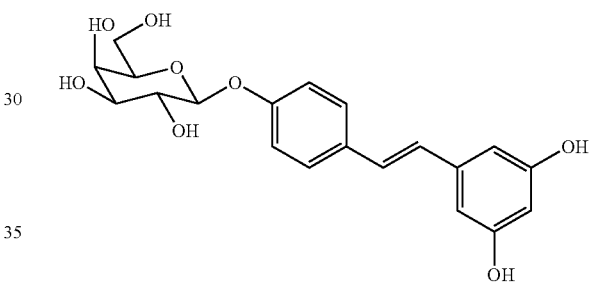

Resveratrol (77 mg, 0.337 mmole) was dissolved in anhydrous dichloromethane (20 mL) and anhydrous acetonitrile (5 mL) containing 3 Å molecular sieves (1 gram). Sym-collidine (134 μL, 1.01 mmole), dry silver carbonate (140 mg, 0.51 mmole) and acetobromogalactose (416 mg, 1.01 mmole) were added sequentially under anhydrous conditions, and this mixture allowed to stir under anhydrous nitrogen gas, in the dark, for 72 hours at 25° C. T.l.c. analysis (SiO$_2$ plate; irrigant=9:1 chloroform:methanol) showed the production of three products (Rf=0.53, 0.29, 0.09 respectively). The reaction mixture was filtered through a Celite™ or diatomaceous earth pad and the precipitate washed with fresh chloroform (5×10 mL). The combined filtrates were extracted with water, 1 N aqueous hydrochloric acid solution, saturated aqueous sodium bicarbonate solution, 2% aqueous ammonium hydroxide solution and water (1×50 mL each). The combined organic layers were dried over anhydrous sodium sulfate, filtered, evaporated to dryness and dried in vacuo. The crude sample was applied to a column of Silicagel G (70-230 mesh, 20 grams) and eluted with chloroform:methanol (19:1). The second major product to elute from the column was combined, evaporated, and dried in vacuo to give a glass (48 mg, 22% theoretical yield). $^1$H-n.m.r. analysis (CDCl$_3$) indicated production of a mono-galactoside product.

The per-acetate from above (40 mg, 0.07 mmole) is suspended in anhydrous methanol and sodium methoxide/methanol (25% w/v) added (0.5 mL). This mixture is allowed to stir at 0° C. for 2 hours and at room temperature for 16 hours. The reaction is neutralized with washed, dry IRC50

(H+) resin, the resin filtered and washed with methanol (6×10 mL) and the filtrate evaporated to a white solid, homogeneous by t.l.c. (SiO$_2$: irrigant=7:3 ethylacetate:methanol).

Example 21

Preparation of a Phorbol Octanoate Acetate Galactoside Conjugate

The following compound was prepared:

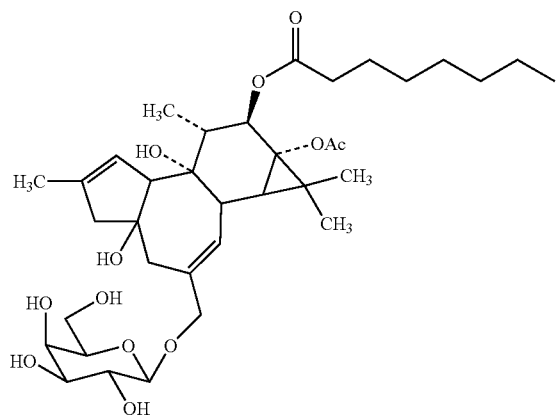 [SMILES: CCCCCCCC(=O)O[C@@H]1[C@@H](C)[C@@]2(O)C(C=C(COC3OC(CO)C(O)C(O)C3O)CC3(O)CC(C)=CC32)C2C(C)(C)[C@@]21OC(C)=O]

Phorbol (4b,9a,12b,13a,20-pentahydroxytiglia-1,6-dien-3-one) (40 mg, 0.11 mmole) was suspended in anhydrous acetonitrile (4 mL) containing 3 A molecular sieves (0.1 g) and acetobromogalactose (55 mg, 0.13 mmole), silver triflate (38 mg, 0.13 mmole) and sym-collidine (16 µL, 0.12 mmole) added sequentially, under dry nitrogen gas, slowly with stirring. This mixture was allowed to stir in the dark, under anhydrous conditions for 10 days. After this time, t.l.c. analysis indicated production of two major products (Rf=0.26 and 0.44; SiO$_2$ plate: irrigant=9:1 chloroform:methanol). The reaction mixture was filtered through a pad of diatomaceous earth (Celite 545™), and the precipitate washed with chloroform (5×5 mL) and acetonitrile (5×5 mL). To the combined filtrates were added diatomaceous earth (Celite 545™) (2 grams) and the mixture evaporated to dryness and dried in vacuo. This sample was applied to a column of silicagel G (70-230 mesh), slurry packed in chloroform as eluent, and the product eluted by gradient elution using chloroform (200 mL), 9:1 chloroform:methanol (250 mL) and 8:2 chloroform:methanol (250 mL). The first product fractions to elute from the column were combined and evaporated and dried in vacuo to give 52 mg (69% theoretical yield) of an off white powder. T.l.c. and $^1$H-n.m.r. analysis (d$_6$-DMSO) indicated that the sample was a mixture of two mono-galactoside isomers.

The sample of mixed isomers (52 mg, 75 µmole) was suspended in anhydrous dichloromethane (3 mL) containing 3 A molecular sieves (0.2 g) and this sample placed under dry nitrogen gas and cooled to 0° C. Dry pyridine (100 µL, 1.24 mmole) and octanoyl chloride (100 µL, 586 µmole, 7.8 equivalents) were added with stirring and the reaction mixture allowed to stir as above at 4° C. overnight. The reaction mixture was cooled to 0° C., diluted with dichloromethane (5 µL) and water (10 µL) added. Stirring was continued for 30 minutes, chloroform (50 mL) added and the organic layer separated. This sample was extracted with 1 N aqueous hydrochloric acid solution, saturated aqueous sodium bicarbonate solution, and water (1×50 mL each). The final organic layer was dried over anydrous sodium sulfate, filtered, and evaporated to dryness.

One half of this crude sample (37 mg) was dissolved in anhydrous methanol (15 mL), placed under an atmosphere of dry nitrogen gas and cooled to 0° C. Sodium methoxide/methanol solution (25% w/v) (0.25 mL) was added with stirring, and the mixture allowed to stir as above for 2 hours. The reaction mixture was neutralized with washed, dry IRC50 (H+) resin, filtered, the resin washed with methanol (6×10 mL) and the combined filtrates evaporated to a off-white waxy solid (40 mg).

Example 22

Preparation of a Dioctanoyl Glycerol Galactoside Conjugate

The following compound was prepared:

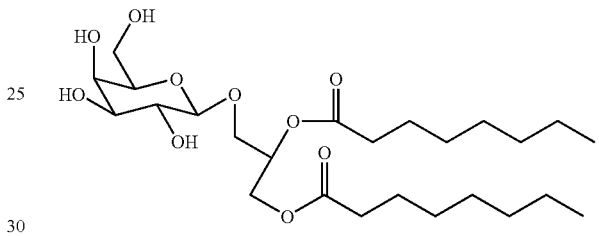

1,2-isopropylidine rac-glycerol was prepared by a modification of the method of Renoll and Newman (Renoll, 1948). Anhydrous glycerol (26.25 g, 0.285 mole) was dissolved in anhydrous acetone (75 mL, 1.02 mole) and petroleum ether (b.p.=37-58° C.) (75 mL) to form two layers. p-Toluenesulfonic acid, monohydrate (1.15 g, 6.05 mmole) was added and the reaction mixture heated to reflux using a Dean-Stark trap to collect water produced. After about 7 mL of water was collected in the Dean-Stark trap, the reaction mixture became homogeneous. Refluxing was continued for 13 hours, after which time approximately 11 mL of water was collected. The reaction was cooled and anhydrous sodium acetate (1.15 grams) was added and the reaction allowed to stir at ambient temperature for 30 minutes, filtered, and the solids washed with petroleum ether (20 mL). The combined filtrates were vacuum distilled (rotary evaporator) to a clear oil (T<35° C.). The final crude product (39.7 grams) was vacuum distilled at 14 mm Hg, and the fraction distilling at 93-95° C. collected to give a clear oil (30.98 g, 82% theoretical yield). $^1$H-n.m.r. spectral data (d$_6$-DMSO) was in agreement with the proposed structure.

A solution of the 1,2-isopropylidene glycerol (2.0 g, 15.13 mmole) in anhydrous dimethylformamide (10 mL) was placed under dry nitrogen gas and cooled to 0° C. (ice-bath), and benzyl bromide (3.6 mL, 30.26 mmole) added slowly with stirring. Solid dry silver oxide (3.50 g, 15.13 mmole) was added slowly with stirring over 30 minutes, and the reaction allowed to stir in the dark, under dry nitrogen gas at ambient temperature for 40 hours. The reaction mixture was then filtered, and the filter cake washed with dimethylformamide (2×5 mL) and chloroform (3×10 mL). The combined filtrates were extracted with 1% aqueous potassium cyanide solution (100 mL) and the aqueous layer back-extracted with chloroform (3×20 mL). The combined organic layers were extracted with water (3×20 mL), dried over anhydrous sodium sulfate, filtered, and evaporated. The crude product was adsorbed onto diatomaceous earth (Celite 545™) (2 g) and applied to a column of Silicagel G (250 grams) slurry-packed using hexanes as solvent, and eluted by gradient elution using 2%, 5%, 10%, 20% and 30% ethylacetate in hexanes (250 mL of each) as eluent. The fractions containing the fourth major product to elute from the column (t.l.c. $SiO_2$ plate, Rf=0.20, 5% ethylacetate:hexanes) were combined and evaporated to give 1.69 g (50% theoretical yield) of the title compound. $^1$H-n.m.r. ($CDCl_3$) α: 7.2 (s, 5H, Ph-H), 4.4 (m, 2H, Ph-CH2), 4.2 (m, 1H, O—CH), 4.0 (m, 1H, O—CH), 3.6 (m, 1H, O—CH), 3.5-3.3 (m, 2H, 2×O—CH), 1.3 (s, 3H, CH3), 1.2 (s, 3H, CH3).

A sample of the purified benzyl isopropylidene derivative (600 mg, 2.7 mmole) was dissolved in methanol (10 mL) and water (1 mL) with stirring. Solid para-toluenesulfonic acid, mono-hydrate (100 mg, 0.53 mmole) was added and the reaction mixture allowed to stir at 25° C. for 12 hours and at reflux for 1 hour. After cooling, washed Dowex™ 2×4 resin (5 mL, 5 mequiv.) was added and the reaction stirred for 30 minutes. The reaction mixture was filtered and the resin washed with fresh methanol (3×10 mL). The combined filtrates were evaporated and dried in vacuo to a clear oil (463 mg, 94% theoretical yield), homogeneous by thin layer chromatography ($SiO_2$ plate, irrigant=9:1 chloroform:methanol, Rf=0.33).

This sample was converted directly to the di-octanoyl derivative using the procedure of Briggs, et al. (Briggs, et al., 1992). 1-O-Benzyl rac-glycerol (463 mg, 2.54 mmole) was dissolved in dry pyridine (10 mL) under anhydrous conditions and dry nitrogen gas, and cooled to 0° C. Redistilled octanoyl chloride (0.96 mL, 5.6 mmole) was added and the reaction mixture allowed to stir as above at 0° C. for 2 hours and at room temperature overnight (16 hours). The reaction mixture was poured into saturated aqueous sodium bicarbonate solution (25 mL) and stirred for 10 minutes, and this solution extracted with chloroform (2×50 mL). The combined chloroform extracts were back-extracted with water (1×50 mL), 1 N aqueous hydrochloric acid solution (2×25 mL), saturated aqueous sodium bicarbonate solution (1×50 mL) and water (1×50 mL). The organic layer was dried over anhydrous sodium sulfate, filtered and evaporated to a clear oil (0.800 g, 72%). T.l.c. ($SiO_2$ plate, irrigant=chloroform, Rf=0.19).

This sample was dissolved in methanol (14 mL) and glacial acetic acid (2 mL), flushed with an atmosphere of hydrogen gas (×3) and 5% palladium on carbon catalyst (0.15 g, 7.5 mg Pd) was added as a slurry in methanol. The reaction mixture was flushed again with hydrogen gas (×3) and left to stir under atmospheric pressure hydrogenation conditions for 7 hours. The reaction was then flushed with nitrogen gas, the catalyst removed by filtering through a pad of diatomaceous earth (Celite™ 545) and the precipitate washed with methanol (4×5 mL). The combined filtrates were evaporated and dried in vacuo to yield 620 mg (99% theoretical yield) of a waxy solid. A sample of this material (360 mg) in hexanes (5 mL) was applied to a column of silicagel G (70-230 mesh, 40 g) slurry packed in 19:1 hexanes:ethylacetate, and the product eluted by gradient elution using 19:1 hexanes:ethylacetate (600 mL), 9:1 hexanes:ethylacetate (200 mL), 17:3 hexanes:ethylacetate (200 mL) and 8:2 hexanes:ethylacetate (200 mL). Fractions containing the second major product to elute from the column were combined and evaporated to give 124 mg of an analytical sample. T.l.c analysis ($SiO_2$ plate, irrigant=9:1 chloroform:methanol, Rf=0.57, irrigant=4:1 hexanes:ethylacetate, Rf=0.33).

Enzymatic synthesis of the 3-O-β-D-galactoside was performed using a modification of the procedure of Kren, et al. (Kren, et al., 1992) that employs the β-galactosidase enzyme from *Aspergillus oryzae* reported to provide higher yields of galactosides from lipophilic aglycones.

1,2-di-octyl-rac-glycerol (DOG) (65 mg, 0.19 mmole) was dissolved in dimethylsulfoxide (100 mL). p-Nitrophenyl β-D-galactopyranoside (ONPG) (150 mg, 0.50 mmole) was dissolved in 0.1 M $Na_2HPO_4$/0.01M $MgCl_2$ buffer, pH 7.0 (4.0 mL) and Tris buffer (pH 7.3, 1.0 mL) was added. The ONPG solution was added slowly to the DOG solution, with vortex mixing, and the solution warmed to 45° C. to dissolve. After cooling, β-galactosidase from *Aspergillus oryzae* (172 U) was added and the reaction mixture slowly rotated at 25° C. for 24 hours. The reaction mixture was applied directly to a column of Silicagel G (70-230 mesh, 20 g) and eluted by gradient elution using 0-20% methanol in hexanes as eluent. Fractions containing the second major product to elute from the column were combined and evaporated to give a white solid (80 mg, 83% theoretical yield).

Example 23

Preparation of a 4-O-Galactosyl Phenyl Retinamide Conjugate

The following compound was prepared:

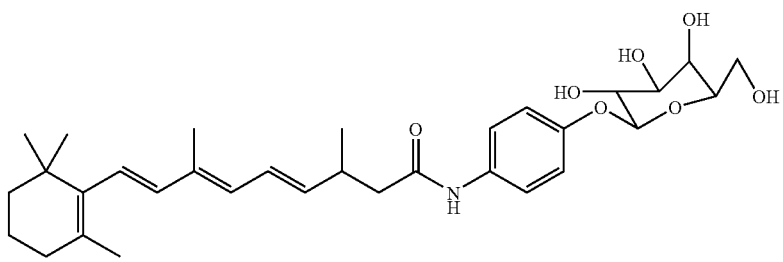 [SMILES: CC1=C(/C=C/C(C)=C/C=C/C(C)CC(=O)Nc2ccc(OC3OC(CO)C(O)C(O)C3O)cc2)C(C)(C)CCC1]

p-Nitrophenyl β-D-galactopyranoside (500 mg, 1.659 mmole) was dissolved in dry methanol (30 mL) and a slurry of 5% Palladium on carbon in dry methanol (2 mL, +2×2 mL rinses) added. The reaction flask was evacuated and flushed with hydrogen gas and left to stir under an atmosphere of hydrogen gas for 4 hours. After this time t.l.c. analysis showed the production of a new, ninhydrin positive product (Rf=0.62, $SiO_2$; irrigant=1:2 chloroform:methanol). $^1$H-n.m.r. ($D_6$-DMSO) was consistent with the p-aminophenyl β-D-galactoside structure expected.

Under anhydrous nitrogen gas conditions, in the dark, retinoic acid (all-trans) (207 mg, 0.67 mmole) was suspended in dry toluene (5 mL). A solution of phosphorus trichloride (100 µL) in dry toluene (2.5 mL) was prepared in a separate dry flask, under anhydrous conditions, and 2.0 mL of this PCl$_3$/toluene solution was added to the reaction (80 Mg PCl$_3$, 0.88 mmole) in two portions (1.0 mL each) slowly over two hours. The reaction mixture was allowed to react under these conditions for 2.5 hours, after which triethylamine (200 µL, 1.43 mmole) was added to neutralize the excess PCl$_3$.

A sample of the p-aminophenyl β-D-galactoside was dissolved in N,N-dimethylformamide ($\overline{5}$ mL, neutral alumina washed), and the acid chloride solution was added slowly to this by passage through a plug of glass-wool, (+2×1.0 mL DMF rinses). The reaction was allowed to react at room temperature for 18 hours, and methanol (3.0 mL added to destroy the excess acid chloride. After concentrating to approximately 10 mL, the crude product was precipitated by adding diethylether (100 mL), filtered, redissolved in methanol (30 mL) and adsorbed onto diatomaceous earth (Celite™ 545, 5 grams), and dried in vacuo. The sample was purified on a column of silicagel G (70-230 mesh) using a step gradient elution method (9:1; 8:2; 7:3; 6:4; and 1:1 chloroform:methanol; 200 mL each) as eluent. The second major product fractions to elute from the column (Rf=0.64; SiO$_2$: irrigant=7:3 chloroform:methanol) were combined, evaporated and dried in vacuo to give a yellow solid (53 mg, 14% theoretical yield). $^1$H-n.m.r. (d$_6$-DMSO) δ:9.9 (s, 1H, N—H), 7.5 (d, 2H, Ph-H), 6.9 (d, 2H, Ph-H), 6.4-5.9 (m, 4H, C=C—H), 5.1 (d, 1H, —OH), 4.8 (d, 1H, —OH), 4.7 (d, 1H, H-1), 4.6 (m, 1H, —OH), 4.5 (d, 1H, —OH), 3.7 (d, 1H, H-4), 3.5-3.1 (m, 5H, ring protons), 2.3 (s, 3H, —CH3), 2.0 (m, 2H, CH2), 2.0 (s, 3H, —CH3), 1.7 (s, 3H, —CH3), 1.5 (m, 2H, CH2), 1.4 (m, 2H, CH2) and 1.0 (s, 6H, 2×—CH3).

This sample was dried in vacuo overnight, over P$_2$O$_5$. It was dissolved in anhydrous methanol (20 mL) cooled to 0° C., and 25% (w/v) sodium methoxide/methanol (500 mL, 2.19 mmole) added and allowed to stir at 0° C. for 2 hours and at 25° C. for 14 hours. The reaction mixture was neutralized with washed, dry IRC50 (H+) resin (1 gram) and the resin filtered and washed with fresh methanol (20 mL) chloroform (20 mL) and water (20 mL). The combined filtrates were evaporated and dried in vacuo to a blue glass (75 mg) that was to a preparative t.l.c. plate (Silicagel GF: 20×20 cm, 1 mm thickness) and eluted with 1:1 acetone:methanol. The product band (Rf=0.75-0.85) was removed and the product eluted from the silica using 1:1 acetone:methanol. The eluted product fraction was filtered, evaporated and recrystallized from methanol:diethylether (1:10) to give a blue-white powder (9 mg, 20%). $^1$H-n.m.r. analysis was consistent with the structure as shown.

Method B:

p-Nitrophenyl β-D-galactopyranoside (150 mg, 0.50 mmole) was dissolved in 0.1 M Na$_2$HPO$_4$/0.01M MgCl$_2$ buffer, pH 7.0 (4.0 mL) and Tris buffer (pH 7.3, 1.0 mL) was added. Mitoxantrone, dihydrochloride salt (50 mg, 0.11 mmole) was added, and the mixture vortex mixed for 3 min. E. coli β-Galactosidase (172 µL of a 500 U/mL solution in water, 86 U total) was added and the solution rotated slowly at 25° C. for 24 hours. T.l.c. analysis (SiO$_2$ plate, irrigant=8:2:1:0.1 isopropanol:water:triethylamine:acetic acid) indicated product formation. Purification is carried out by preparative t.l.c using the similar systems to those employed in Method A above, to give the title compound.

Example 24

Preparation of a Mitoxantrone Di-Galactoside Conjugate

The following compound was prepared:

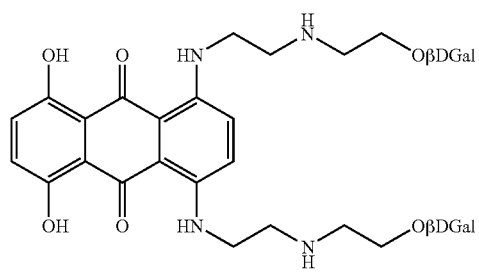

Method A:

Under anhydrous conditions and a dry nitrogen gas atmosphere, mitoxantrone, di-hydrochloride salt (40 mg, 77 mmole) was suspended in dry dichloromethane (20 mL) containing sym-collidine (40 mL) and 3 A molecular sieves (0.3 g). Acetobromogalactose (196 mg, 0.0.48 mmole), silver triflate (123 mg, 0.48 mmole) and additional sym-collidine (120 mL, 0.91 mmole) were added, and the reaction flask stirred in the dark for 4 days. The reaction mixture was applied directly to a column of silicagel G (70-230 mesh, 25 g) slurry-packed in chloroform, and eluted with 9:1 chloroform:methanol (250 mL) and 1:1:0.1:0.1 ethylacetate:methanol:triethylamine: water (300 mL). Fractions containing the first bluish product to elute from the column were combined and evaporated to give the crude peracetylated galactoside (142 mg).

Example 25

Preparation of a Thymidine 5-O-β-D-Galactoside Conjugate

The following compound was prepared:

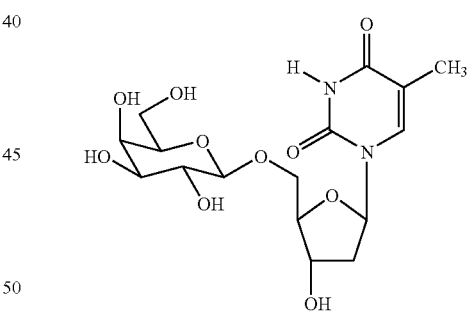

Under anhydrous conditions, thymidine (200 mg, 0.826 mmoles) was dissolved in anhydrous dichloromethane (10 mL). To this solution was added acetobromogalactose (845 mg, 2.05 mmoles), silver carbonate (170 mg, 0.620 mmoles), and sym-collidine (220 µL, 1.65 mmoles) with stirring. This reaction mixture was stirred in the dark under anhydrous conditions for 24 hours. The reaction mixture was then filtered through a pad of diatomaceous earth (Celite™), and the precipitate washed with chloroform (5×15 mL). The combined filtrates were extracted with water (1×100 mL), 2% ammonium hydroxide solution (1×100 mL), 1.0 N Hydrochloric acid solution (1×100 mL), saturated sodium bicarbonate solution (1×100 mL), and water again (1×100 mL). The organic layer was dried over anhydrous sodium sulfate, filtered, and evaporated to dryness. The sample was then subjected to column chromatography (silica gel 60 Å, 35 grams) using a gradient elution with 0-40% ethyl acetate in chloroform as eluent. The second major product eluting from the column was combined, evaporated and dried in vacuo to give 42 mg (9% theoretical yield). T.l.c. (SiO$_2$, Rf=0.53, irrigant=1:1 chloroform:ethylacetate). $^1$H-n.m.r. (CDCl$_3$) δ: 7.8 (s, 1H), 5.6-5.3 (m, 4H), 5.2 (dd, 1H, H-3'), 5.1 (m, H-4'), 4.5-4.0 (m, 5H), 2.9 (m, 1H, H-5), 2.2 (m, 2H, CH2), 2.2-2.0 (4×s, 3H each, -Oac). 1.6 (s, 3H, —CH3).

This dried per-acetate derivative was dissolved in anhydrous methanol (10 mL) and cooled to 0° C. 25% (w/v) NaOMe/MeOH (100 μL) was added, and this mixture allowed to stir under anhydrous conditions for 15 hours. The reaction mixture was neutralized with washed, dry IRC50 (H+) resin, filtered, and the resin washed with dry methanol. The combined filtrates were evaporated to a small volume (5 mL), to which was added diethyl ether (30 mL). The crystallized product was filtered, redissolved in MeOH, then evaporated and dried in vacuo to give a white crystalline solid (18 mg, 60% theoretical yield), homogeneous by t.l.c. (SiO$_2$, Rf=0.68, irrigant=9:1 ethylacetate:methanol).

Example 26

Phase I Clinical Study Involving Administration of Marker Gene Modified Ovarian Tumor Cells with Subsequent Pro-Drug Therapy The maximum tolerated dose (up to $10^{10}$ cells per treatment) of genetically modified tumor cells (see Example 10) will be determined. Tumor cells from patients will be removed by biopsy, and grown in vitro using standard clinical tissue culture techniques. Once stable growth in culture is confirmed, transformation of these cells with a vector containing the lacZ gene will be effected using either a lipofection technique (see Example 9) or a retroviral vector technique. Four patients will be injected intra-tumorally, with $3 \times 10^7$ irradiated tumor cells on day 0. Approximately 24 hours after cell infusion, the patients will be started on a 14 day course of I.V. pro-drug administration. Two weeks after the termination of pro-drug therapy, each patient will be evaluated in terms of side-effects from treatment, and progression of the disease state. If no adverse toxicity occurred from the previous tumor cell treatment and pro-drug therapy, and there appears to be no evidence of progressing tumor growth that would require alternate therapy, then the patient will be eligible for the next dose (regimen) of cellular/pro-drug therapy. This schedule will continue for doses of $1 \times 10^8$ and $3 \times 10^8$ cells for Group 1. If no adverse side effects warranting the stoppage of therapy are reported in Group 1, then Group 2 patients will be treated at one dose level higher, and this pattern will continue through four groups. If a patient has to drop out of the study for reasons other than toxicity, then another patient may be added to the group and will begin therapy at the lowest dose level for that group.

The patients will be admitted to the hospital for the first fifteen days of each cycle. The transformed cells will be given on day 1 and pro-drug treatment on days 2 through 15. The treatment is repeated at three week intervals for a total of three cycles of treatment. At the completion of treatment, patients will be followed regularly until, and if there is a progression of disease.

Cellular and pro-drug administration. Patients will be assigned in order of entrance in the study to one of the four treatment schedules below. The dosages escalate with each treatment unless toxicity of Grade II or higher has occurred. For Grade II toxicity, except for nectropenia or thrombocytopenia, the dose is repeated but physician discretion could lower the dose if overall toxicity is of concern. For Grade III or Grade IV toxicity, the dosage is lowered one level.

| Patients | First Dose | Second Dose | Third Dose |
|---|---|---|---|
| 1-4 | $3 \times 10^7$ | $1 \times 10^8$ | $3 \times 10^8$ |
| 5-8 | $1 \times 10^8$ | $3 \times 10^8$ | $1 \times 10^9$ |
| 9-12 | $3 \times 10^8$ | $1 \times 10^9$ | $3 \times 10^9$ |
| 13-16 | $1 \times 10^9$ | $3 \times 10^9$ | $1 \times 10^{10}$ |

The cell suspension is prepared in 1.5 cc of normal saline and administered through a small intratumoral catheter which is inserted on the day of treatment and removed after the 1 hour infusion. Catheter placement and diffusion of fluid will be checked by a technician flow study prior to cell infusion.

The drug conjugates are all prepared from FDA-approved drugs used for treatment of human cancers. The bioavailability and clearance levels of pro-drugs are required to be measured prior to treatment. The pro-drugs will be provided as a sterile powder and they are reconstituted with sterile water. For I.V. administration, these will be prepared in 100 cc of normal saline, or 5% dextrose and water, and infused over a period of one hour.

The standard dose of these drugs will be from 0.5 to 5 mg/kg b.i.d. when patients have a creatine clearance >80. If the creatine clearance level is 50-79, the dose is reduced to by one-half to 0.25-2.5 mg/kg b.i.d. Daily CBC and platelet counts will be obtained during treatment. The pro-drug administrations should be stopped if the absolute granulocyte count falls below 750 or the platelets are less than 50,000 count.

Example 27

Preparation of a D-Luciferin-Bromoxynil Conjugate

The following compound is prepared:

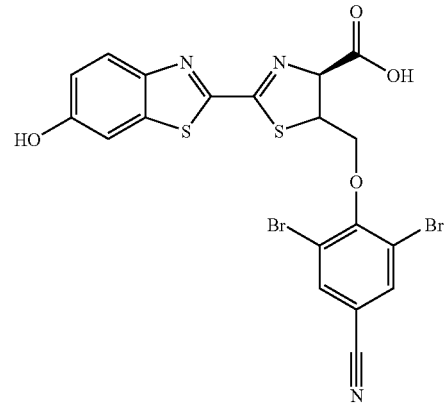 [SMILES: N#Cc1cc(Br)c(OCC2SC(c3nc4ccc(O)cc4s3)=N[C@H]2C(=O)O)c(Br)c1]

Method A: Preparation of a
5-Oxymethyl-D-Luciferin Cycloheximide Conjugate

5-Hydroxymethyl-D-Luciferin. A modification of the procedure of Seto, S., et al., 1963 is used. A mixture of 2-Cyano-6-hydroxybenzothiazole (200 mg), ?-hydroxymethyl D-Cysteine (200 mg), potassium carbonate (160 mg) and 50% aqueous methanol (10 mL) is stirred under a stream of nitrogen gas, at room temperature for 2.5 hours. After neutralization with 1 N aqueous HCl, the precipitate is collected, washed with water and recrystallized from 95% ethanol to give the title compound.

6'-O-t-butyldimethylsilyl-5-hydroxymethyl-D-Luciferin, t-butyldimethylsilyl ester. Under anhydrous conditions. 5-hydroxymethyl-D-Luciferin (45 mg, 0.145 mmole) is dissolved in anhydrous dimethylformamide (7 mL), cooled to 0° C. (ice-bath) and imidazole (300 µL) and t-butyldimethylsilyl chloride solution (50% solution in tetrahydrofuran, 52 µL, 2.1 equiv.) is added. The reaction mixture is allowed to stir at 0° C. for 2 hours and at room temperature overnight. The major product is purified by silicagel column chromatography using dichloromethane:ethylacetate gradient elution. Fractions containing the first major product to elute from the column are combined and evaporated to give the title compound as a white solid.

5-O-(cycloheximidyl)oxymethyl-D-Luciferin. Under anhydrous conditions, 6'-O-t-butyldimethylsilyl-5-hydroxymethyl-D-Luciferin, t-butyldimethylsilyl ester (54 mg, 0.10 mmole) is dissolved in dichloromethane (150 mL). A solution of carbonyldiimidazole (17 mg, 0.105 mmole) in dichloromethane (10 mL) is added slowly over 25 minutes. The reaction mixture is allowed to stir at room temperature for 1 hour, and the volume reduced to approximately 20 mL (rotary evaporator, and a solution containing cycloheximide (28 mg, 0.10 mmole) in dichloromethane (10 mL) is added. This final solution is allowed to stir at room temperature for an additional 6 hours. The reaction mixture is poured directly onto a column of 50 grams (100 mL) silicagel and eluted using a dichloromethane:ethylacetate gradient elution. Fractions containing the conjugate product from the column are combined and evaporated to give a protected compound as a white solid. The final product is deprotected using a dilute solution of tetrabutylammonium fluoride in methanol to give the title compound.

Method B: Preparation of a D-Luciferin-Bromoxynil Conjugate

Potassium-L-threonate. A modification of the procedure of Humphlett (Humphlett, W. J., 1967) is employed. Oxygen is bubbled through a stirred solution of potassium hydroxide (112 g) in water (240 mL) and methanol (1 L) employing a gas dispersion tube. A solution of L(+)-arabinose (100 g, 666 mmol) in water (240 mL) is added to the stirred, oxygenated solution at such a rate that a temperature of 30-35° C. is maintained. Oxygen was continuously bubbled during the addition and for an additional hour after the addition is complete. Air was then bubbled through the solution for an additional 48 hours. The solution is diluted with methanol (1.6 L) and stored in a freezer for several days. The resulting solid is collected, washed with methanol and dried to yield the title compound as a white solid (75 g, 65% theoretical yield).

Methyl 2,4-dibromo-2,4-dideoxy-L-threonate. A modification of the procedure of Bock, et. al. (Bock, et al., 1983) is employed. A solution of potassium-L-threonate (20.0 g, 115 mmol) in 32% hydrogen bromide in acetic acid is stirred at room temperature for 24 hours. Methanol (500 mL) is stirred in and the solution allowed to stand overnight to give a suspension. The solid (potassium bromide) is removed by filtration and the solvent removed from the filtrate. Methanol is added to the residue (200 mL) and the mixture heated at reflux for 2 hours. The methanol is removed and the residue dissolved in ethyl acetate (100 mL). The solution is washed with water (100 mL) and dried over sodium sulfate. The solvent is removed and the residue crystallized from ether/pentane to yield the title compound (24.0 g, 76%).

Methyl (2S,3S)-4-acetoxy-2,3-epoxybutanoate. The general procedure of Manchand, et. al. (Manchand, et al., 1988) is employed. Methyl 2,4-dibromo-2,4-dideoxy-L-threonate (131 g, 474 mmol) is added to a stirred solution of potassium acetate (102 g, 1.04 mol) and potassium iodide (3.94 g, 23.8 mmol) in dimethyl formamide (500 mL). This mixture is stirred under nitrogen gas at 50-55° C. for 4 hours and overnight at room temperature. The reaction mixture is diluted with ethyl acetate (1 L) and filtered. The filter cake is washed with ethyl acetate (250 mL). The combined ethyl acetate portion is washed with saturated sodium bicarbonate solution (500 mL) and saturated brine (2×500 mL) and dried over magnesium sulfate. The solvent is removed to yield the title compound as a dark oil (82.0 g, 99% theoretical yield).

(2S,3S)-2,3-Epoxy-4-hydroxybutanoic acid sodium salt. A modification of the general procedure of Manchand, et. al. (Manchand, et al., 1988) is employed. A solution of methyl (2S,3S)-4-acetoxy-2,3-epoxybutanoate (81.8 g, 465 mmol) in methanol (450 mL) is cooled in an ice bath to 5° C. The solution is treated with solid sodium hydroxide at such a rate that the temperature remained less than 15° C. This mixture is stirred at 5° C. for 3 hours and diluted with dichloromethane (200 mL). The mixture is stirred at room temperature for 30 minutes. The solid is collected by filtration and washed with dichloromethane (200 mL). The resulting filter cake is dried in vacuo at room temperature to yield the title compound as a solid (58.8 g, 90% theoretical yield).

Methyl (2R,3R)-2-(t-BOC-amino)-3,4-dihydroxybutanoate. The general procedure of Manchand, et. al. (Manchand, et al., 1988) is employed. A solution of (2S,3S)-2,3-epoxy-4-hydroxybutanoic acid sodium salt (58 g, 414 mmol) in ammonium hydroxide (600 mL) is stirred at 50-55° C. for 45 hours. The solvent is removed and the residual water is removed as an azeotrope with toluene (400 mL) to give a dark oil. The oil is dissolved in methanol (400 mL) and the solution is cooled to 5° C. A solution of anhydrous HCl (50 g) in methanol (400 mL) is added to the stirred solution over 20 minutes. The solution is stirred overnight at room temperature and the solvent is removed to give a brown oil. The oil is dissolved in methanol (500 mL) and the solution is cooled to 5° C. The cold solution is treated with 1 N NaOH until the pH is approximately 8 as determined universal pH paper. The solution is diluted to a total volume of 1 L with water and sodium bicarbonate (53.4 g, 636 mmol) is added. Neat di-t-butyl dicarbonate (126 g, 576 mmol) is added so that the reaction temperature remains below 30° C. After addition, the reaction is stirred overnight at room temperature. A portion of the methanol (ca. 450 mL) is removed by evaporation and the concentrate is cooled to 5° C. The cold concentrate is diluted with ether and the mixture is stirred at 5° C. for 30 minutes. The resulting solid is collected by filtration and washed with water (200 mL) and cold (5° C.) ether. The filter cake is dried to yield the title compound as a solid.

(2R,3R)-2-(t-BOC-amino)-3,4-dihydroxybutanoic acid. A solution of methyl (2R,3R)-2-(t-BOC-amino)-3,4-dihydroxybutanoate is dissolved in 95% ethanol and an excess of 2 N potassium hydroxide is added. The solution is stirred overnight at room temperature and the ethanol is removed by evaporation. The pH of the resulting solution is carefully raised to 4 by the addition of 10% hydrochloric acid. The mixture is extracted with ethyl acetate. The extract is washed with water and brine and dried over sodium sulfate. The solvent is removed to yield the title compound.

2,4,6-Trimethylbenzyl (2R,3R)-2-(t-BOC-amino)-3,4-dihydroxybutanoate. A mixture of (2R,3R)-2-(t-BOC-amino)-

3,4-dihydroxybutanoic acid, 2,4,6-trimethylbenzyl bromide (1.1 eq.) and triethyl amine (1.1 eq.) in dimethylformamide is stirred overnight at 50° C. The reaction is allowed to cool to room temperature and added to water. The mixture is extracted with ethyl acetate. The extract is washed with water and brine and dried over sodium sulfate. The product is purified by chromatography on silica gel with methanol/dichloromethane elution. The solvent is removed from the pure product fractions to yield the title compound.

2,4,6-Trimethylbenzyl (2R,3R)-2-(t-BOC-amino)-3-hydroxy-4-tetrahydropyranyloxybutanoate. A solution of 2,4,6-trimethylbenzyl (2R,3R)-2-(t-BOC-amino)-3,4-dihydroxybutanoate (1 eq.) in dry dichloromethane is prepared at room temperature. The solution is cooled to −20° C. and pyridinium-p-toluenesulfonate (0.1 eq.) is added followed by dihydropyran (1.1 eq.). After addition, the reaction is stirred overnight at −20° C. The solution is washed with water and brine and dried over magnesium sulfate. The solvent is removed to yield the title compound.

2,4,6-Trimethylbenzyl (2R,3R)-2-(t-BOC-amino)-3-mesyloxy-4-tetrahydropyranyloxybutanoate. The general procedure of Manchand, et. al. (Manchand, et al., 1988) is employed. A solution of 2,4,6-trimethylbenzyl (2R,3R)-2-(t-BOC-amino)-3-hydroxy-4-tetrahydropyranyloxybutanoate (1 eq.) is prepared in 1,2-dimethoxyethane. The solution is cooled to −20° C. and triethyl amine (3 eq.) is added. Methanesulfonyl chloride (2.4 eq.) is added drop wise to the stirred solution. The reaction mixture is stirred for an additional hour at −20° C. and saturated brine is slowly added. The mixture is extracted with ethyl acetate. The extract is washed with saturated brine and dried over magnesium sulfate. The solvent is removed and the residue is crystallized to yield the title compound.

2,4,6-Trimethylbenzyl (2R,3S)-2-(t-BOC-amino)-4-tetrahydropyranyloxy-3-(triphenylmethylmercapto)butanoate. A solution of 2,4,6-trimethylbenzyl (2R,3R)-2-(1-BOC-amino)-3-mesyloxy-4-(tetrahydropyranyloxy)butanoate (1.0 eq.), triphenylmethylmercaptan (2.0 eq) and triethyl amine (2.0 eq) in DMF is stirred at 80 C for 24 hours. The reaction is allowed to cool to room temperature and added to water. The mixture is extracted with ethyl acetate. The ethyl acetate portion is washed with water and brine and dried over sodium sulfate. The solvent is removed. The residue is purified on by chromatography on silica gel with ethyl acetate hexanes elution. Solvent removal from the pure fractions yields the title compound.

2,4,6-Trimethylbenzyl (2R,3S)-2-(t-BOC-amino)$_4$-hydroxy-3-(triphenylmethylmercapto)butanoate. A solution of 2,4,6-trimethylbenzyl (2R,3S)-2-(t-BOC-amino)-4-tetrahydropyranyloxy-3-(triphenylmethylmercapto)butanoate in acetic acid:tetrahydrofuran:water (4:2:1) is stirred at 45° C. for 3.5 hours. The solvent is removed to yield the title compound.

2,4,6-Trimethylbenzyl (2R,3S)-2-(t-BOC-amino)-4-mesyloxy-3-(triphenylmethylmercapto)butanoate. A solution of 2,4,6-trimethylbenzyl (2R,3S)-2-(t-BOC-amino)-4-hydroxy-3-(triphenylmethylmercapto)butanoate (1.0 eq.) is prepared in 1,2-dimethoxyethane. The solution is cooled to −20° C. and triethyl amine (3.0 eq.) is added. Methanesulfonyl chloride (2.4 eq.) is added drop wise to the stirred solution. The reaction mixture is stirred for an additional hour at −20° C. and saturated brine is slowly added. The mixture is extracted with ethyl acetate. The extract is washed with saturated brine and dried over magnesium sulfate. The solvent is removed and the residue is purified by chromatography on silica gel with ethyl acetate hexanes elution. The solvent is removed from the pure product fractions to yield the title compound.

2,4,6-Trimethylbenzyl (2R,3S)-2-(t-BOC-amino)-4-(2,6-dibromo-4-cyanophenyl)oxy-3-(triphenylmethylmercapto) butanoate. A solution of 2,4,6-trimethylbenzyl (2R,3S)-2-(t-BOC-amino)$_4$-mesyloxy-3-(triphenylmethylmercapto) butanoate (1.0 eq), 2,6-dibromo-4cyanophenol (2.0 eq) and potassium carbonate (2.0 eq) in DMF is stirred at 80° C. for 24 hours. The reaction is allowed to cool to room temperature and added to water. The mixture is extracted with ethyl acetate. The extract is washed with water and brine and is dried over sodium sulfate. The solvent is removed and the residue is purified by chromatography on silica gel with ethyl acetate in hexanes elution. The solvent is removed from the pure product fractions to yield the title compound.

(2R,3S)-2-Amino-4-(2,4-dibromo-4-cyanophenyl)oxy-3-mercaptobutanoic acid trifluoroacetate. A solution of 2,4,6-trimethylbenzyl (2R,3S)-2-(t-BOC-amino)-4-(2,6-dibromo4-cyanophenyl)oxy-3-(triphenylmethylmercapto) butanoate (1 eq.) and phenol (4 eq.) in trifluoroacetic acid is heated at reflux for 30 minutes. The reaction is allowed to cool to room temperature and is diluted with water. The solution is extracted with ether and the solvent is removed from the aqueous phase. The residue is crystallized from ethanol to yield the title compound.

D-2-(6'-Hydroxybenzothiazol-2'-yl)-D2-5-(2,6-dibromo-4-cyanophenoxy)methylthiazoline-4-carboxylic acid. A solution of 2-cyano-6-hydroxybenzothiazole (2.0 eq.) in MeOH is purged with nitrogen for 5 minutes. A solution of (2R,3S)-2-amino-4-(2,4-dibromo4-cyanophenyl)oxy-3-mercaptobutanoic acid trifluoroacetate (1.0 eq.) and potassium carbonate (1.0 eq.) in deoxygenated water is added to the methanol solution. The reaction is stirred under nitrogen while being protected from light for 2 hours. The volume of the reaction is doubled with water and the resulting solution is made acidic with dilute hydrochloric acid. The mixture is extracted with ethyl acetate. The extract is washed with water and dried over sodium sulfate. The solvent is removed and the residue is triturated with ether. The residue is dried in vacuo to yield the title compound.

Example 28

Tissue Selective Ablation of Meristem Floral Initiator Cells In Luc Transformed *Arabidopsis Thaliana*

To test for induction of sterility and prevention of cross-pollination of recombinant plants, *Arabiposis thaliana* ecotype Columbia are transformed with a plasmid construct containing an LEAFY promoter (LFY) driven firefly luciferase (luc) gene by standard leaf disk techniques (Horsch, et al., 1988). The 2.3 kb BamHI fragment spanning the LFY promoter (Blazquez, et al., 1997) is inserted in front of the luc gene in plasmid pGL3 (available from Promega Corp., Madison, Wis.) using the BglII site. Transgenic plants are generated using the vacuum-filtration method of Berthold, et al. (Berthold, et al., 1993). Regenerated kanamycin-resistant T1 plants carrying LFY::luc are grown up in a greenhouse to allow seed to set. T2 seed of strongly expressing T1 lines are grown in sterile culture on MS medium containing kanamycin at 20° C. for 6 to 10 days in 16 hours light: 8 hours dark cycles and afterward in 12 hour light: 12 hour dark cycles. Plants are treated by spray application to the upper leaves and apical shoot sections, with 5 mM D-luciferin-bromoxynil in 0.01% aqueous triton X-100, 2 times per day, beginning on day 4, for a period of 7-20 days. Analysis of the apical shoot meristem of these treated recombinant plants indicate no transition to floral initiation during this time period. Control untransformed plants grown under identical conditions exhibit induction of floral initiation tissues in the apical meristem by microscopic and visual examination.

Example 29

Positive Selection of lacZ Transformed Mammalian Cells Using Growth-Regulatory Galactoside Conjugate Addition Murine fibroblast cell lines NIH/3T3 and leukemia virus transfected CREBAG2 (lacZ+) were obtained from the ATCC cell repository (Rockville, Md.) as frozen stocks, and were grown in culture (37° C., 10% $CO_2$, humidified incubator) using 1:1 DME:F12 media to establish stable growth. These cells were trypsinized, diluted to $5 \times 10^3$ cells/mL in DME:F12 media and plated into twelve-well culture plates (Falcon #3043). After overnight incubation the media was changed to a minimal F12:DME media with four components (myo-inositol, pantothenic acid, pyridoxine, and thymidine) omitted. The table below indicates the component mixture for this minimal media used.

Components of 1:1 DME:F12 Minimal Media (Components to weigh directly to 1 L Dist. D.I. water)

| Name | Weight |
| --- | --- |
| Calcium Chloride-2H2O | 154.5 mg |
| Magnesium Chloride-6H2O | 61.2 mg |
| Magnesium Sulfate (anhy.) | 48.84 mg |
| Potassium Chloride | 311.8 mg |
| Sodium Chloride | 6.996 g |
| Sodium phosphate Dibasic | 71.02 mg |
| Sodium Phosphate Monobasic | 54.3 mg |
| L-Alanine | 4.45 mg |
| Arginine HCl | 147.5 mg |
| Asparagine | 7.5 mg |
| Aspartic Acid | 6.65 mg |
| Cystine-HCl-H2O | 17.56 mg |
| Cystine 2HCl | 31.29 mg |
| Glutamic Acid | 7.35 mg |
| Glutamine | 365 mg |
| Glycine | 18.75 mg |
| Histidine-HCl-H2O | 31.48 mg |
| Isoleucine | 54.47 mg |
| Leucine | 59.05 mg |
| Lysine-HCl | 91.25 mg |
| Methionine | 17.24 mg |
| Phenylalanine | 35.48 mg |
| Proline | 17.25 mg |
| Serine | 26.25 mg |
| Threonine | 53.45 mg |
| L-Tryptophan | 9.02 mg |
| Tyrosine | 38.7 mg |
| Valine | 52.85 mg |
| Choline Chloride | 8.98 mg |
| Folic Acid | 2.66 mg |
| HEPES | 3.57 mg |
| Phenol Red | 8.1 mg |
| Pyruvic Acid-Na salt | 55 mg |
| insulin | 10 mg |
| transferrin | 25 mg |

(Components to Add from Solution)

| Name | [Initial] | | Volume Added/Liter |
| --- | --- | --- | --- |
| Cupric Sulfate-5H2O | 1.3 µg/L | 13 mg/L | 100 µL |
| FerricNitrate-9H2O | 50 µg/L | 50 mg/100 mL | 100 µL |
| Ferrous Nitrate-7H2O | 417 µg/L | 41.7 mg/100 mL | 1 mL |
| Zinc Sulfate-7H2O | 432 µg/L | 43.2 mg/100 mL | 1 mL |
| D-Biotin | 3.5 µg/L | 35 mg/L | 100 µL |
| Riboflavin | 219 µg/L | 21.9 mg/100 mL | 1 mL |
| Vitamin B-12 | 680 µg/L | 68 mg/100 mL | 1 mL |
| Linoleic Acid | 42 µg/L | 100 mg/23.8 mL | 100 µL |
| Putrescine-HCl | 81 µg/L | 81 mg/100 mL | 100 µL |
| Thioctic Acid | 105 µg/L | 105 mg/100 mL | 100 µL |
| Nioctinimide | 2.02 mg/L | 101 mg/50 mL | 1 mL |
| Pyridoxal | 2 mg/L | 101 mg/50 mL | 1 mL |
| Thiamine-HCl | 2.17 mg/L | 108.5 mg/50 mL | 1 mL |
| Hypoxanthine | 2.1 mg/L | 105 mg/50 mL | 1 mL |

Note:
All components added prior to dilution to 1.0 L.

Cell media were prepared starting from the base minimal F12:DME and adding (1) glucose (0.63 g/L), (2) lactose (1.26 g/L), (3) glucose (0.63 g/L) and myo-inositol β-D-galactoside (0.239 g/L), pantothenic acid di-β-D-galactoside ($3.76 \times 10^{-3}$ g/L), thymidine β-D-galactoside ($6.09 \times 10^{-4}$ g/L) and pyridoxine β-D-galactoside ($6.07 \times 10^{-5}$ g/L), (4) lactose (1.26 g/L) and myo-inositol β-D-galactoside (0.239 g/L), pantothenic acid di-β-D-galactoside ($3.76 \times 10^{-3}$ g/L), thymidine β-D-galactoside ($6.09 \times 10^{-4}$ g/L) and pyridoxine β-D-galactoside ($6.07 \times 10^{-5}$ g/L), or nothing (blank). Cells were allowed to grow in these media for 1-4 days, and the number of viable cells counted using the MTT assay (Plumb, et al., 1989). After 3-4 days in culture, the differential growth of the CREBAG2 (lacZ+) cells versus NIH/3T3 cells (lacZ−) was obtained. These observations indicate that other combinations of growth-factor conjugates, application dynamics, or cell lines may also be used for positive selection of lacZ+ cells in culture.

| | NIH3T3 Relative Cell Growth | CREBAG2 Relative Cell Growth |
| --- | --- | --- |
| Glc + 4V | 0.0925 | 0.1560 |
| Lac + 4VGal | −0.0124 | 0.0269 |
| Glc + 4VGal | 0.0078 | 0.0300 |
| Glc only | 0.00 | 0.00 |

Example 30

Differential Growth of Amp-Containing Recombinant Bacteria by Application of an Ampicillin Conjugate

*Xanthomonas* strains were kindly provided by Don Crawford, Culture Curator for the Nutrasweet Kelco Company (San Diego, Calif.). Appropriate permits for transport of these strains were obtained from the USDA. *X. Campestris* XN1 is a nalidixic acid-resistant derivative of *X. campestris* NRRL B-1459S4L. *X. campestris* CL355 is an XN1 derivative containing plasmid pGC9114, a plasmid containing the lac transposon Tn951, and conferring resistance to ampicillin, kanamycin, and tetracycline (Walsh, et. al, 1984).

Strains were reconstituted from freeze dried cultures by addition of 1 ml of Luria-Bertani glucose (LBG) broth. Suspended cultures were then added to nutrient agar slants and incubated at 30° C. until growth was observed. Individual colonies of these strains were then grown and maintained in LBG broth.

*X. campestris* strains XN1 and CL355 were grown in M9 minimal media plus 0.2% glucose. The glutamate-ammonia ligase inhibitor phosphinothricin (PPT) was added to three XN1 and CL355 cultures at a concentration of 5 µM. L-glutamate (20 µg/ml) was added back to one XN1 and CL355 culture containing 5 µM PPT. Phenylacetyl-cephalosporanic acid-glutamate (M0182) (63 µg/ml, equimolar to 20 µg/ml L-glutamate) was added to XN1 and CL355 cultures containing 5 µM PPT. Control cultures containing no additions were also included. Growth of cultures was monitored by recording change in absorbance at 600 nm over time. Differential growth of strains containing the ampicillin-glutamate derivative is noted for the recombinant bacteria (*X. campestris* CL355) versus non-transformed strain XN1. The final growth results in media of M9+0.2% glucose+PPT (20 µg/mL)+M0182 (63 µg/mL) were 0.471 at Abs. (600 nm) for CL355 and 0.101 at Abs. (600 nm) for XN1.

Example 31

The In Vivo Response to Doxorubicin-Galactoside Treatment of Tumor Cells Lipofected with a lacZ Containing Vector in Mice To test the efficacy of pro-drug delivery in vivo for initiation and mediation of a host cellular immune response to genetically modified tumor, C57/J(B6) mice (22-36 g each) are injected intravenous with 50 μL HBBS containing $1\times10^6$ D5 tumor cells that are either untreated, lipofected with a vector containing the lacZ gene, lipofected with a vector containing both the lacZ and the H-2K allogeneic major histocompatability complex (MHC) class I gene (Wahl, et al, 1995), or lipofected with a vector containing the H-2K gene alone. After 2 days, accumulation of the tumor cells in the lung tissue is expected. Two animals are retained as controls, and necropsy examination and tumor staining of the lipofected animals is performed at the end of the trial, to confirm pulmonary tumor growth.

The doxorubicin-galactoside pro-drug of Example 19 is administered intraperitoneally starting at Day 3, for 20 days, to mice that received lipofected tumor cells in doses of either 5, 10 or 25 mg/kg/day, and to mice that received untreated tumor cells in doses of 50 mg/kg/day. Measurement of tumor growth is determined by necropsy examination of lung tissue and staining at day 25. Tumor regression is noted in lipofected animals versus tumor growth in those animals receiving the non-transformed tumor cells. In addition, those animals receiving both lacZ and H-2K gene exhibit lower tumor burden, presumably due to a host cellular immune response, initiated by the selective drug delivery.

Example 32

Phase I Clinical Study Involving Administration of the lacZ Marker Gene to DeltaF508 CFTR Defective Lung Epithelial Cells with Subsequent Pro-Drug Therapy In vivo transformation of deltaF508 CFTR defective lung epithelial cells with a vector containing the lacZ gene will be effected using either a lipofection technique (see Canonico, A. E., Plitman, J. D., Conary, J. T., Meyrick, B. O., Brigham, K. L., J. Appl. Physiol. 1994 77(1): 415-419) or a retroviral vector (see Yoshimura, K., Rosenfeld, M. A., Seth, P., Crystal, R. G., J. Biol. Chem. 1993 268(4): 2300-2303) technique. Four patients will be subjected to lacZ transformation on day 0. Approximately 24 hours after cell transformation, the patients will be started on a 10 day course of I.V. pro-drug administration. Two weeks after the termination of pro-drug therapy, each patient will be evaluated in terms of side-effects from treatment, and progression of the disease state. If no adverse toxicity occurred from the previous cell treatment and pro-drug therapy, and there appears to be no evidence of increased immune response that would require alternate therapy, then the patient will be eligible for the next regimen of cellular/pro-drug therapy. This schedule will continue for regimens of 1, 3 and 5 repetitions for Group 1. If no adverse side effects warranting the stoppage of therapy are reported in Group 1, then Group 2 patients will be treated at one dose level higher, and this pattern will continue through four groups. If a patient has to drop out of the study for reasons other than toxicity, then another patient may be added to the group and will begin therapy at the lowest dose level for that group. The patients will be admitted to the hospital for the first two days of each cycle. The transformation of cells will be performed on day 1 and pro-drug treatment on days 2 through 15, with day 3-15 pro-drug treatment on an out-patient basis. The treatment is repeated at three week intervals for a total of one to five cycles of treatment. At the completion of treatment, patients will be followed regularly until, and if there is a progression of disease for bacterial infection, CFTR function, and pulmonary function.

Cellular Transformation and Pro-Drug Administration.

Patients will be assigned in order of entrance in the study to one of the four treatment schedules below. The dosages escalate with each treatment unless toxicity of Grade II or higher has occurred. For Grade II toxicity, except for nectropenia or thrombocytopenia, the dose is repeated but physician discretion could lower the dose if overall toxicity is of concern. For Grade III or Grade IV toxicity, the dosage is lowered one level. The drug conjugates are all prepared from FDA-approved drugs used for treatment of human cancers. The bioavailability and clearance levels of pro-drugs are required to be measured prior to treatment. The pro-drugs will be provided as a sterile powder and they are reconstituted with sterile water.

For I.V. administration, these will be prepared in 100 cc of normal saline, or 5% dextrose and water, and infused over a period of one hour. The drugs to be administered are 15-Deoxyspergualin β-D-galactoside and Genistein-β-D-galactoside for CFTR membrane expression regulation, tobramycin β-D-galactoside for reduction of pulmonary lung bacterial infection, and the bronchodilator albuterol β-D-galactopyranoside to improve pulmonary function.

The standard dose of these drugs will be from 0.5 to 10 mg/kg b.i.d. when patients have a creatine clearance >80. If the creatine clearance level is 50-79, the dose is reduced to by one-half to 0.25-2.5 mg/kg b.i.d. Exact drug levels and combination drug therapy will be determined at the time of treatment. Daily CBC and platelet counts will be obtained during treatment. The pro-drug administrations should be stopped if the absolute granulocyte count falls below 750 or the platelets are less than 50,000 count.

Example 33

Preparation of a Bromoxynil Glucuronide Triacetate, Methyl Ester Conjugate (M0630)

The following compound was prepared:

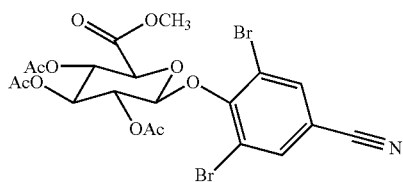 [SMILES: COC(=O)C1OC(Oc2c(Br)cc(C#N)cc2Br)C(OC(C)=O)C(OC(C)=O)C1OC(C)=O]

Bromoxynil (2,6-dibromo-4-cyanophenol) (1.00 g, 3.61 mmole) was dissolved in anhydrous dichloromethane (35 mL) containing 3 Å molecular sieves (1 gram). Sym-collidine (477 µL, 3.61 mmole), dry silver carbonate (695 mg, 2.52 mmole) and acetobromoglucuronic acid, methyl ester (2.00 g, 5.04 mmole) were added sequentially under anhydrous conditions, and this mixture allowed to stir under anhydrous nitrogen gas, in the dark, for 72 hours at 25° C. T.l.c. analysis ($SiO_2$ plate; irrigant=9:1 dichloromethane:methanol) showed the production of one major product (Rf=0.8). The reaction mixture was filtered through a Celite™ or diatomaceous earth pad and the precipitate washed with fresh dichloromethane (5×10 mL). The combined filtrates were extracted with water, 1 N aqueous hydrochloric acid solution, saturated aqueous sodium bicarbonate solution, 2% aqueous ammonium hydroxide solution and water (1×50 mL each). The combined organic layers were dried over anhydrous sodium sulfate, filtered, evaporated to dryness and dried in vacuo. The crude sample was applied to a column of Silicagel G (70-230 mesh, 100 grams) and eluted by gradient elution with dichloromethane containing methanol (0%, 500mL; 5%, 400 mL and 10% 400 mL) as irrigant. The second major product to elute from the column was combined, evaporated, and dried in vacuo to give a white foam (1.082 g, 51% theoretical yield). $^1$H-n.m.r. analysis ($CDCl_3$) indicated exclusive production of the beta-galactoside product.

Example 34

Preparation of a Bromoxynil Glucuronide, Methyl Ester Conjugate (M0632)

The following compound was prepared:

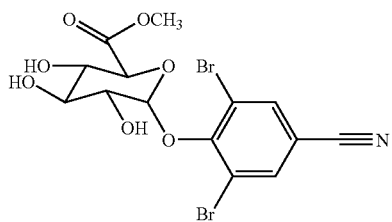 [SMILES: COC(=O)C1OC(Oc2c(Br)cc(C#N)cc2Br)C(O)C(O)C1O]

The per-acetate methyl ester M0630 from Example 40 (100 mg, 0.17 mmole) is suspended in anhydrous methanol (40 mL) under anhydrous nitrogen, and sodium methoxide/methanol (25% w/v) added (0.11 mL). This mixture is allowed to stir at 0° C. for 1 hour and at room temperature for 2 hour until t.l.c. analysis (SiO2: irrigant=9:1 $CH_2Cl_2$) indicated that the starting material had been consumed and a new product (Rf=0.22) formed. The reaction was neutralized with washed, dry IRC50(H+) resin, the resin filtered and washed with methanol (6×10 mL) and the filtrate evaporated to a white solid. This sample was redissolved in methanol and applied to a preparative thin layer chromatography sheet (20× 20 cm, 1 mm thickness) and eluted with 9:1 dichloromethane:methanol. The band corresponding to the lowest Rf product was removed from the plate, and the product eluted from the silicagel with 7:3 ethylacetate:methanol. After filtering, and evaporation, the product (58 mg, 74%) was obtained, homogeneous by t.l.c. ($SiO_2$: irrigant=7:3 ethylacetate:methanol).

Example 35

Preparation of a Maleic Hydrazide Beta-D-Glucuronide Triacetate, Methyl Ester Conjugate (M0627)

The following compound was prepared:

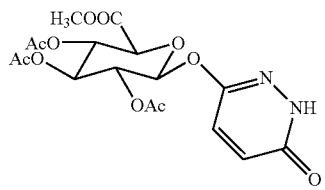

To a flame dried flask, under anhydrous nitrogen gas, maleic hydrazide (3,6-Dihydroxypyridazine) (1.00 g, 8.92 mmole) was suspended in anhydrous dichloromethane (25 mL) and 3 Å molecular sieves (1 gram) added. This mixture was allowed to stir at room temperature for 20 min. and sym-collidine (1.32 mL, 10.0 mmole), anhydrous silver triflate (3.40 g, 13.3 mmole) and acetobromoglucuronic acid, methyl ester (5.30 g, 13.38 mmole) added sequentially under anhydrous conditions. This mixture allowed to stir under anhydrous nitrogen gas, in the dark, for 72 hours at 25° C. T.l.c. analysis ($SiO_2$ plate; irrigant=9:1 dichloromethane:methanol) showed the production of one major product (Rf=0.35). The reaction mixture was filtered through a Celite™ or diatomaceous earth pad and the precipitate washed with fresh dichloromethane (5×10 mL). The combined filtrates were extracted with water, 1 N aqueous hydrochloric acid solution, saturated aqueous sodium bicarbonate solution, and brine solution (1×50 mL each). The combined organic layers were dried over anhydrous magnesium sulfate, filtered, evaporated to dryness and dried in vacuo. The crude sample was applied to a column of Silicagel G (70-230 mesh, 150 grams) and eluted by gradient elution with dichloromethane containing methanol (0%, 4 L; 10% 1.4 L; 20% 1.4 L; 40% 2 L and 50% 500 mL) as irrigant. Fractions containing the second major product to elute from the column was combined, evaporated, and dried in vacuo to give an off-white foam (663 mg, 17% theoretical yield). $^1$H-n.m.r. analysis ($CDCl_3$) was consistent with the beta-galactoside product.

Example 36

Preparation of a Cycloheximide Beta-D-Glucuronide Triacetate, Methyl Ester Conjugate (M0792)

The following compound was prepared:

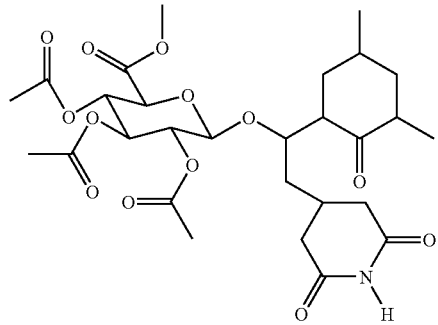 [SMILES: COC(=O)C1OC(OC(CC2CC(=O)NC(=O)C2)C2CC(C)CC(C)C2=O)C(OC(C)=O)C(OC(C)=O)C1OC(C)=O]

Actidione (cycloheximide) (1.105 g, 3.92 mmole) was dissolved in anhydrous dichloromethane (50 mL) containing 3 Å molecular sieves (1 gram). Sym-collidine (529 uL, 4.0 mmole), dry silver carbonate (599 mg, 2.0 mmole) and acetobromoglucuronic acid, methyl ester (1.59 g, 4.0 mmole) were added sequentially under anhydrous conditions, and this mixture allowed to stir under anhydrous nitrogen gas, in the dark, for 72 hours at 25° C. T.l.c. analysis (SiO$_2$ plate; irrigant=8:2 dichloromethane:ethylacetate) showed the production of one major product (Rf=0.2). The reaction mixture was filtered through a Celite™ or diatomaceous earth pad and the precipitate washed with fresh dichloromethane (5×10 mL). The combined filtrates were extracted with water, 1 N aqueous hydrochloric acid solution, saturated aqueous sodium bicarbonate solution, 2% aqueous ammonium hydroxide solution and water (1×50 mL each). The combined organic layers were dried over anhydrous magnesium sulfate, filtered, evaporated to dryness and dried in vacuo. The crude sample was applied to a column of silicagel G (70-230 mesh, 150 grams) and eluted by gradient elution with dichloromethane containing methanol (0%, 600 mL; 10% 1 L and 20% 2 L) as irrigant. Fractions containing the third major product to elute from the column were combined, evaporated, and dried in vacuo to give a white foam (218 mg, 9% theoretical yield). $^1$H-n.m.r. analysis (CDCl$_3$) was consistent with the structure of the beta-galactoside product.

Example 37

Preparation of a Deoxynojirimycin Beta-D-Glucuronide, Methyl Ester Conjugate (M0809)

The following compound was prepared:

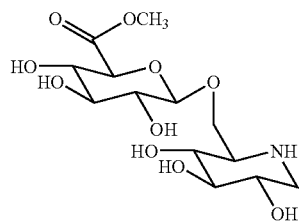 [SMILES: COC(=O)C1OC(OCC2NCC(O)C(O)C2O)C(O)C(O)C1O]

To a solution of deoxynojirimycin (17 mg, 0.105 mmole) in anhydrous tetrahydrofuran (8 mL) was added di-t-butyldicarbonate (43 mg, 0.197 mmole, 1.9 equivalents) and triethylamine (16.7 uL, 1.0 equivalents) and this mixture allowed to stir at room temperature under anhydrous conditions (dry N2(g)) for 4 hours. The reaction mixture was evaporated to dryness in vacuo, redissolved in water:methanol (1:1) (10 mL), evaporated, and co-evaporated with methanol (3×10 mL) and dried in vacuo to a white solid (28 mg, 100%). $^1$H-n.m.r. (D2O) exhibited a new singlet (9H) for the t-butyloxycarbonyl derivative (M0761).

The crude M0761 was suspended in anhydrous dichloromethane (10 mL) under anhydrous conditions (dry N2(g)) and 3 Å molecular sieves (0.5 gram), sym-collidine (28 uL, 0.210 mmole), dry silver carbonate (29 mg, 0.105 mmole) and acetobromoglucuronic acid, methyl ester (83 mg, 0.210 mmole) were added sequentially under anhydrous conditions. This reaction mixture was allowed to stir in the dark at room temperature under dry N$_2$(g) for 4 days, until a new ninhydrin positive product (t.l.c. (CH$_2$Cl$_2$) Rf=0.8, SiO$_2$ plate) was produced. The reaction mixture was filtered through a Celite™ or diatomaceous earth pad and the precipitate washed with fresh dichloromethane (5×10 mL). The combined filtrates were extracted with water, 1 N aqueous hydrochloric acid solution, saturated aqueous sodium bicarbonate solution, 2% aqueous ammonium hydroxide solution and water (1×50 mL each). The combined organic layers were dried over anhydrous magnesium sulfate, filtered, evaporated to dryness and dried in vacuo. The crude sample was applied to a column of silicagel G (70-230 mesh, 25 grams) and eluted by gradient elution with ethylacetate containing methanol (0%, 250 mL; 10% 500 mL, 15% 400 mL and 20% 100 mL) as irrigant. Fractions containing the second major product to elute from the column were combined, evaporated, and dried in vacuo to give a white foam (25 mg, 41% theoretical yield). $^1$H-n.m.r. analysis (CDCl$_3$) was consistent with the structure of the fully protected beta-galactoside product (M0768). The fully protected product (M0768, 25 mg, 43 mmole) was suspended in anhydrous dichloromethane and trimethylsilyl iodide (75 uL, 10 equivalents) added. This mixture was allowed to stir at ambient temperature under anhydrous conditions for 4 hours, after which time, dry methanol (2 mL) was added to quench the reaction. The reaction mixture was evaporated to dryness in vacuo (no heat) and redissolved in 1:1 water; diethylether (10 mL). The ether layer was separated, and the lower aqueous solution washed with diethyl ether (1×10 mL). The aqueous layer was lyophilized to a off-white solid, that was recrystallized from methanol:diethylether to give a white powder (7 mg, 44%, homogeneous by t.l.c. analysis. $^1$H-n.m.r. (D2O) was consistent with the methyl ester glucuronide structure.

Example 38

Preparation of a Deoxymannonojirimycin Beta-D-Glucuronide Triacetate, Methyl Ester Conjugate (M0872)

The following compound was prepared:

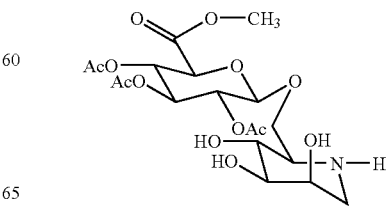

A sample of D-fructose, pentaacetate (prepared by the method of Helefrich, B., Steinpreis, R., Chem. Ber. (1958) 91: 1794-1798) (2.86 g, 11.3 mmole) was dissolved in dry dichloromethane (50 mL) and dry pyridine (0.5 µL, 6.2 mmole), and triphenylphosphine dibromide (6.35 g, 14.7 mmole) added. This mixture was heated to reflux under dry $N_2(g)$ for 4 hours, cooled to room temperature, and saturated sodium bicarbonate solution (100 mL) was added slowly with stirring to destroy the excess triphenylphosphine bromide. The organic layer was separated and extracted with 5% sodium bicarbonate solution (1×50 mL) and 1 N HCl solution (1×50 mL). The organic layer was dried over anhydrous magnesium sulfate, filtered, and evaporated in vacuo to a light tan solid. The crude product was recrystallized from hot 2-propanol to give a white solid (M0760) (2.84 g, 61%) with $^1$H-n.m.r.(CDCl$_3$) consistent with the 6-bromodeoxy derivative. A second reaction yielded an additional 0.65 grams M0760.

A solution of M0760 (3.00 g, 7.28 mmole) in anhydrous methanol (75 mL) was treated with sodium methoxide/methanol (1.0 mL, 25% w/v, 4.63 mmole) and allowed to stir at room temperature under anhydrous conditions (dry $N_2(g)$) for 18 hours. The reaction mixture was neutralized with washed, dry IRC-50 (H+) resin, filtered and the resin washed with excess methanol (5×10 mL). The combined filtrates were adsorbed onto Celite™ 545 and dried in vacuo overnight. The crude product was applied to a column of silicagel G (70-230 mesh, 160 grams) and eluted by gradient elution with ethylacetate containing methanol (0%, 1 L; 5% 500 mL, 10% 1.3 L, and 20% 1.5 L) as irrigant. Fractions containing the second major product to elute from the column were combined, evaporated, and dried in vacuo to give a white foam (830 mg, 47% theoretical yield). $^1$H-n.m.r. analysis (CDCl$_3$) was consistent with the structure of the 6-deoxybromo product (M0777).

The sample of M0777 (830 mg, 3.42 mmole) was dissolved in anhydrous dimethylformamide (25 mL) and sodium azide (4.00 g, 61.5 mmole) added. This reaction mixture was allowed to stir under anhydrous conditions, in the dark for 8 days, diluted with dichloromethane (50 mL), filtered, and the filtrate washed with minimum dichloromethane. The combined filtrates were adsorbed onto Celite™ 545 and dried in vacuo overnight. The crude product was applied to a column of silicagel G (70-230 mesh, 80 grams) and eluted by gradient elution with ethylacetate containing methanol (0%, 150 mL, 10% 500 mL, and 20% 500 mL) as irrigant. Fractions containing the first major product to elute from the column were combined, evaporated, and dried in vacuo to give a white foam (130 mg, 19% theoretical yield). $^1$H-n.m.r. analysis (CDCl$_3$) was consistent with the structure of the 6-deoxy-6-azido product (M0779).

A sample of M0779 (130 mg, 0.633 mmole) was dissolved in methanol (15 mL) and subjected to hydrogenation (1.1 bar, with 5% Pd/C (50 mg) for 4 hours. The catalyst was filtered and washed with fresh methanol, and the filtrate concentrated to a low volume (about 5 mL) and crystallized by addition of diethylether (50 mL) to give deoxymannonojirimycin (M0801) (99 mg, 96%) consistent by $^1$H-n.m.r. (D20) and t.l.c. analysis with an authentic sample.

A sample of M0801 (138 mg, 0.846 mmole) was suspended in anhydrous dichloromethane (10 mL) and acetonitrile (10 mL) and treated with 3 Å molecular sieves (0.5 gram), sym-collidine (112 uL, 0.846 mmole), anhydrous silver triflate (230 mg, 0.895 mmole) and acetobromoglucuronic acid, methyl ester (336 mg, 0.846 mmole), added sequentially under anhydrous conditions. This mixture allowed to stir under anhydrous nitrogen gas, in the dark, for 6.5 days at 25° C. T.l.c. analysis (SiO$_2$ plate; irrigant=19:1 dichloromethane:ethylacetate) showed the production of one major product (Rf=0.8). The reaction mixture was filtered through a Celite™ or diatomaceous earth pad and the precipitate washed with fresh dichloromethane (5×10 mL). The combined filtrates were extracted with water, 1 N aqueous hydrochloric acid solution, saturated aqueous sodium bicarbonate solution, 2% ammonium hydroxide solution and brine solution (1×50 mL each). The combined organic layers were dried over anhydrous magnesium sulfate, filtered, evaporated to dryness and dried in vacuo. The crude sample was applied to a column of Silicagel G (70-230 mesh, 50 grams) and eluted by gradient elution (0-5% ethylacetate in dichloromethane). Fractions containing the first product to elute from the column were pooled and evaporated to dryness. Crystallization from methanol:diethylether gave an off-white solid (286 mg, 70%), homogeneous by t.l.c. analysis (5% ethylacetate: CH$_2$Cl$_2$). $^1$H-n.m.r. (d6-DMSO) was consistent with the beta-glucuronide product (M0872).

Example 39

Preparation of a 20-Hydroxyecdysone Beta-D-Glucuronide Triacetate, Methyl Ester Conjugate (M0767)

The following compound was prepared:

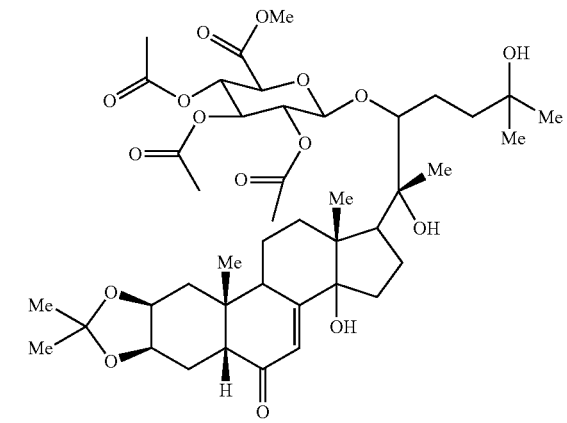 [SMILES: COC(=O)C1OC(OC(CCC(C)(C)O)[C@](C)(O)C2CCC3(O)C4=CC(=O)[C@@H]5C[C@H]6OC(C)(C)O[C@H]6C[C@]5(C)C4CC[C@]23C)C(OC(C)=O)C(OC(C)=O)C1OC(C)=O]

To a solution of 20-hydroxyecdysone (40.0 mg, 83.2 mmole) in anhydrous dimethylformamide (5.0 mL) was added dimethoxypropane (50 uL, 5 equivalents) and p-toluenesulfonic acid (10 mg). This mixture was allowed to stir at room temperature for 72 h. Water (10 mL) was added and the reaction mixture was extracted with ethylacetate (4×20 mL). The combined ethylacetate extracts were back-extracted with water (1×20 mL), dried over anhydrous magnesium sulfate, filtered, evaporated to dryness and dried in vacuo to give a white powder (43 mg, 100%) (M0763) $^1$H-n.m.r. analysis of the product was consistent with the isopropylidene derivative. The sample of M0763 (43 mg, 83 mmole) was suspended in anhydrous dichloromethane (10 mL) under anhydrous conditions (dry N2(g)) and 3 Å molecular sieves (0.5 gram), sym-collidine (22 uL, 0.166 mmole), dry silver carbonate (23 mg, 0.83 mmole) and acetobromoglucuronic acid, methyl ester (66 mg, 0.166 mmole) were added sequentially under anhydrous conditions. This reaction mixture was allowed to stir in the dark at room temperature under dry N$_2$(g) for 4 days, until a new product (Rf=0.9, irrigant=9:1 dichloromethane:methanol, SiO$_2$ plate) was formed. The reaction mixture was filtered through a Celite™ or diatomaceous earth pad and the precipitate washed with fresh dichloromethane (5×10 mL). The combined filtrates were extracted with water, 1 N aqueous hydrochloric acid solution, saturated aqueous sodium bicarbonate solution, and brine solution (1×50 mL each). The combined organic layers were dried over anhydrous magnesium sulfate, filtered, evaporated to dryness and dried in vacuo. The crude sample was applied to a column of Silicagel G (70-230 mesh, 40 grams) and eluted by gradient elution with dichloromethane containing methanol (0%, 200 mL; 10% 200 mL; 20% 150 mL; and 25% 300 mL) as irrigant. Fractions containing the first major product to elute from the column were combined, evaporated, and dried in vacuo to give an white foam (27 mg, 39% theoretical yield). $^1$H-n.m.r. analysis ($CDCl_3$) was consistent with the beta-galactoside product.

Example 40

Differential Growth of Gus-Containing Recombinant *Arabidopsis Thaliana* Plants by Application of a Beta-Glucuronide Conjugate

*Arabidopsis thaliana* Landsberg erecta is a wild type (WT) strain derived from the Landsberg ecotype. *Arabidopsis thaliana* Landsberg erecta strain DW150-307 (DW) is a transgenic strain produced using the method of Blazquez et al., 1997, *Development* 124:3835-3844. The transgenic DW strain is homozygous for the LFY::GUS insertion and thus contains GUS under control of the full length LFY promoter that expresses *E. coli* β-glucuronidase. Expression of GUS in this strain is developmentally regulated, showing the highest levels 9 days after germination (at the onset of meristem floral initiation under a long-day, 16 h. light regime), but having basal levels in vegetative apices throughout secondary growth. Accordingly, GUS expression leads to production of the *E. coli* β-glucuronidase enzyme in floral and to a lesser extent in shoot meristem tissues of the plant. Isogenic homozygous plant strains were kindly provided by Dr. Detlef Weigel, Department of Biology, The Salk Institute, San Diego, Calif.

Wild type (WT) and recombinant (DW) plants were grown in MS media containing 0-100 ug/mL of conjugates M0630, M0632, or M0792 (prepared as set forth herein). All plants were grown at 23° C. in long-day (16 hours light/8 hours dark) cycles, under a mixture of Cool White and Gro-Lux/WS fluorescent lights (Osram, Sylvania) and sterile conditions.

The differential growth patterns of the wild type (WT) versus recombinant (DW) plants grown on media containing the conjugates were distinct. All wild type strains grew slightly slower on media containing the highest concentration of conjugates M0792, M0627 and M0632 (100 ug/mL), but wild-type plants grown on media containing lower concentrations showed comparable growth to the blank controls. After 32 days growth, all of the WT plants containing conjugates (all concentrations) had grown full, functional flowers, with all WT plants grown on media with 100 μg/mL conjugates/1% DMSO-MS (highest concentration) having formed seed pods.

By contrast DW plants exhibited distinctive growth responses when grown on M0630 or M0792 containing MS media, with normal vegetative growth until inflorescence initiation. Upon inflorescence, floral tissues became chlorotic (brown) and became dehydrated and ablated.

With media application of M0632, DW plants either did not germinate or were ablated shortly after germination. However, the plants grown at the lowest concentration of conjugate (1 ug/mL) showed dramatic differential growth phenotypes. Media application of M0632 at 1 ug/mL for 32 days produced a callus formation for recombinant DW150-307 plants due to ablation of meristem growth.

Example 41

Influencing Glycosylation of Glycoproteins in Gus-Containing Recombinant *Arabidopsis Thaliana* Plants by Application of a Beta-Glucuronide Conjugate

*Arabidopsis thaliana* Landsberg erecta strain DW150-307 plants were propagated from seeds. Seeds were surface-sterilized with 70% ethanol (30 seconds) and 2% sodium hypochlorite (15 minutes), and then placed on a plant hormone-free MS agar medium. After incubation at 4° C. for 2 days, the seeds were cultured at 25° C. for one week while the daylight hours were kept to be 16 hours. The cotyledons were taken from the obtained sterile seedlings and then placed on an MS agar medium containing either deoxynojirimycin b-D-glucuronide methyl ester (M0809) (22 mg/L) or deoxymannonojirimycin b-D-glucuronidetriacetate, methyl ester (M0872) (25 mg/L) (regeneration medium in 9 cm Petri dish), and cultured under the same conditions as those described above for 6 days. Plants were transplanted into fresh media containing the same concentrations of M0809 or M0872 as above, and growth continued for an additional 19 days, until full seed pods were obtained. Plants grew normally on media containing the M0809 or M0872, except that the number of inflorescence stems was decreased (an average of 50%) in the treated plant specimens. Seed pods, floral and stem tissues from these plants were harvested, and seeds dried briefly in vacuo (10 mm Hg, 1 hour). Seeds were crushed, and carbohydrate content of all tissues analyzed using the ANTS and 1,5-EDANS labeling systems, followed by HPLC analysis and PAGE electrophoretic analysis. Carbohydrate patterns of glycoproteins were compared with control seeds (no M0809 or M0872 treatment) and found to be modified in structure.

Example 42

Negative Selection of Potato Transformant Plants Expressing the Gus Gene Using Gus-Conjugates Potato (May queen) pieces with sprouts are planted in a mixture of vermiculite and compost (1:1). After two weeks, the apical meristem culture of the grown sprouts is removed to obtain the sterile seedling plants. Sterile plants are then placed in MS liquid medium containing 2% sucrose, pH 5.7 (80 ml) and incubated with rotation at 25° C. in a well-lighted place to induce rooting. After two weeks, the rooted plants are transferred into MS liquid medium for microtuber induction (MS medium, 8% sucrose, pH 5.7, 40 ml medium in 100 ml Erlenmeyer flask) in the dark for 28 days. The microtubers are then cut into pieces (2 mm) and transferred into agar medium for regeneration (MS medium, 2% sucrose, 1 mg/l zeatin, 0.1 mg/l IAA, 1% agar). The pieces of the microtuber pre-cultured for two days are then immersed in an *Agrobacterium tumefaciens* strain LBA4404 suspension containing the binary plasmid pBI121 (Clontech, Palo Alto, Calif.) for transformation. The plasmid pBI121 carries the neomycin phosphotransferase (NPTII) gene and β-glucuronidase (GUS) gene. In this vector, the neomycin phosphotransferase (NPTII) gene is under the control of the nopaline synthase (nos) promoter and the terminator from nopaline synthase (nos) which provides polyadenylation signal. The neomycin phosphotransferase (NPTII) gene confers kanamycin resistance. The β-glucuronidase (GUS) activity is under the control of the cauliflower mosaic virus $^{35}$S promoter, providing constitutive expression in all tissues, and the terminator from nopaline synthase (nos) provides polyadenylation. *Agrobacterium tumefaciens* was grown overnight at 28° C. in liquid YEP medium (Sambrook J., Fritsch E. F., Maniatis T., Molecular Cloning: a laboratory manual. 2nd ed., Cold Spring Harbor, N.Y., 1989) supplemented with 25 mg/l rifampicin, 50 mg/l streptomycin, and 50 mg/l kanamycin. An overnight culture is diluted with liquid TE medium to 4×10$^8$ cells/ml for transformation.

A filter paper is placed on the agar medium, over the microtuber pieces and the co-culture is continued for 48 hours. The transfected microtubers are then washed 4-5 times in sterile distilled water to decrease the concentration of *Agrobacterium tumefaciens* and with a cefotaxime (250 mg/l) solution for 20 min, and then again with sterile distilled water (4-5 times). The microtubers are then transferred into an agar screening medium (MS medium, 2% sucrose, 1 mg/l zeatin, 1 mg/l IAA, 1% agar, 50 mg/l kanamycin, 500 mg/l Claforan, 1% agar). After about two months growth, the divided shoots are transferred into a rooting induction medium and then into a microtuber induction medium. The obtained GUS-positive plants are used for the analysis. Application of maleic hydrazide triacetate, methyl ester (MO627) (3.5 mg/L), bromoxynil-β-D-glucuronic acid methyl ester triacetate (M0630) (10 mg/L), Bromoxynil-β-D-glucuronic acid methyl ester (M0632) (10 mg·L), Cycloheximide-β-D-glucuronic acid methyl ester triacetate (M0792) (5 mg/L) either into the MS media, soil or by spray application (daily), causes selective ablation of GUS-positive plants but does not affect growth or morphology of wild-type plants.

Example 43

Negative Selection of Gus Transformed Plants by the Infection of Tomato Cotyledons with *Agrobacterium* and Application of β-Glucuronide Conjugates Tomato (cultivar, minitomato) seeds are surface-sterilized with 70% ethanol (30 seconds) and 2% sodium hypochlorite (15 minutes), and then placed on a plant hormone-free MS agar medium. The seeds are cultured at 25° C. for one week at 23° C. in long-day (16 hours light/8 hours dark) cycles, under a mixture of Cool White and Gro-Lux/WS fluorescent lights (Osram, Sylvania) and sterile conditions. The cotyledons are taken from the obtained sterile seedlings and then placed on an MS agar medium containing 2 mg/l of Zeatin and 0.1 mg/l of IAA (regeneration medium) in 9 cm Petri dishes, and cultured under the same conditions as those described above for 2 days.

*Agrobacterium tumefaciens* strain LBA4404 suspension containing the binary plasmid pBI121 (Clontech, Palo Alto, Calif.) is used for transformation. The plasmid pBI121 carries the neomycin phosphotransferase (NPTII) gene and β-glucuronidase (GUS) gene. In this vector, the neomycin phosphotransferase (NPTII) gene is under the control of the nopaline synthase (nos) promoter and the terminator from nopaline synthase (nos) which provides polyadenylation signal. The neomycin phosphotransferase (NPTII) gene confers kanamycin resistance. The β-glucuronidase (GUS) activity is under the control of the cauliflower mosaic virus $^{35}$S promoter, providing constitutive expression in all tissues, and the terminator from nopaline synthase (nos) provides polyadenylation. *Agrobacterium tumefaciens* is grown overnight at 28° C. in liquid YEP medium (Sambrook J., Fritsch E. F., Maniatis T., Molecular Cloning: a laboratory manual. 2nd ed., Cold Spring Harbor, N.Y., 1989) supplemented with 25 mg/l rifampicin, 50 mg/l streptomycin, and 50 mg/l kanamycin. An overnight culture is diluted with liquid TE medium to 4×10$^8$ cells/ml for transformation.

The cotyledons cultured for two days are collected in a sterilized Petri dish, and the *Agrobacterium* suspension is added to them to cause infection. Superfluous *Agrobacterium* suspension is removed from the cotyledons by using a sterilized filter paper. After further removing excess *Agrobacterium* suspension, a sterilized filter paper is placed on the medium in the Petri dish in order to prevent rapid propagation of *Agrobacterium*. The infected cotyledons are placed on this media and co-cultured for 24 hours.

The transfected cotyledons are then transferred into an agar screening medium (MS medium, 2% sucrose, 1 mg/l zeatin, 1 mg/l IAA, 1% agar, 50 mg/l kanamycin, 500 mg/l claforan, 1% agar) to select the GUS transformant plants. The regenerated shoots are then transferred into a new selecting medium to conduct further selection. Application of maleic hydrazide triacetate, methyl ester (M0627) (3.5 mg/L), bromoxynil-β-D-glucuronic acid methyl ester triacetate (M0630) (10 mg/L), bromoxynil-β-D-glucuronic acid methyl ester (M0632) (10 mg·L), cycloheximide-β-D-glucuronic acid methyl ester triacetate (M0792) (5 mg/L) either into the MS media, soil or by spray application (daily), causes selective ablation of GUS-positive plants but does not affect growth or morphology of wild-type plants.

The above examples are provided to illustrate the invention but not to limit its scope. Other variants of the invention will be readily apparent to one of ordinary skill in the art and encompassed by the appended claims. All publications, patents, and patent applications cited herein are hereby incorporated by reference.

What is claimed is:

1. A method of altering glycosylation of proteins in a plant cell comprising:
   (a) introducing into said plant cell a gene encoding glucuronidase;
   (b) administering in an amount effective to alter glycosylation an inactive conjugate of a nojirimycin glucuronide;
   wherein the glucuronidase releases the nojirimycin glucuronide from conjugation, thereby making it active,
   wherein the glucuronidase does not naturally occur in the targeted cells in an amount effective to release the nojirimycin glucuronide from conjugation; and
   wherein the nojirimycin glucuronide alters glycosylation of proteins in said plant cell.

2. The method of claim 1 wherein said gene encoding glucuronidase is an active component of GUS β-glucuronidase from the bacteria *Escherichia coli*.

3. The method of claim 1, wherein the inactive conjugate of the bioactive compound has a formula selected from the group consisting of:

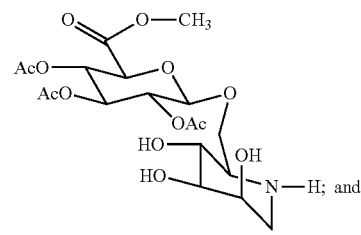

-continued
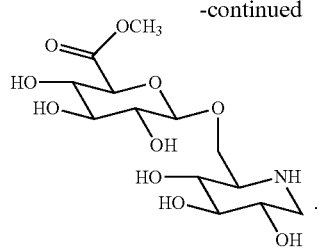
* * * * *